(12) United States Patent
Sekine

(10) Patent No.: US 7,911,342 B2
(45) Date of Patent: Mar. 22, 2011

(54) OPERATION STATE DETECTION DEVICE

(76) Inventor: Takaharu Sekine, Kani (JP)

(*) Notice: Subject to any disclaimer, the term of this patent is extended or adjusted under 35 U.S.C. 154(b) by 340 days.

(21) Appl. No.: 11/664,629

(22) PCT Filed: Sep. 12, 2005

(86) PCT No.: PCT/JP2005/016753
§ 371 (c)(1),
(2), (4) Date: Apr. 4, 2007

(87) PCT Pub. No.: WO2006/038434
PCT Pub. Date: Apr. 13, 2006

(65) Prior Publication Data
US 2007/0247312 A1    Oct. 25, 2007

(30) Foreign Application Priority Data

Oct. 5, 2004   (JP) ................................. 2004-292971

(51) Int. Cl.
*G08B 13/14* (2006.01)
(52) U.S. Cl. ................ 340/572.1; 340/568.1; 340/3.51; 340/825.23
(58) Field of Classification Search .... 340/572.1–572.9, 340/5.92, 539.1, 825.49, 568.1, 505, 3.51, 340/825.31, 825.23
See application file for complete search history.

(56) References Cited

U.S. PATENT DOCUMENTS

| | | | | |
|---|---|---|---|---|
| 4,591,854 A | * | 5/1986 | Robinson | 340/5.65 |
| 6,127,976 A | * | 10/2000 | Boyd et al. | 342/463 |
| 6,148,291 A | * | 11/2000 | Radican | 705/28 |
| 6,614,349 B1 | * | 9/2003 | Proctor et al. | 340/572.1 |
| 6,745,027 B2 | * | 6/2004 | Twitchell, Jr. | 455/422.1 |
| 7,010,501 B1 | * | 3/2006 | Roslak et al. | 705/26 |
| 7,082,316 B2 | * | 7/2006 | Eiden et al. | 455/519 |
| 7,322,043 B2 | * | 1/2008 | Letsinger | 726/19 |
| 2003/0031321 A1 | * | 2/2003 | Mages | 380/270 |

FOREIGN PATENT DOCUMENTS

| | | | |
|---|---|---|---|
| JP | 2002-009710 | * | 1/2002 |
| JP | 2002-9710 A | | 1/2002 |
| JP | 2002009710 A | | 1/2002 |
| JP | 2002-230182 A | | 8/2002 |
| JP | 20022611702 A | | 9/2002 |
| JP | 2003188834 A | | 7/2003 |
| JP | 2004034836 A | | 2/2004 |

OTHER PUBLICATIONS

Office Action in corresponding Japanese Appln. No. 2005-291142, Mar. 10, 2009.
Office Action of corresponding Japanese Patent Application JP2005291142 dated Jul. 1, 2009.
Japanese Office Action dated Oct. 6, 2009 issued in Japanese patent application No. 2009-014638.
Extended European Search Report dated Mar. 12, 2010 in corresponding EP application No. 05781921.1.

* cited by examiner

*Primary Examiner* — Daniel Previl
(74) *Attorney, Agent, or Firm* — Kinney & Lange, P.A.

(57) ABSTRACT

An operation state detection device comprises data communication devices and a detection device. The data communication devices are respectively attached to an operator, and a person or an object as an operation target. The data communication devices mutually perform data communication when the operator contacts the person or the object and thereby a path is formed through the operator, and the person or the object. The detection device detects the data communication performed between the data communication devices.

27 Claims, 62 Drawing Sheets

FIG.1
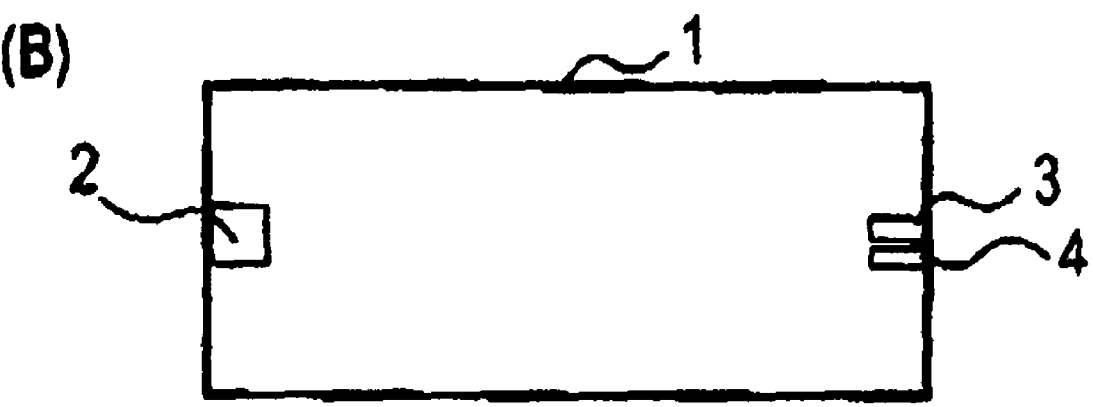

FIG.10
(A)
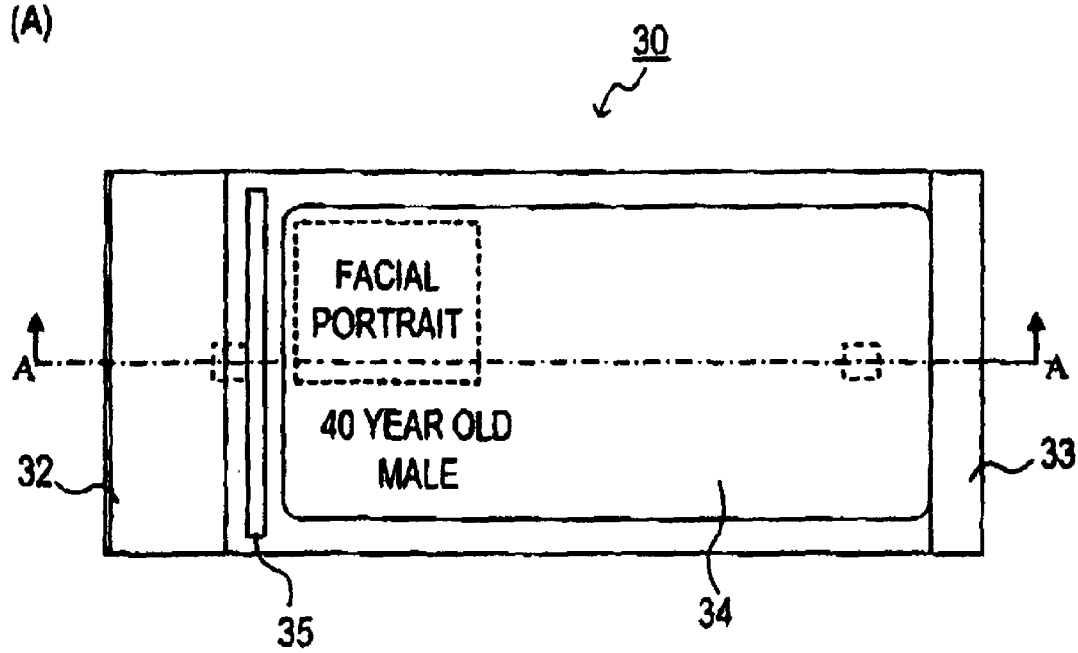
(B)
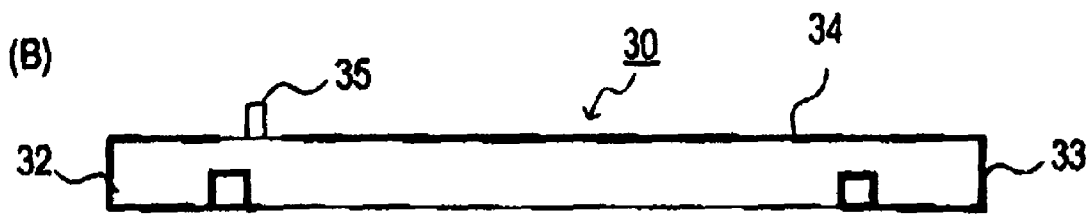

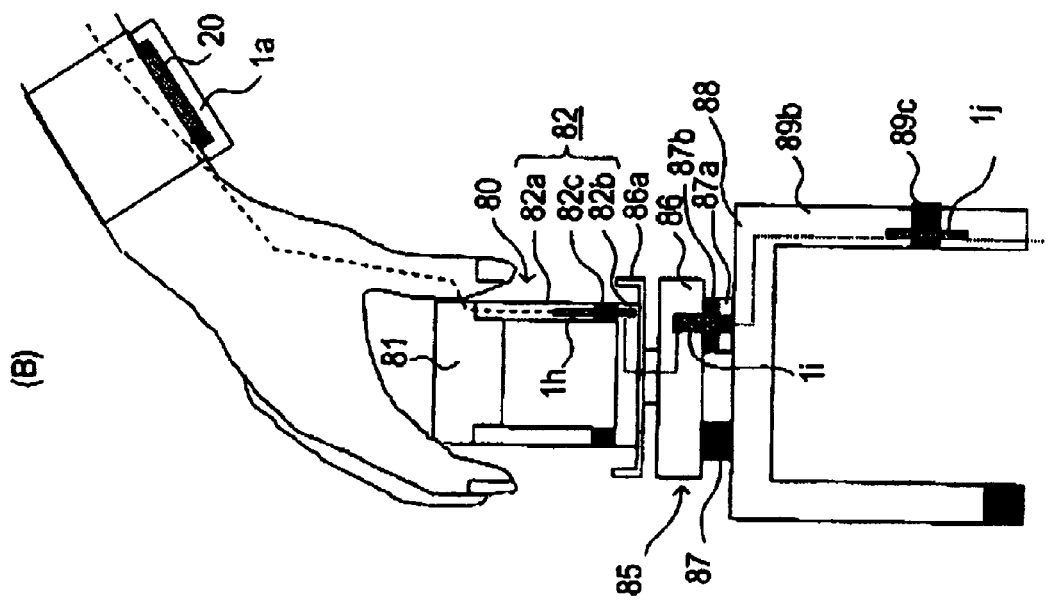
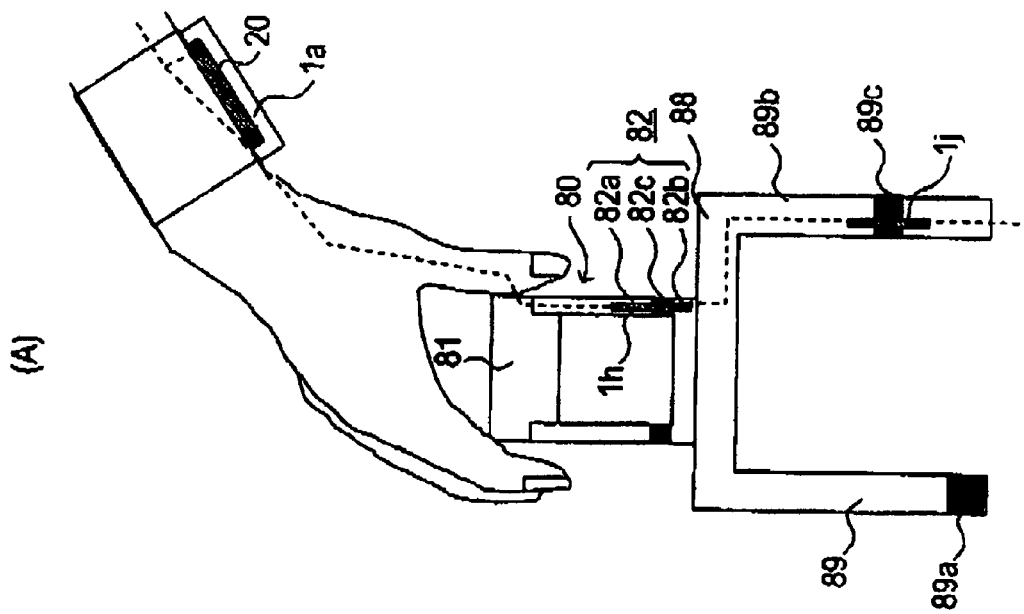
FIG.26

FIG.56
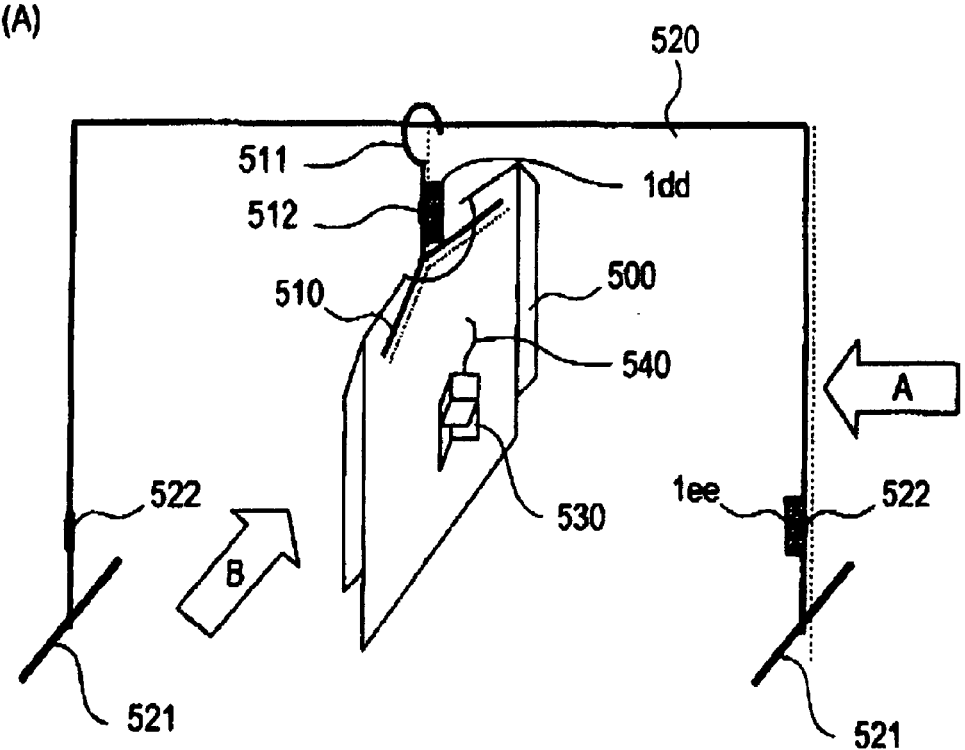
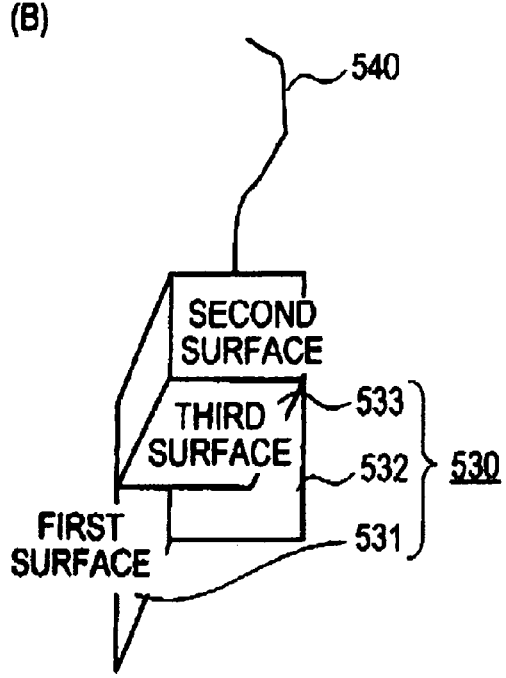
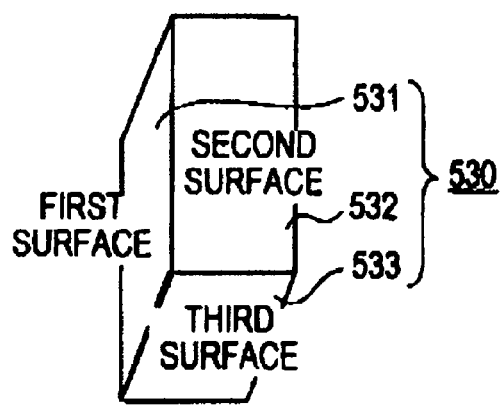

FIG.57
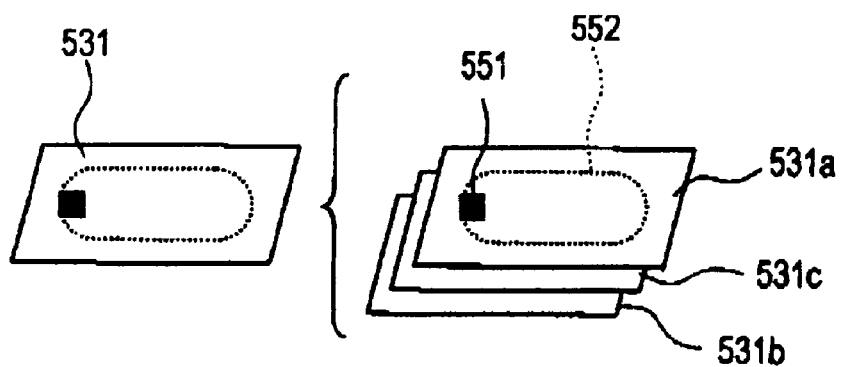
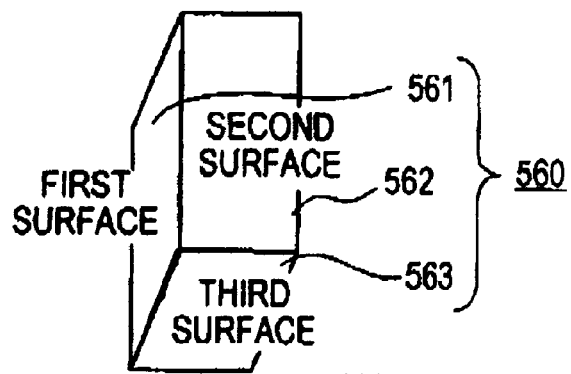
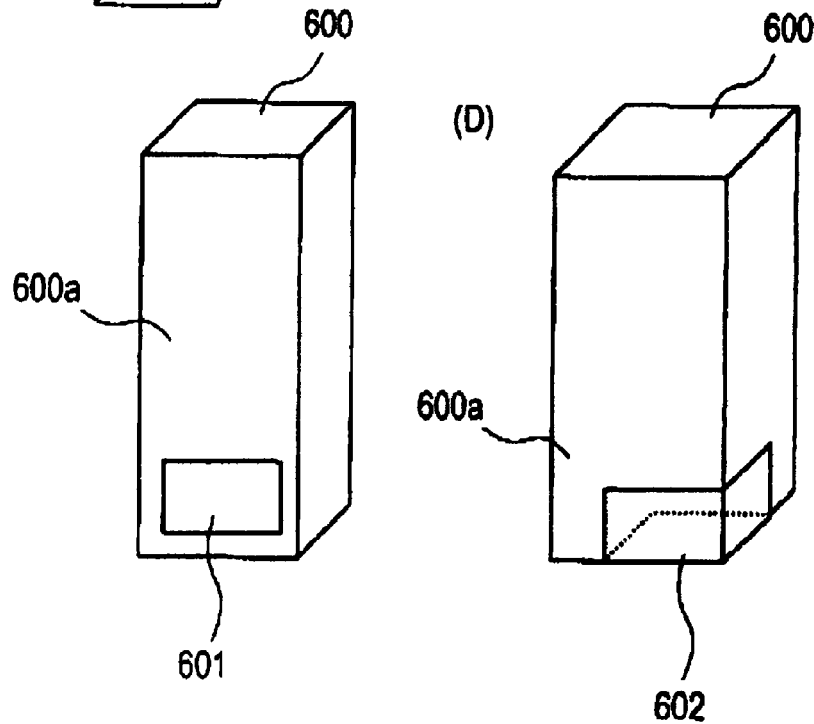

FIG.61
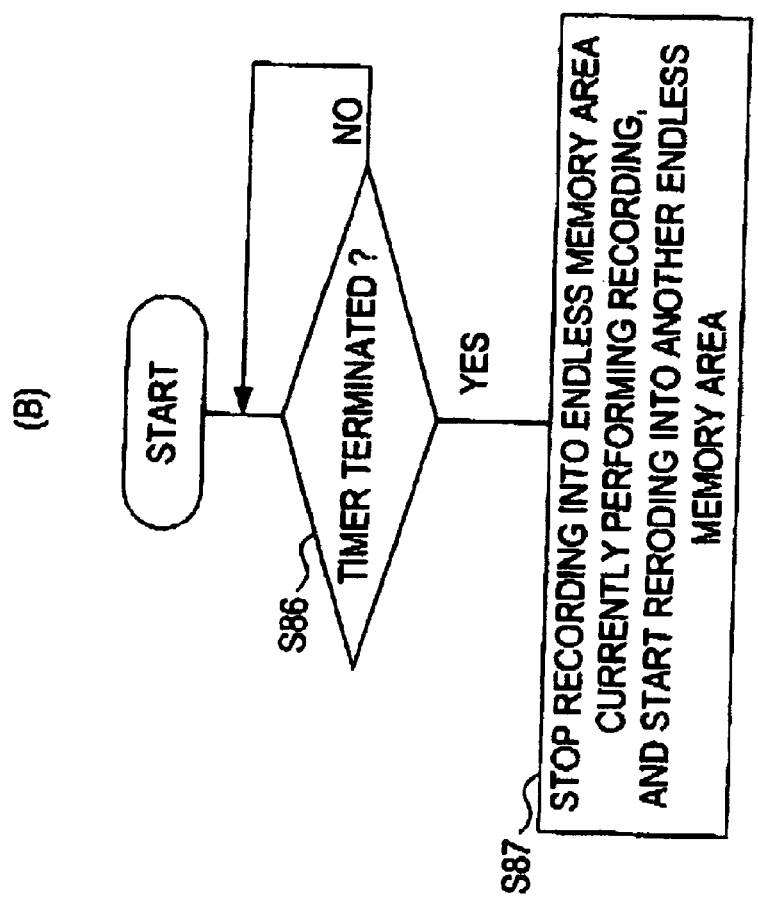
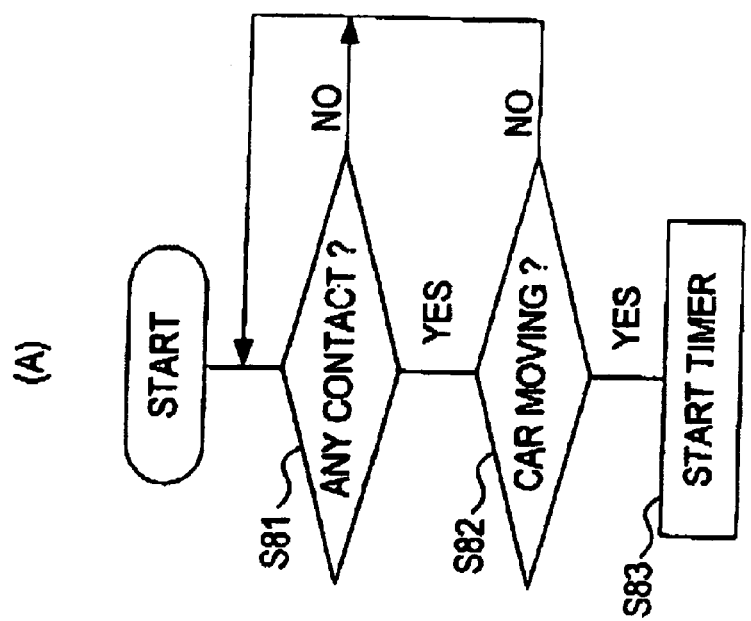

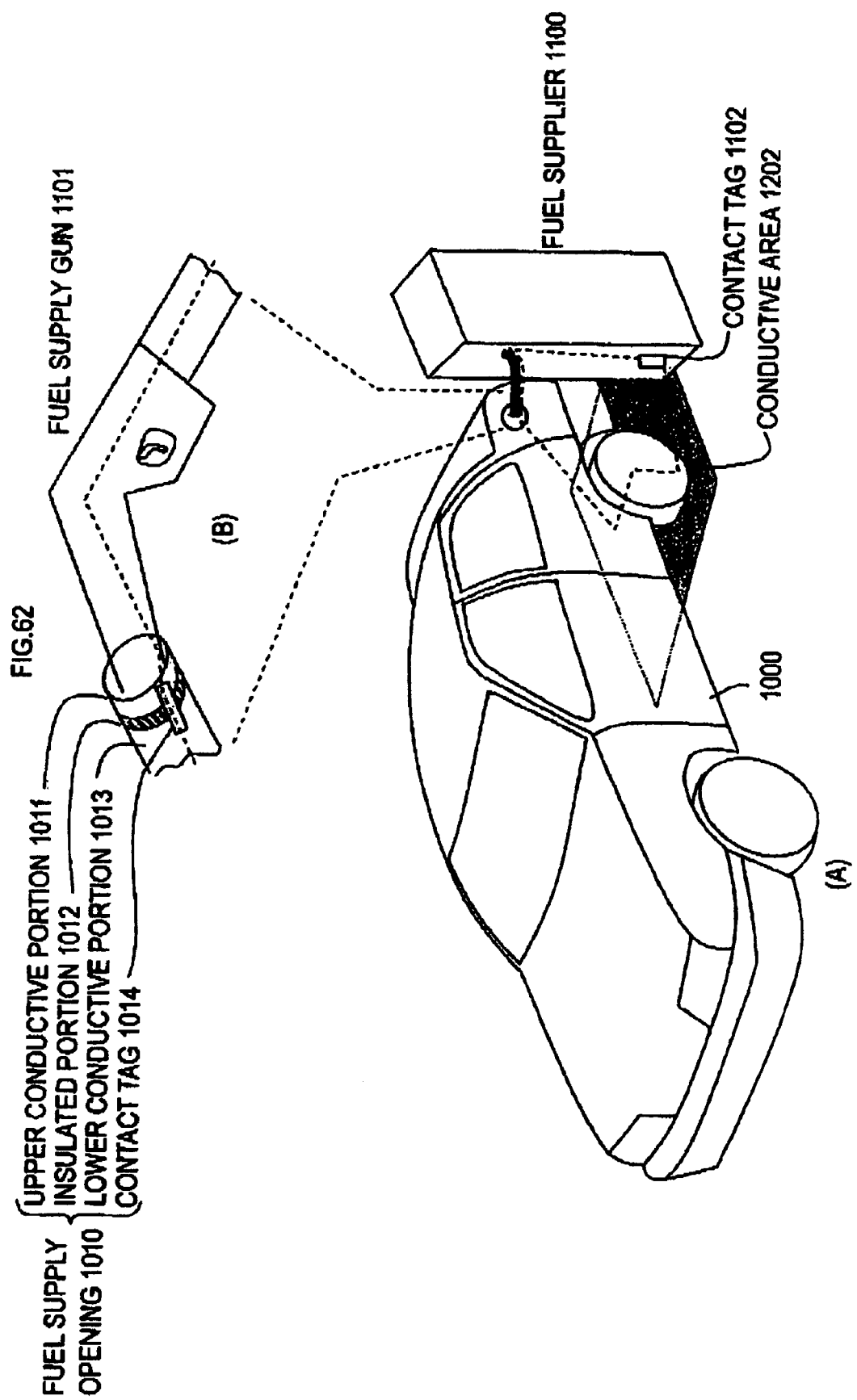

OPERATION STATE DETECTION DEVICE

TECHNICAL FIELD

This invention relates to an operation state detection device for detecting an operation performed by an operator on a person or an object.

BACKGROUND ART

There is a conventional technique in which data communication devices are provided to an object, such as a locking mechanism in a house and to, for example, an arm of a user of the object, and data communication between the data communication devices is performed when the user touches a part (e.g., a door knob) of the locking mechanism and thereby a contact path passing through the user and the locking mechanism is formed. By using a so-called contact communication, it may be possible to achieve an improved security of the locking mechanism (for example, see Patent Documents 1, 2, 3).

Patent Document 1: Japanese Unexamined Patent Application Publication No. 2001-77735
Patent Document 2: Japanese Unexamined Patent Application Publication No. 2001-223649
Patent Document 3: Japanese Unexamined Patent Application Publication No. 2002-246987

DISCLOSURE OF THE INVENTION

Problems to be Solved by the Invention

However, no specific application field has been established by now regarding the above contact communication, except for applying the technique to user identification thereby to improve security. In the meantime, human errors in the medical field, such as misidentification of patients and misidentification of medicines, often cause fatal accidents, and have been serious social problems. Occurrence of human errors leads to profit reduction also in the manufacturing and commercial fields.

The applicant of the present invention focused on the fact that contact communication, which can be performed only when an actual contact exists, is extremely convenient to detect an operation performed by an operator on a person or an object, in comparison with, for example, wireless communication through a wireless tag. Detection of an operation as above may not only be applied to avoid occurrence of human errors, but also be applied for various other purposes. Accordingly, the present invention has been made for the purpose of providing an operation state detection device capable of efficiently detecting an operation performed by an operator on a person or an object.

Means to Solve the Problems

The present invention made to attain the above purpose provides an operation state detection device which includes: data communication devices that are respectively attached to an operator, and a person or an object as an operation target and mutually perform data communication when the operator contacts the person or the object and thereby a path is formed through the operator, and the person or the object; and a detection device that detects the data communication performed between the data communication devices.

According to the present invention configured as above, data communication devices are respectively attached to the operator, and the person or the object as the operation target. These data communication devices mutually perform data communication when the operator contacts the person or the object and thereby a path is formed through the operator, and the person or the object. Then, the detection device detects data communication performed between the data communication devices. Accordingly, it may be possible to extremely accurately determine which person or object the operator has contacted based on the data communication detected by the detection device.

A technique to determine approximate positions of an operator, and a person or an object by using a wireless tag or the like has been being established. In this case, however, it is difficult to identify which object the operator contacts (or operates on), for example, when different objects are arranged side by side. In contrast, according to the present invention in which an operation state of an operator is detected by using so-called contact communication that is not performed unless an actual contact is made, it may be possible to extremely effectively detect an operation on a person or an object performed by the operator.

The path mentioned above is not necessarily limited to a path through which an electric current constantly flows, but may be, for example, an electrostatic coupling-type path including a floor or the earth as a common earth electrode. Also, a contact path for performing contact communication is not limited to a closed circuit as above, and, for example, a so-called waveguide-type human body communication may be applied.

Data detected by the detection device may be used in various forms, such as the following: In one form, a first warning device is further provided to give a warning when a combination of the operator, and the person or the object corresponding to data communication detected by the detection device does not coincide with a specified combination.

According to the present invention, a state of contact between the operator, and the person or the object as the operation target may effectively be detected as described above, and thus it may be possible to effectively monitor whether or not the operator has mistaken the person or the object based on the detected information. Accordingly, the first warning device compares the combination of the operator, and the person or the object corresponding to the data communication detected by the detection device with the specified combination, and gives a warning when the combinations do not coincide with each other. Thus, occurrence of a human error, such as the operator mistaking the person or the object, may effectively be avoided.

The combination of the operator, and the person or the object need not have a one-to-one relationship between an operator and a person or between an operator and an object. Specifically, for example, the combination may be a combination of three or more elements, such as a combination of an operator, a person as an operation target and an object as an operation target, or a combination of an operator and a plurality of objects as operation targets.

Also, data detected by the detection device may be used as the following: In another form, a second warning device is further provided to give a warning when the person or the object corresponding to the data communication detected by the detection device includes a confusing person or object.

It may be possible to list some cases in which a human error is likely to occur. For example, more attention should be paid, previously anticipating occurrence of a human error, to a case of mistaking an agent, taxotere (Japanese Trademark Registration 2690614), for an agent, taxol (Japanese Trademark Registration 3368432), or to a case of mistaking a person named Jiro SUZUKI for a person named Jiro SUZUKI including a different Chinese character. Accordingly, the second warning device gives a warning when a person or an object corresponding to the data communication detected by the detection device includes a confusing person or object. Thus, occurrence of a human error, such as the operator mistaking the person or the object, may effectively be avoided also in this case.

When a clock device that clocks time is further provided, and the detection device detects the data communication performed between the data communication devices together with the time of the data communication, the following additional effect will be brought about. Specifically, since a time when the operator contacts the person or the object may be specified, when the operator makes sequential contacts with a plurality of persons or objects, an order and time intervals of the contacts may easily be specified. Accordingly, various processings, such as avoiding occurrence of a human error based on the detected data, may be performed further accurately.

Furthermore, when a position detection device that detects a position of the operator, the person or the object via wireless communication is further provided, and the detection device detects the data communication performed between the data communication devices together with a position of the data communication, the following additional effect will be brought about. Specifically, a position where the operator contacts the person or the object may also be specified. Accordingly, various processings, such as avoiding occurrence of a human error based on the detected data, may be performed further accurately.

BRIEF DESCRIPTION OF THE DRAWINGS

FIG. 1 is a side view and a bottom view showing a structure of a contact tag according to the present invention;

FIG. 10 is a front view and a cross sectional view taken by the line A-A showing a structure of a display device in the application example;

FIG. 26 is an explanatory view illustrating a contact path via the tablet bottle;

FIG. 56 is an explanatory view showing a configuration for selling clothes in the application;

FIG. 57 is an explanatory view showing a configuration of a wireless tag in the application;

FIG. 61 is a flowchart showing a process for storing data executed by a storage device of the car when a contact, such as a car bump, occurs; and FIG. 62 is an explanatory view of a gas station using the contact communication.

EXPLANATION OF REFERENCE NUMBERS

Figure 2:
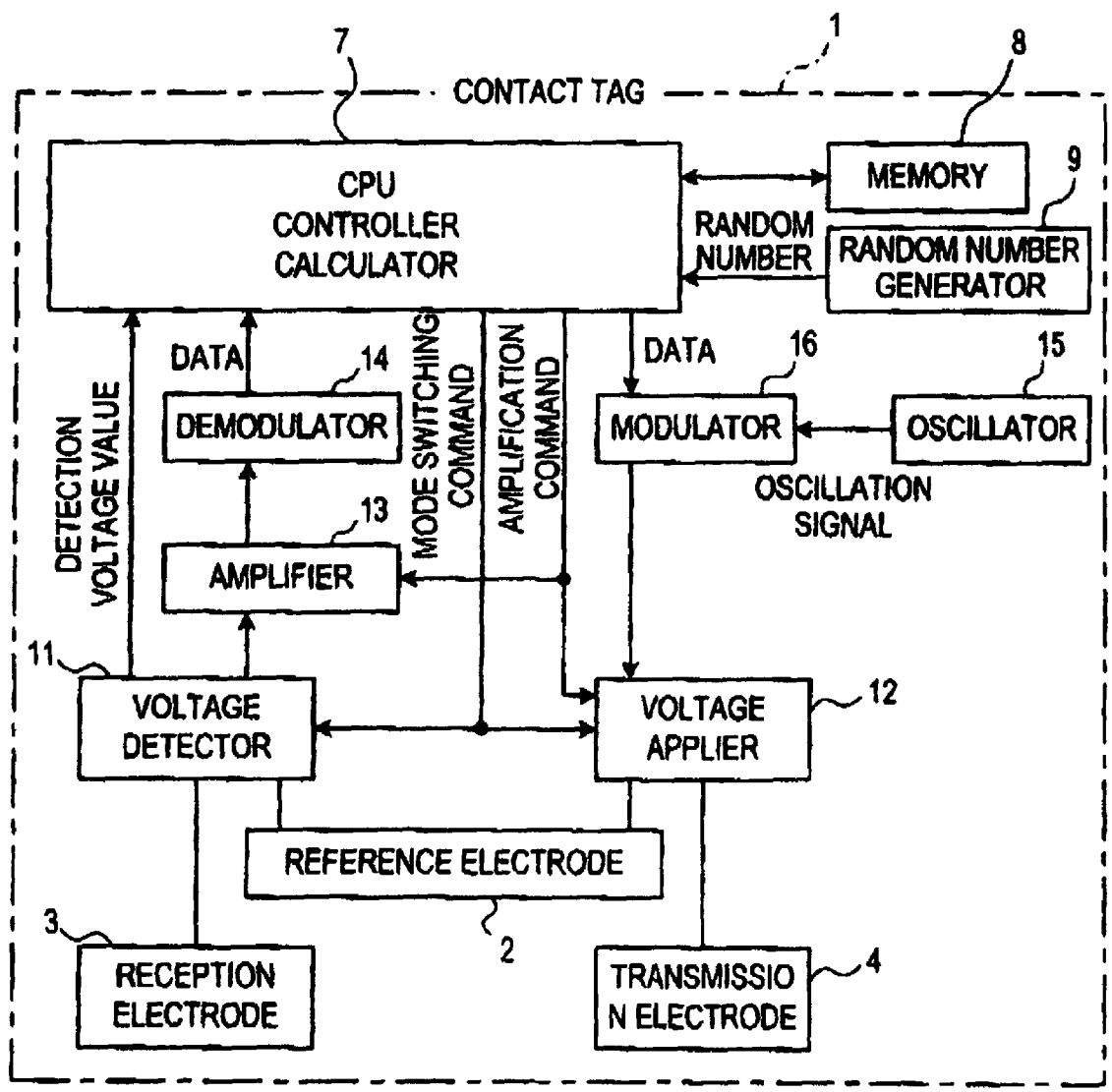
FIG. 2 is a block diagram schematically showing an internal structure of the contact tag.

1 . . . contact tag 20, 40 . . . contact communication device 21 . . . contact tag portion 22 . . . wave clock portion 23 . . . wireless communication portion 25 . . . voice speaker 26 . . . display portion 30 . . . display device 50 . . . injector 55 . . . injector bag 55c, 273, 415, 522 . . . insulating portion 56 . . . injector box 61 . . . wireless station 62 . . . central computer 64 . . . chart computer 70 . . . liquid medicine bottle 80 . . . tablet bottle 85, 260, 450 . . . scale 88 . . . rack 91 . . . intravenous bottle 93 . . . dropper 210 . . . dispensing table 220 . . . prescription computer 230 . . . medicine rack 240 . . . medicine case 250 . . . powdered medicine bottle 270 . . . medicine bag 300 . . . belt conveyor 310 . . . conveyor plate 311, 331 . . . wireless tag receiver 320 . . . refrigerator 322, 422, 465, 530 . . . wireless tag 330 . . . operation booth 340 . . . parts rack 341, 421 . . . rack board 342 . . . conductive plate 344 . . . insulating plate 350 . . . instruction computer 410 . . . shopping cart 420 . . . showcase 500 . . . clothes 510 . . . hanger 520 . . . hanger rack

BEST MODE FOR CARRYING OUT THE INVENTION

Embodiments of the present invention will now be described together with drawings. Firstly, a structure of a contact tag 1 as a data communication device will be explained by way of a side view in FIG. 1(A), a bottom view in FIG. 1(B), and a block diagram in FIG. 2.

Referring to FIGS. 1(A) and (B), the contact tag 1 is formed into a substantially rectangular parallelepiped. A reference electrode 2 is exposedly provided on the under surface of one longitudinal end of the contact tag 1. A reception electrode 3 and a transmission electrode 4 are exposedly provided on the under surface of the other longitudinal end of the contact tag 1. Design change can be made as required depending on application, with respect to the outer shape of the contact tag 1 and the position of exposure of each of the electrodes 2 to 4.

FIG. 2 is a block diagram schematically showing an internal structure of the contact tag 1. The contact tag 1 is provided with a CPU 7 that includes a controller and a calculator therein. The contact tag 1 is also provided with a memory 8 that stores results of calculation by the CPU 7, and a random number generator 9 that generates a random number to be inputted to the CPU 7.

The aforementioned reference electrode 2 and the reception electrode 3 are connected to a voltage detector 11. The reference electrode 2 and the transmission electrode 4 are connected to a voltage applier 12. The voltage detector 11 provides to the CPU 7 a voltage applied to between the reference electrode 2 and the reception electrode 3 as a detection voltage value. Then, the CPU 7 provides an amplification command corresponding to the detection voltage value to an amplifier 13 and the voltage applier 12.

That is, if an impedance of a contact path such as a human body is high (or low), there are cases in which data is unable to be demodulated from the voltage value detected by the voltage detector 11. Therefore, the amplifier 13 is connected to the voltage detector 11 in order to amplify voltage signal detected by the voltage detector 11 based on the amplification command corresponding to the voltage value detected in last few seconds. The amplified voltage signal is demodulated by a demodulator 14, and inputted to the CPU 7 as digital data.

Also, data to be transmitted by contact communication is outputted from the CPU 7. In a modulator 16, the data to be transmitted is modulated with transmission signal generated by a transmitter 15. The modulated data is amplified by the voltage applier 12 to an appropriate value in accordance with, for example the impedance of the contact path as noted above, and applied to between the reference electrode 2 and the transmission electrode 4.

Moreover, the CPU 7 provides a mode switching command to the voltage detector 11 and the voltage applier 12. The mode switching command is a command to switch the operation mode of the contact tag 1 to a transmission mode, a reception mode, or a suspension mode. The transmission mode halts voltage detection in the voltage detector 11. The reception mode halts voltage application in the voltage applier 12. The suspension mode halts the voltage detection in the voltage detector 11 and the voltage application in the voltage applier 12. The CPU 7 outputs the mode switching command, for example as follows, based on the random number inputted from the random generator 9. That is, the mode is switched such that, if the random number inputted from the random generator 9 is divided by, for example three and the remainder is zero (0), the suspension mode is selected. If the remainder is one, the transmission mode is selected. If the remainder is two, the reception mode is selected.

Let us assume that there are plenty of the contact tags 1 on one contact path for contact communication and that contact communication is performed among those contact tags 1. Then, there is a fear that transmission data may be mixed if plural number of the contact tags 1 are in the transmission mode at the same time. However, in the present embodiment, since the mode is switched as such, mixing of data can be avoided in a favorable manner. Furthermore, even if the remainder of the division by three is zero (0), not the suspension mode but the reception mode may be selected. Then, the reception mode may be selected with probability ⅔, and the transmission mode may be selected with probability ⅓. In this manner, improvement in contact communication can be achieved. Because contact communication is difficult if contact communication is performed among a large number of contact tags and the plurality of contact tags perform transmission at the same time. Also, it takes time to complete contact communication since the contact tag in the transmission mode cannot perform reception. To the contrary, if only one of the contact tags is in the transmission mode, all the other contact tags in the reception mode can perform reception. Thus, the contact communication completes all the more quickly. For this reason, it is preferable that the reception mode is given higher probability of being selected than the transmission mode.

Although not shown, each contact tag 1 is provided with power. In case that there is the contact tag 1 that is different in type of power on one contact path, time allocation to each mode (transmission, reception or suspension) may be set as follows. That is, in the contact tag 1 for equipment having external power like AC power, etc. more time is allocated to the transmission mode with large power consumption. In the contact tag 1 of mobile type only having battery, less time is allocated to the transmission mode with large power consumption. Also, in the contact tag 1 of mobile type only having battery, energy saving can be achieved if the reception mode may be selected at normal times and, after data reception, the transmission mode may be selected. The reason why the reception mode saves energy as compared to the transmission mode is because, in the reception mode, it is only necessary to detect voltage from the contact tag on the other end by the reception electrode. Thus, it is not necessary to keep applying voltage for transmission to the transmission electrode at all times.

Also, in the contact tag 1, like Suica used at an automatic ticket gate, which has external power to which electricity is supplied by air only when communication is necessary, it is preferable that the transmission mode and the reception mode may be selected with equal probability. There are various types of external power which use AC power, inductive power like some shavers, and microwave and electromagnetic induction like a wireless tag.

Also, with respect to the contact tag 1 having a plurality of powers (such as external power like AC power, battery, etc.), it is preferable that a power controller is provided which detects the condition of each power, that is, whether or not the power is externally supplied, whether or not the battery power is sufficient, etc., to supply power to the contact tag 1 from the most suitable power. Such a structure allows to change time allocation to each mode (transmission, reception or suspension) depending on which power is in use.

Figure 3:
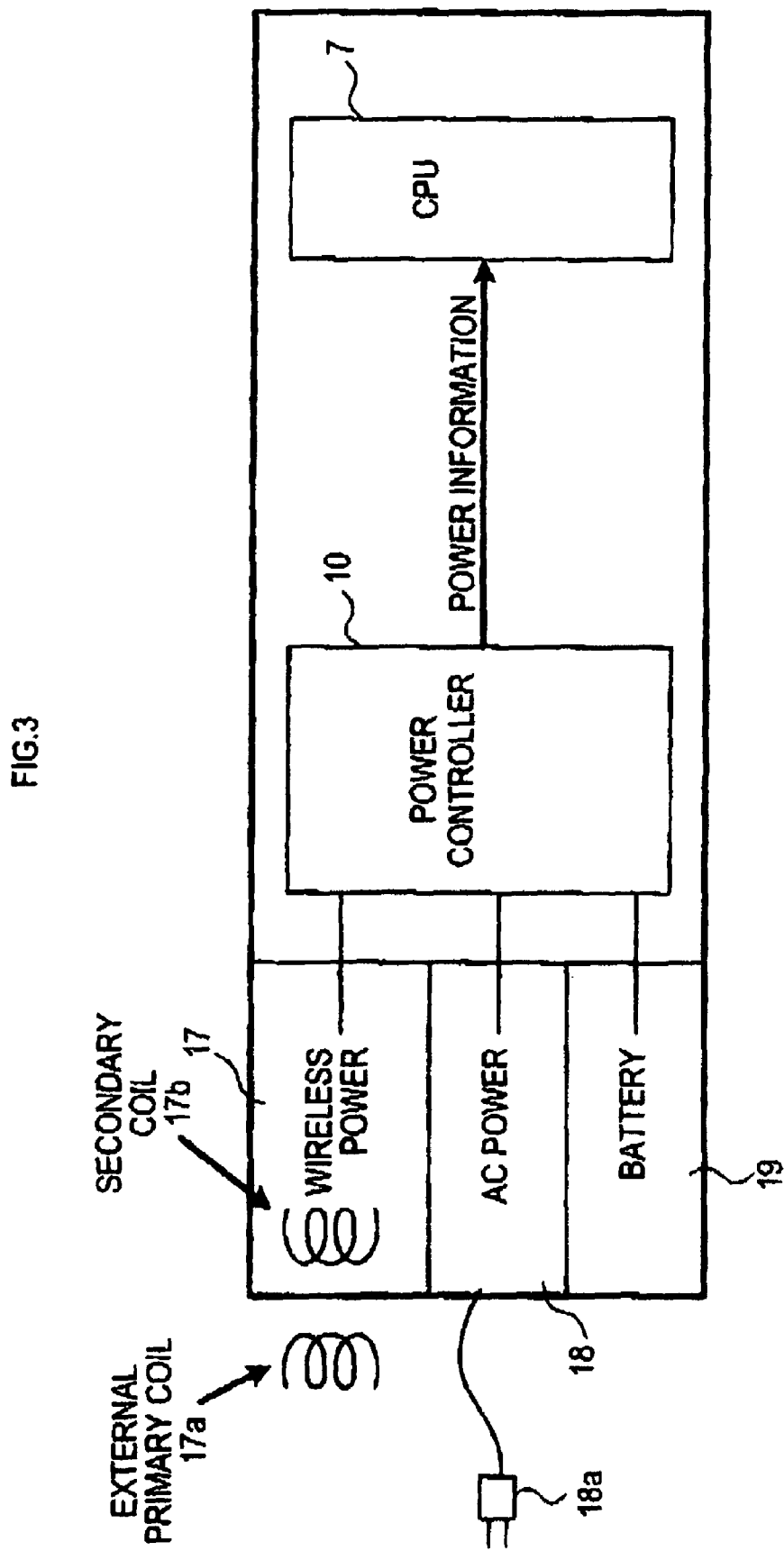
FIG. 3 is a block diagram showing an example of power of the contact tag.

For example, referring to FIG. 3, there are provided a wireless power 17 charged by electromagnetic induction between an external primary coil 17a and an internal secondary coil 17b, an AC power 18 that can be connected to an alternating current of 100V via a plug 18a, and a battery 19. Then, the following control can be conducted by connecting those powers 17 to 19 to a power controller 10 and transmitting power information to the CPU 7.

Figure 4:
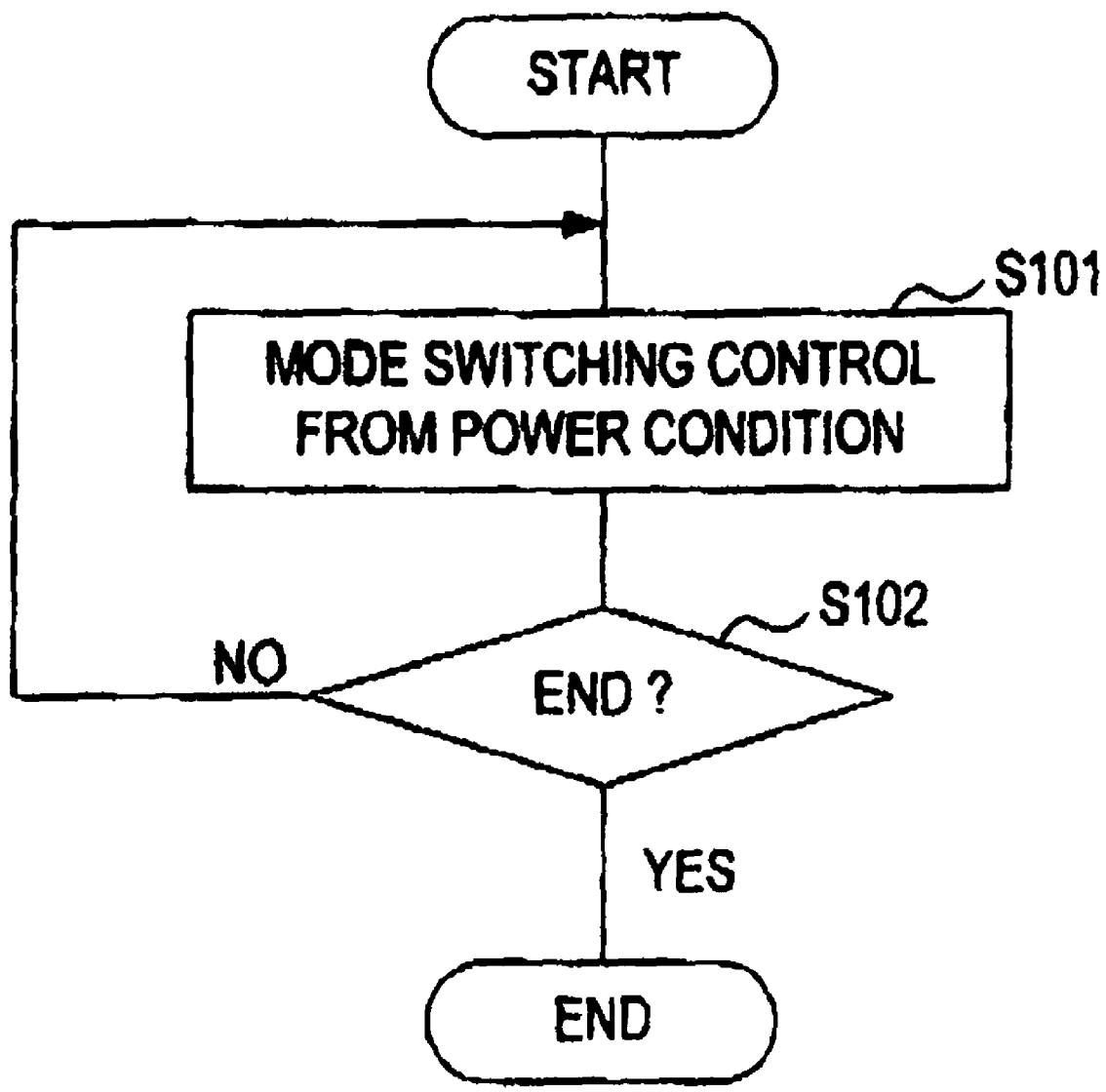
FIG. 4 is a flowchart showing a process relating to the power.

That is, referring to FIG. 4, when a process is started, the CPU 7 changes time allocation to each mode (transmission, reception or suspension) in view of power condition corresponding to the power information transmitted from the power controller 10 in S101 (S represents a step and the same applies hereinbelow). In subsequent S102, it is determined whether the process is END, for example due to power shut down. If not END (S102: NO), the step of S101 is repeated. If END (S102: YES), the process is once ended. This process allows to increase time allocation to power saving modes of reception and suspension in the case of necessity of reduction in power consumption. In the case of sufficient power, time allocation to the transmission mode can be increased.

Figure 5:
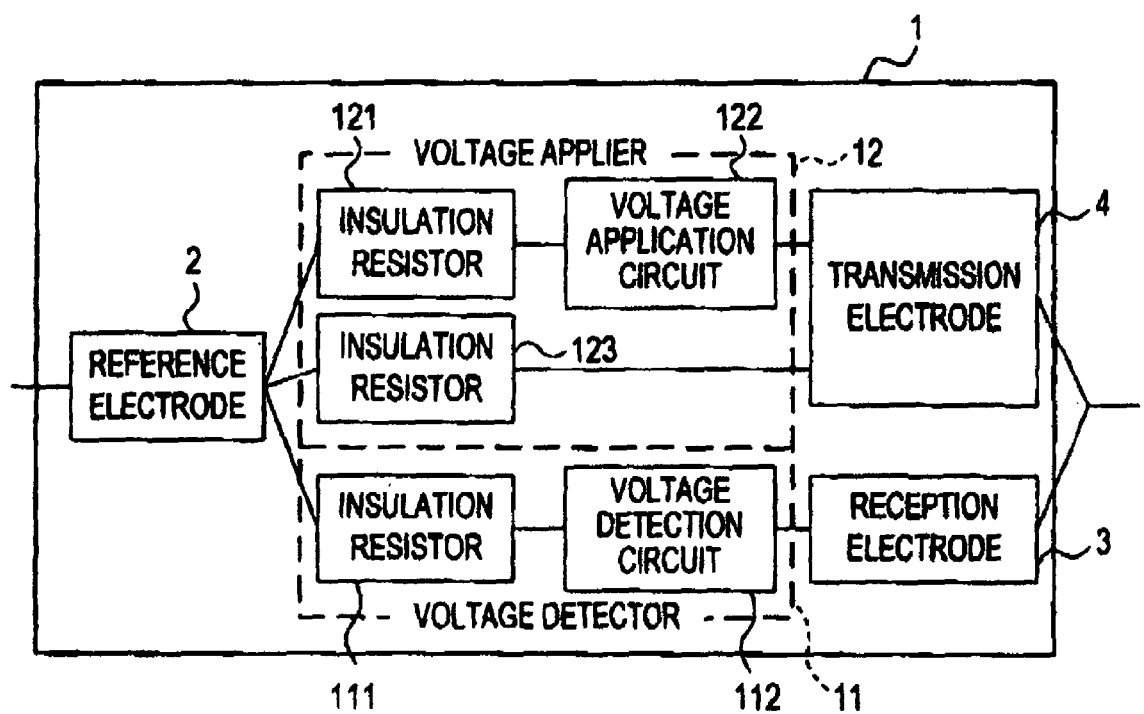
FIG. 5 is a block diagram showing in detail structures of a voltage detector and a voltage applier of the contact tag.

Next, FIG. 5 is a block diagram showing in detail one example of structures of the voltage detector 11 and the voltage applier 12. Referring to FIG. 5, the voltage applier 12 is provided with two paths, i.e., a path connecting the reference electrode 2 and the transmission electrode 4 via an insulation resistor 121 and a voltage application path 122, and a path connecting the reference electrode 2 and the transmission electrode 4 via an insulation resistor 123. On the other hand, the voltage detector 11 is provided with only one path connecting the reference electrode 2 and the reception electrode 3 via an insulation resistor 111 and a voltage detection path 112. As below, only one of the total of three paths is activated in accordance with the aforementioned mode.

Figure 6:
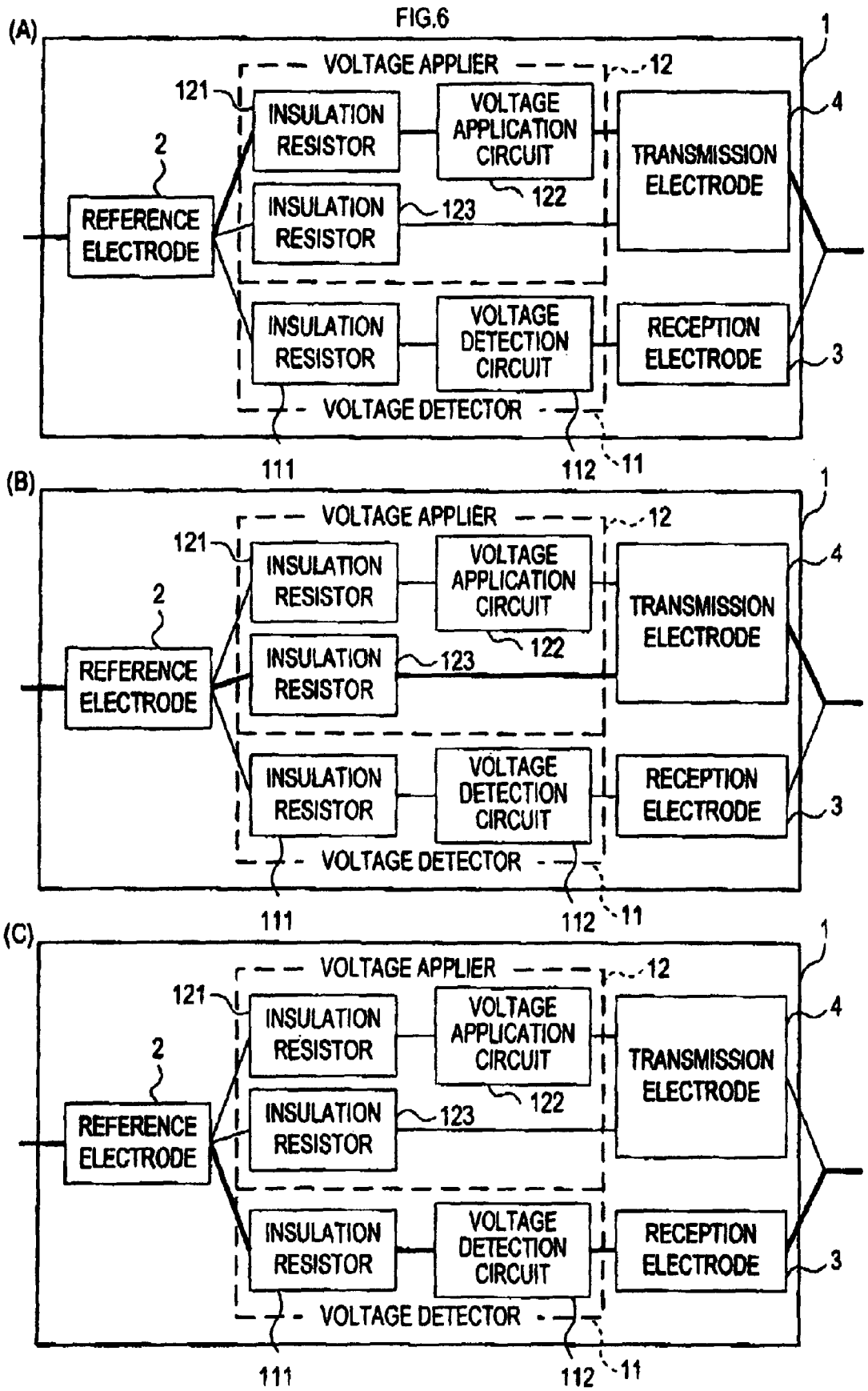
FIG. 6 is an explanatory view showing operation of the control tag.

In the transmission mode, as shown in FIG. 6(A), only the insulation resistor 121 is turned ON and the other insulation resistors are turned OFF. In this manner, only the path connecting the reference electrode 2 and the transmission electrode 4 via the insulation resistor 121 and the voltage application path 122 is activated. In FIG. 6, the activated path is shown by heavy line. As a result, voltage can be applied to between the reference electrode 2 and the transmission electrode 4 by the voltage application path 122.

In the suspension mode, as shown in FIG. 6(B), only the insulation resistor 123 is turned ON and the other insulation resistors are turned OFF. In this manner, only the path connecting the reference electrode 2 and the transmission electrode 4 via the insulation resistor 123 is activated. As a result, the contact tag 1 can be essentially equated with the insulation resistor 123. Data flowing through the contact path can be passed straight through. In this manner, for example, even if one out of three contact tags performing contact communication on one contact path is in the suspension mode, there is no interruption of the contact path between the other two of the contact tags.

Moreover, in the reception mode, as shown in FIG. 6(C), only the insulation resistor 111 is turned ON and the other insulation resistors are turned OFF. In this manner, only the path connecting the reference electrode 2 and the reception electrode 3 via the insulation resistor 111 and the voltage detection path 112 is activated. As a result, voltage applied to between the reference electrode 2 and the reception electrode 3 can be detected by the voltage detection path 112.

Figure 7:
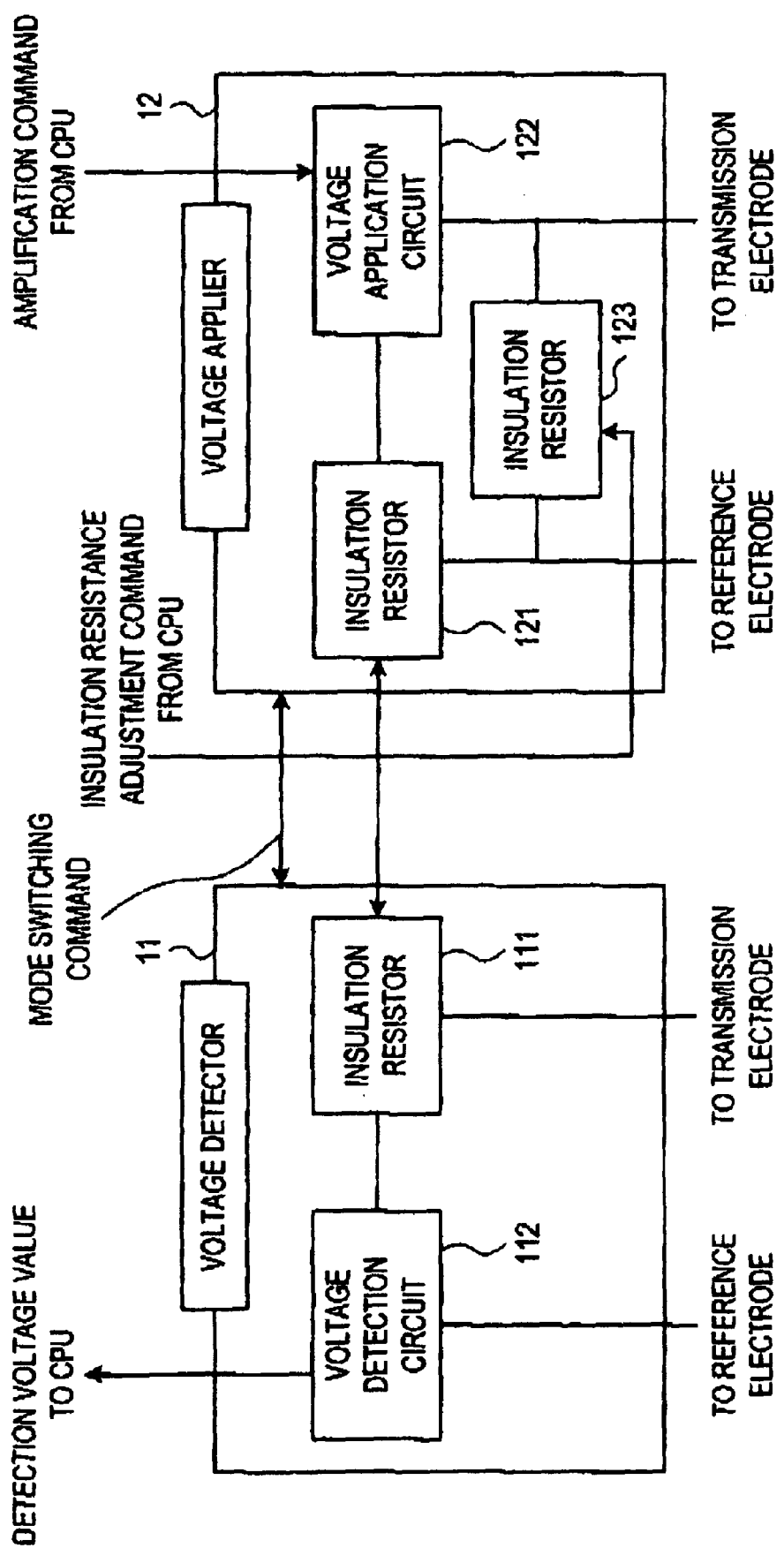
FIG. 7 is an explanatory view showing the operation of the control tag in relation to a CPU.
Figure 8:
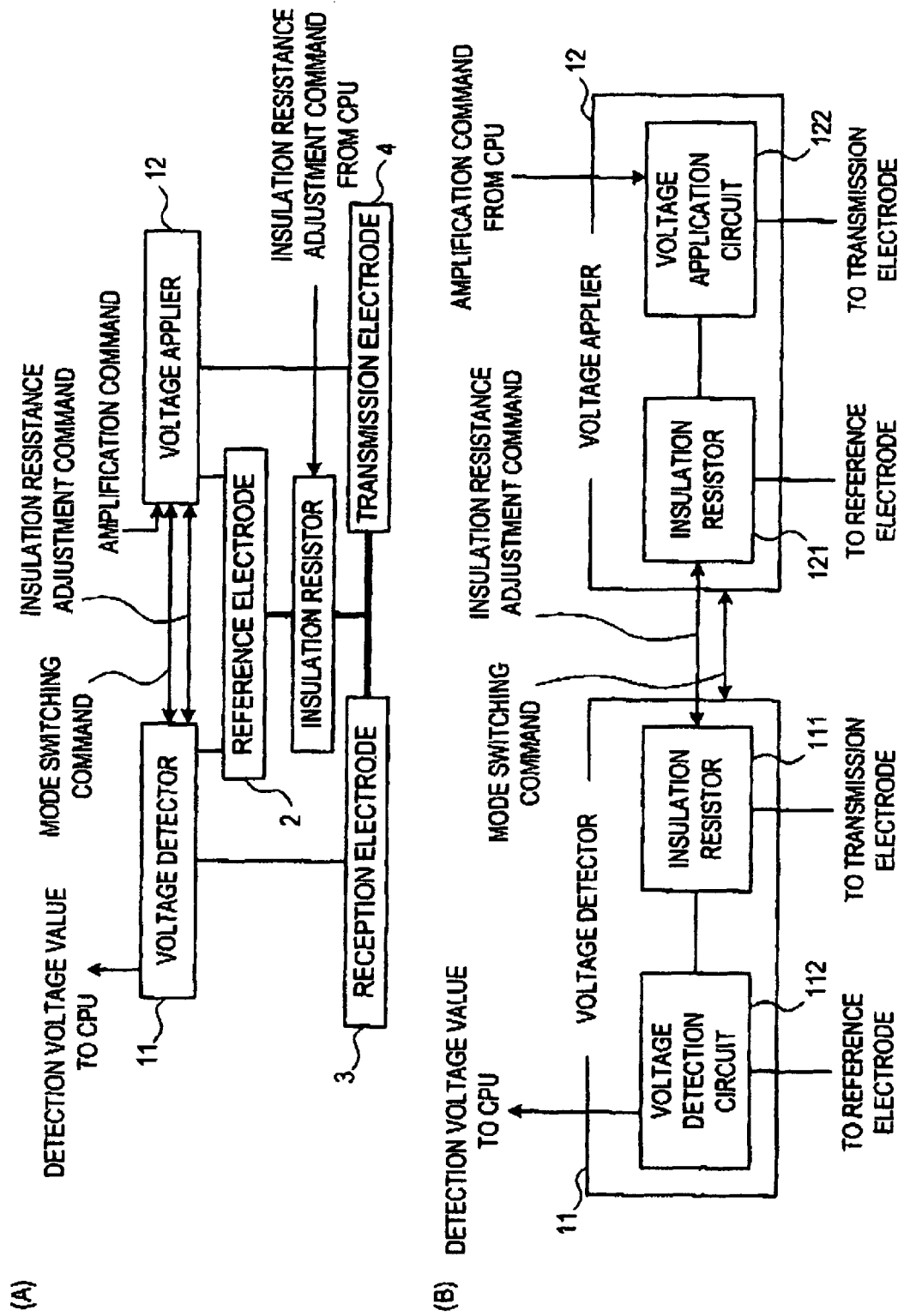
FIG. 8 is a block diagram showing other structure examples of the voltage detector and the voltage applier of the contact tag.

In the contact tag 1, the aforementioned mode is switched as such. Accordingly, the mode switching command inputted from the CPU 7 to the voltage detector 11 and the voltage applier 12 is, as shown in FIG. 7, an insulation resistance adjustment command from the CPU 7 to the insulation resistors 111, 121 and 123. In the transmission mode or the reception mode as well, a bypass path may be created by turning ON the insulation resistor 123 to adjust a resistance value of the insulation resistor 123. Moreover, a bypass path may be provided in the voltage detector 11, in both the voltage detector 11 and the voltage applier 12, or anywhere. For example, a bypass path as shown by heavy line in FIG. 8(A) may be provided. In this case, the mode switching command or the insulation resistance adjustment command from the CPU is inputted as shown in FIG. 8(B).

The present embodiment is one example of structures of the voltage detector 11 and the voltage applier 12. To be more simple, the insulation resistor 121, the insulation resistor 123, and the insulation resistor 111 may not be provided. In this case, the voltage application path 122 is directly connected to the reference electrode 2 and the transmission electrode. The voltage detection path 112 is also directly connected to the reference electrode 2 and the transmission electrode. Also, in this case, if the suspension mode is selected, it is preferable that insulation of the contact path due to insulation of the contact tag does not prevent the other contact tags from performing contact communication. For this purpose, a path may be provided which is not insulated even in the suspension mode as in FIG. 6(B). Or, the insulation resistance value of paint and the like on the surface of the contact tag between the reference electrode and the transmission/reception electrode may be adjusted so that the contact tag has conductivity sufficient for not preventing transmission/reception of contact communication of the contact tag of its own. Also, the voltage application path 122 and the voltage detection path 112 may be designed so as not to be insulated even in the suspension mode.

Figure 32:
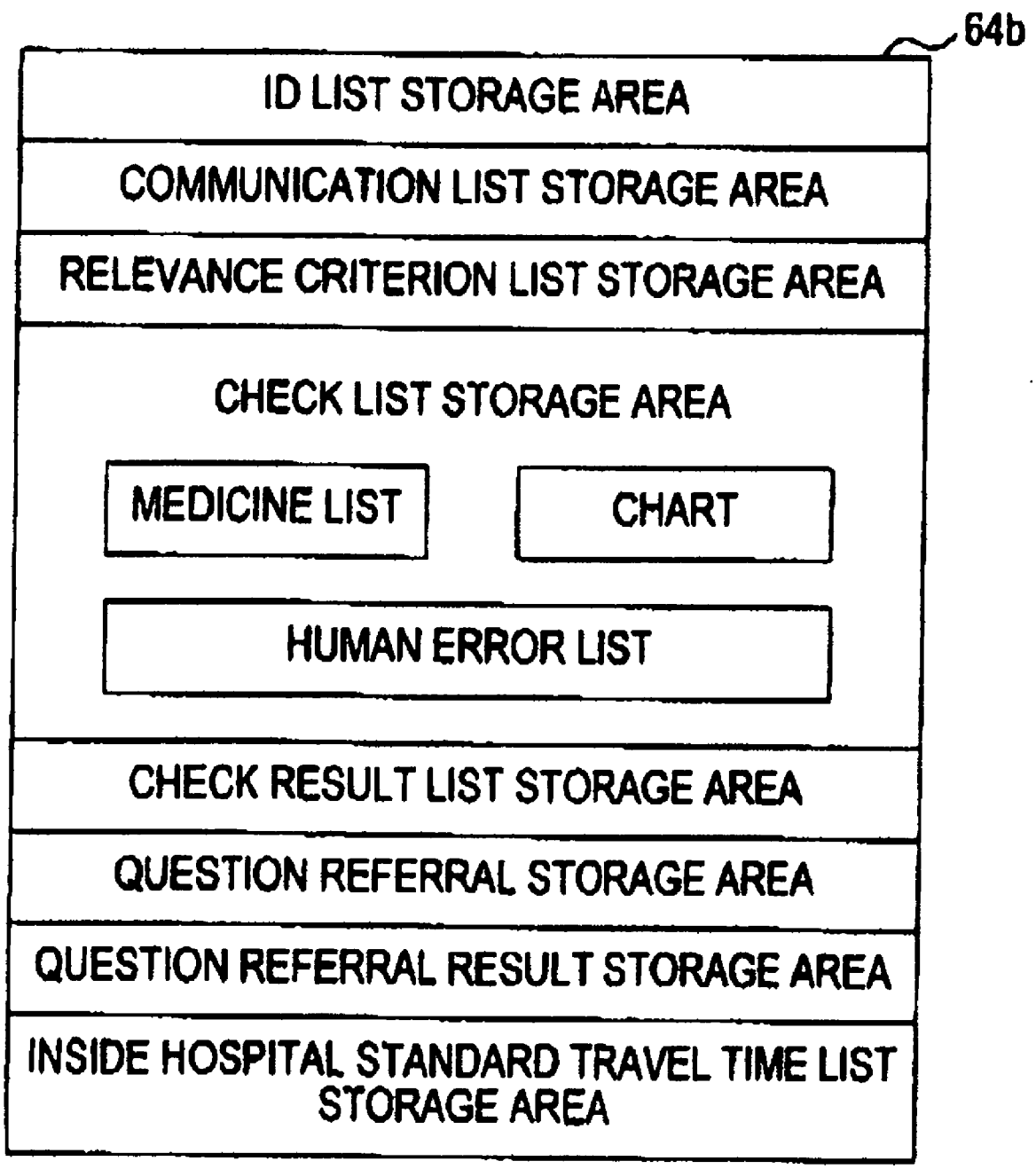
FIG. 32 is a block diagram showing a structure of memory of the aforementioned chart computer.
Figure 33:
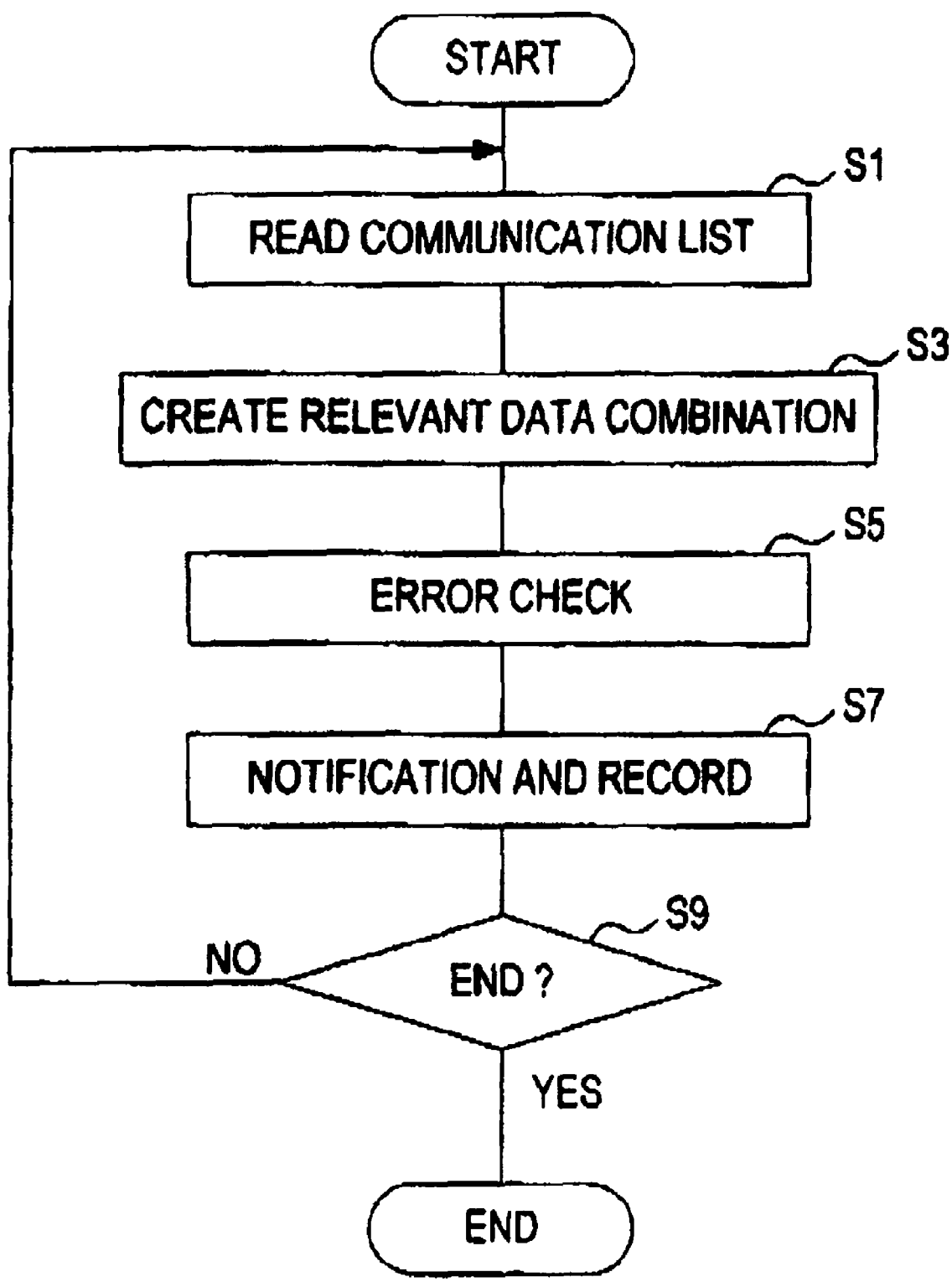
FIG. 33 is a flowchart showing a human error check process executed by a CPU of the aforementioned chart computer.
Figure 34:
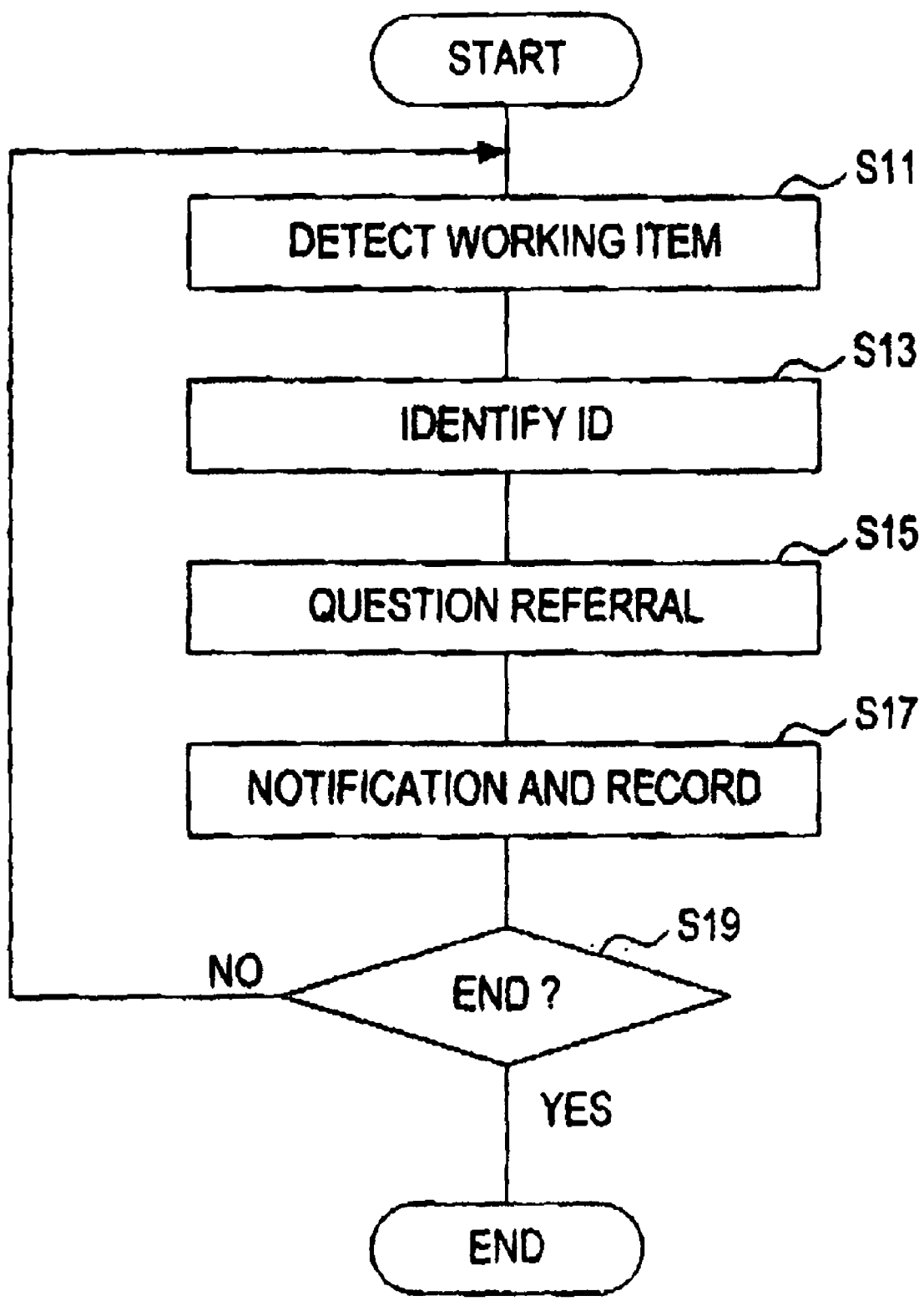
FIG. 34 is a flowchart showing a question referral process executed by the CPU.

The memory 8 of the contact tag 1 stores an ID of its own, and also stores the following information in storage areas as shown in FIG. 32. The stored information is used in later explained processes (FIG. 33 and FIG. 34). The stored information will be described below. Also, a chart computer 64, replacing paper chart, is a computer on which a doctor keeps records at the time of medical examination. This is also a type of contact communication device provided with the contact tag 1. A CPU 64a is provided with a function of the CPU 7 of the contact tag 1 as well. A memory 64b is provided with a function of the memory 8 of the contact tag 1 as well.

An ID list storage area: This area stores an ID list in which an ID is associated with what is represented by the ID. Referring to this ID list, what is indicated by the ID received by communication and in what state can be specified.

For example, an ID of a contact tag 1a or 1b of a contact communication device 20 or 40 stores a name of a doctor, a nurse, or a patient who uses the contact communication device 20 or 40. An ID of a contact tag 1f of a liquid medicine bottle 70 stores various information, for example the preserved form and the name of the content of the liquid medicine bottle 70 such as "liquid medicine bottle 70", "xylocaine 10%", etc., the purpose of use of the liquid medicine such as injection, intravenous drip, etc., a flag indicating the state such as opened and not opened of the liquid medicine bottle 70 detected as above. In the case of articles like the liquid medicine bottle 70 of which ID has many representations, explanation will be given in a simple manner like the liquid medicine bottle 70 or the liquid medicine bottle (opened) 70.

A communication list storage area: This area stores a communication list containing communication records by the contact communication device of its own. For example, in an example of FIG. 15, the following communication items are stored in a communication list of a nurse A:

1. contact reception flag, reception time, ID of injector C;
2. contact reception flag, reception time, ID of injector box D;
3. contact reception flag, reception time, ID of rack E; and
4. contact transmission flag, time, ID of nurse A.

Also, other than the communication list containing communication records by the contact tag 1 of its own, communication lists of the other contact tags 1 may be stored. In this case, when the contact tag communicates with the other tags 1 or a central computer by contact communication, a wireless LAN or a wired LAN, the contact tag 1 transmits the communication list of its own and receives the communication lists of the other contact tags 1. In this manner, the communication lists of the other contact tags 1 are obtained.

A relevance criterion list storage area: This area stores a relevance criterion list as relevance criteria. The relevance criteria are used to determine in what cases each of transmission/reception data in the communication list has strong relevance to each other. The list is used to analyze the communication list. For example, the followings are an example of the criteria to determine strong relevance:

(1) data in simultaneous contact;

(2) contact data of contact communication in less than five minutes; and (3) in case that there are more than two identical data among a plurality of relevant data combinations taken out as strong relevance.

The data in simultaneous contact in (1) is data in the communication list obtained by contact communication though one time contact of when in contact until when out of contact. For example, in the communication list of the nurse A on the left side of FIG. 30(B), after there is a contact end at the item 5 in FIG. 30(A), there is another contact end at the item 8 on the left side of FIG. 30(B). Thereby, the items 6 to 7 on the left side of FIG. 30(B) are found to be within one time contact communication. Simultaneous contact is considered as a contact from when in contact until when out of contact, although there is some time lag to be exact. As above, considering a contact end FG in the communication list as a separator, a contact from when in contact until when out of contact can be treated as one time simultaneous contact.

With respect to the relevance criteria, high relevance may be determined when all the above conditions (1) to (3) are satisfied. Or, high relevance may be determined when at least one of the above conditions is satisfied.

A check list storage area: This area stores a medicine list, a chart, and a human error list explained below as check lists to determine whether there is any medical error.

The medicine list: stores basic information on medicine, for example restriction of use (dose and the number of dose) per medicine and contraindication (avoidance of taking the medicine with other medicines) such as of anticancer medicine. The medicine list stores such information as OK keyword combination or NG keyword combination. Examples of OK keyword combination are xylocaine 2% and injection, xylocaine 10% and intravenous drip, etc. Examples of NO keyword combination are xylocaine 2% and intravenous drip, xylocaine 10% and injection, etc.

The chart: stores medical treatment and procedures to be performed per patient. The chart is provided with fields to store detailed data of the treatment actually done. Moreover, when, for example a nurse performs some medical treatment, contact paths are generated between the contact communication device 20 born by the nurse and an injector held by the nurse, etc. to perform contact communication. The medical treatment content, instantaneous time when the medical services have been actually performed, etc. are precisely stored in the chart of the contact communication device 20 of the nurse.

For example, the chart stores various medical treatment methods such as intravenous drip, injection, how to take medicine, prescription of medicine, etc. and courses in the past (pathology and treatment). The chart is provided with fields to enter an ID of a medical staff who performed each treatment, time, etc. Each information is stored in the corresponding field. Accordingly, the time of treatment and the time when the medicine has been taken are also stored. Moreover, since medical treatment is performed based on the chart, the data stored in the chart is used to determine whether the medical services to be performed conform to the chart in a later explained process.

The human error list: stores OK keyword combination and NG keyword combination to check cases in which human error is likely to occur. This human error list is a list that allows to check human error which may not be able to be checked by the medicine list and the chart. The description form of this list is the same as the medicine list. Keyword combinations which may cause human error are listed as NG keyword combination. Also, keyword combinations which are within the bounds of normal behavior are listed as OK keyword combination.

A check result list storage area: stores keywords at the time when warning is given by a later explained human error check process as a check result list.

A question referral list storage area: stores keywords for cases that require confirmation on whether or not there is an error as a question referral list. The cases are detected which are not determined as error but with high probability of error (question). The keywords for these mistakable cases are stored in the present list by automatic extraction of misleading combination such as approximate words from the check lists, etc., or by human input.

For example, other than the aforementioned "xylocaine 2%" for injection and "xylocaine 10%" for intravenous drip, approximate words like "Theolong" and "Theodur", and "Taxotere" and "Taxol" of medicine, and "SUZUKI Ji(Ni)ro*" and "SUZUKI Ji(Ji)ro*" of patient names, and mistakable behavior are stored as keyword combination. [*homophones including different Chinese characters difference is artificially added for distinction as a matter of convenience]

A question referral result list storage area: stores keywords at the time when warning is given by a later explained question referral process as a question referral result list.

An inside hospital standard travel time list storage area: stores standard human travel time between hospital rooms as an inside hospital standard travel time list.

Figure 9:
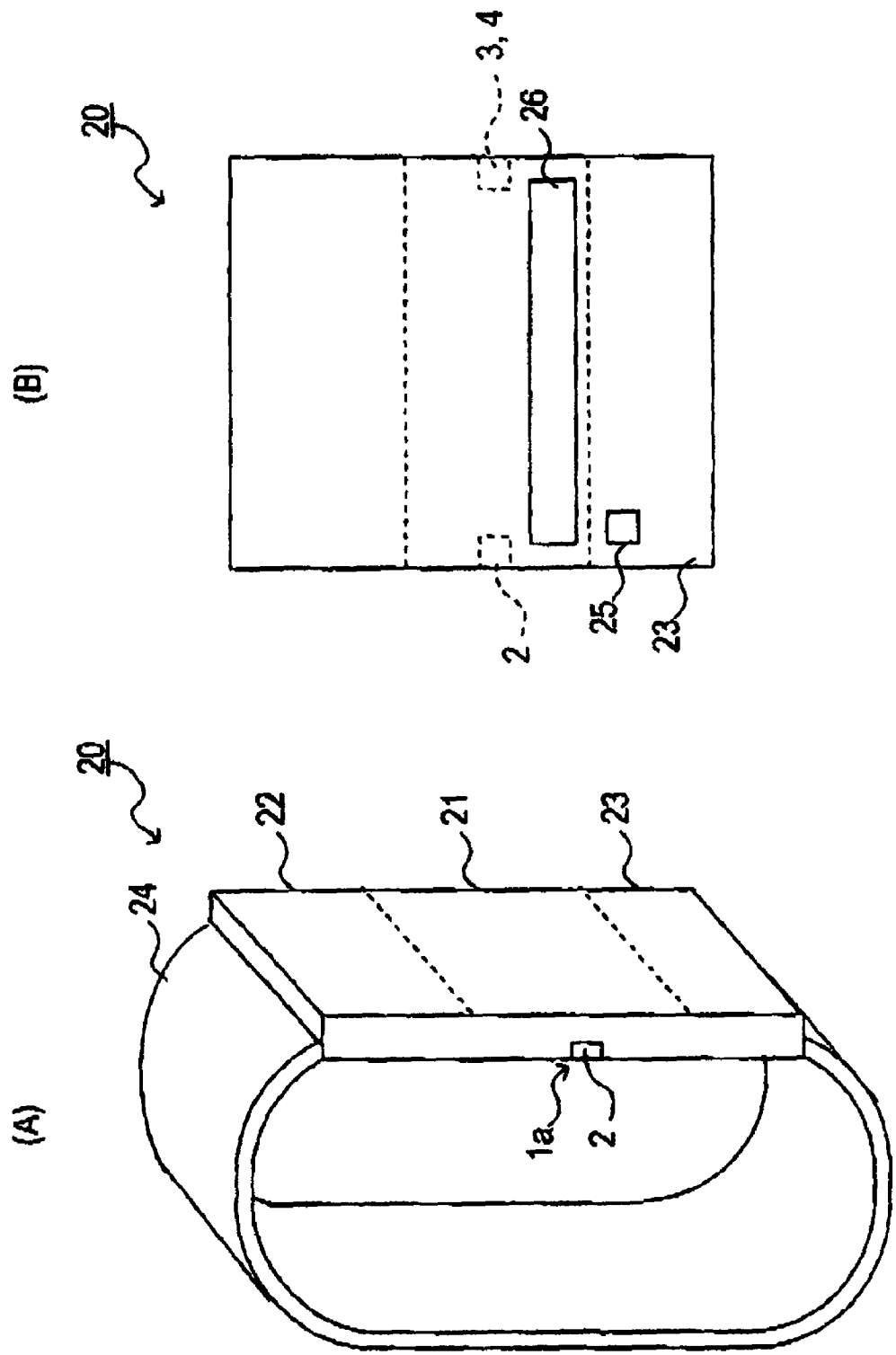
FIG. 9 is a perspective view and a front view showing a structure of a contact communication device in an application example of the present invention to medical services.

Next, explanation is given on an application example of the above structured contact tag 1 to prevention of human error in medical services. In the present embodiment, a nurse bears the contact communication device 20 shown in FIG. 9 on the dominant arm (hereinafter, referred to as the right arm but could be a reverse of left and right), and a display device 30 shown in FIG. 10 on the left arm. A patient bears the contact communication device 40 shown in FIG. 11 on the arm which mainly receives injection and intravenous drip.

FIG. 9(A) is a perspective view showing an overall structure of the contact communication device 20. FIG. 9(B) is a front view showing a structure of the main portions. The contact communication device 20 includes a contact tag portion 21, a wave clock portion 22, and a wireless communication portion 23. The contact tag portion 21 incorporates the contact tag 1 (hereinafter, a suffix 'a' is attached for distinction from the other contact tags 1; later explained other contact tags 1 will be also accompanied by a suffix for distinction) therein. The wave clock portion 22 (corresponding to a time device) incorporates a known wave clock therein. The wireless communication portion 23 performs wireless communication with an inside hospital LAN 60 (see FIG. 17). The contact communication device 20 further includes a band 24 for securing the above portions to the nurse's arm. Each of the electrode 2 to 4 of the contact tag 1a provided in the contact tag portion 21 is exposedly positioned so as to allow close contact to the nurse's arm. On the surface of the wireless communication portion 23, a voice speaker 25 is provided which notifies completion of transmission/reception. On the surface of the contact tag portion 21, a display portion 26 is provided which displays communication content, etc. Also, the band 24 is composed of insulating material.

FIG. 10(A) is a front view showing a structure of main portions of the display device 30, which is one type of contact communication device. FIG. 10(B) is a cross sectional view taken by the line A-A. In FIG. 10(B), conductive portions are shown by heavy line. This display device 30 may be born on the arm via an insulating band 31 as shown in later explained FIG. 23, or may be held by hand without the band 31. For example, as in FIG. 24(B), a left grip portion 32 and a right grip portion 33 provided on both ends of the display device 30 are electrically conducted through a contact path passing through the contact communication device 20, for example as a result of gripping of the left hand grip portion 32 and the right hand grip portion 33 by a nurse. Then, contact communication is performed between the contact communication device 20 and the display device 30. Thereby, information based on data, etc. stored in the contact communication device 20 is displayed on a display portion 34 on the surface. Also, the surface of the display portion 34 is composed of conductive material electrically conducted to the right hand grip portion 33. Therefore, in order to avoid short circuit by touch of the hand gripping the left hand grip portion 32 to the display portion 34, an insulating protrusion 35 is formed between the display portion 34 and the left hand grip portion 32.

A nurse normally performs injection and takes out medicine by the dominant arm. Thus, a contact path is likely to be formed by the dominant arm. Accordingly, it is preferable that the contact communication device 20 is born on the dominant arm. Also, in the case of bearing the display device 30, bearing the display device 30 on the non-dominant arm allows the nurse to operate the display device 30 by the dominant arm and provides convenience.

Figure 11:
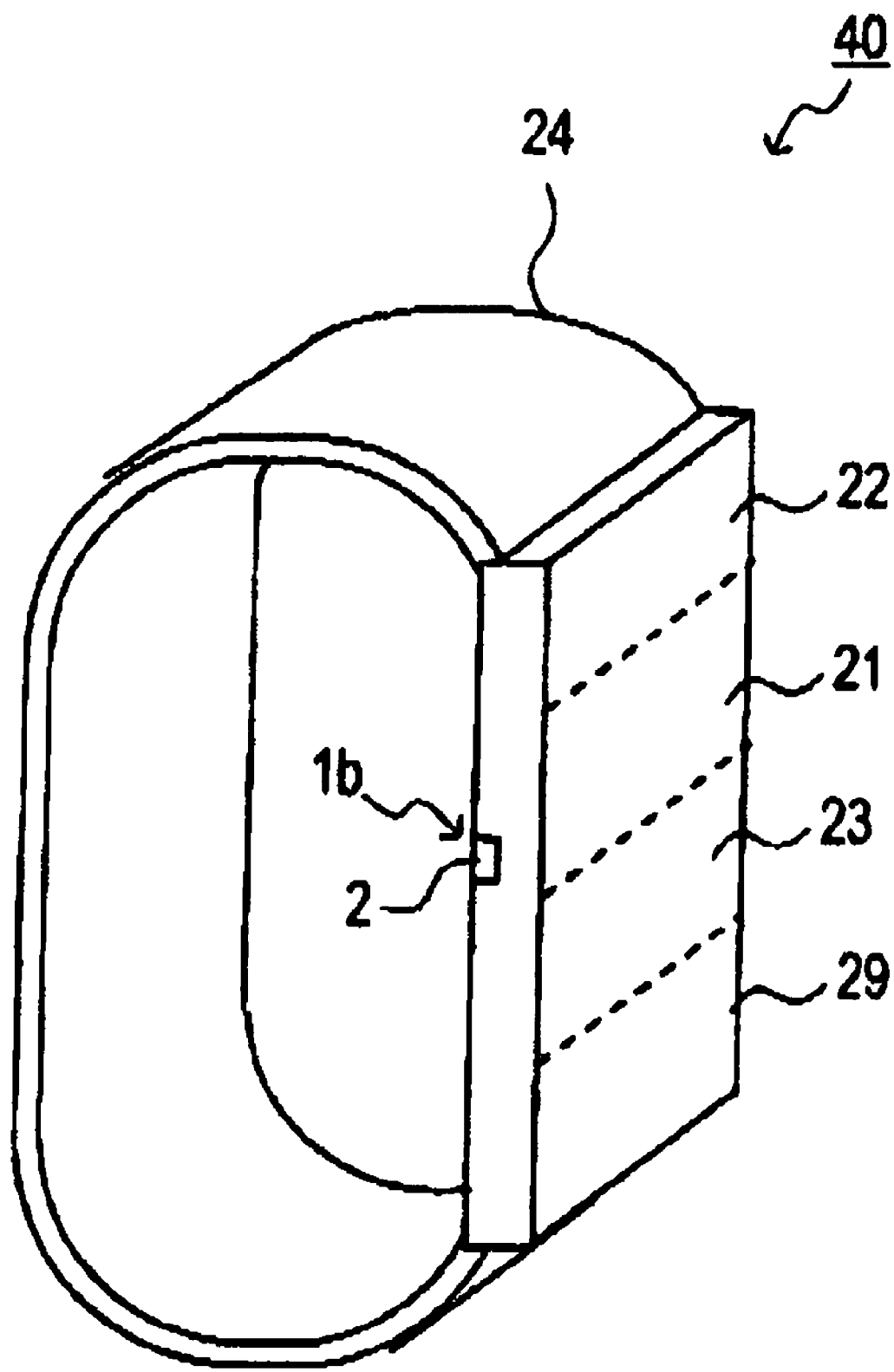
FIG. 11 is a perspective view showing an overall structure of the contact communication device for patient in the application example.

FIG. 11 is a perspective view showing an overall structure of the contact communication device 40 for patient. This contact communication device 40 is different from the contact communication device 20 for nurse in that a measurement portion 29 is provided which measures blood pressure and heart rate of patient. The other components are identical. Thus, detailed explanation of the structure is omitted, by attaching reference numbers used in FIG. 9 to the components identical to the components in FIG. 9. Also, the contact tag 1 used in the contact communication device 40 is referred to as a contact tag 1b.

Figure 12:
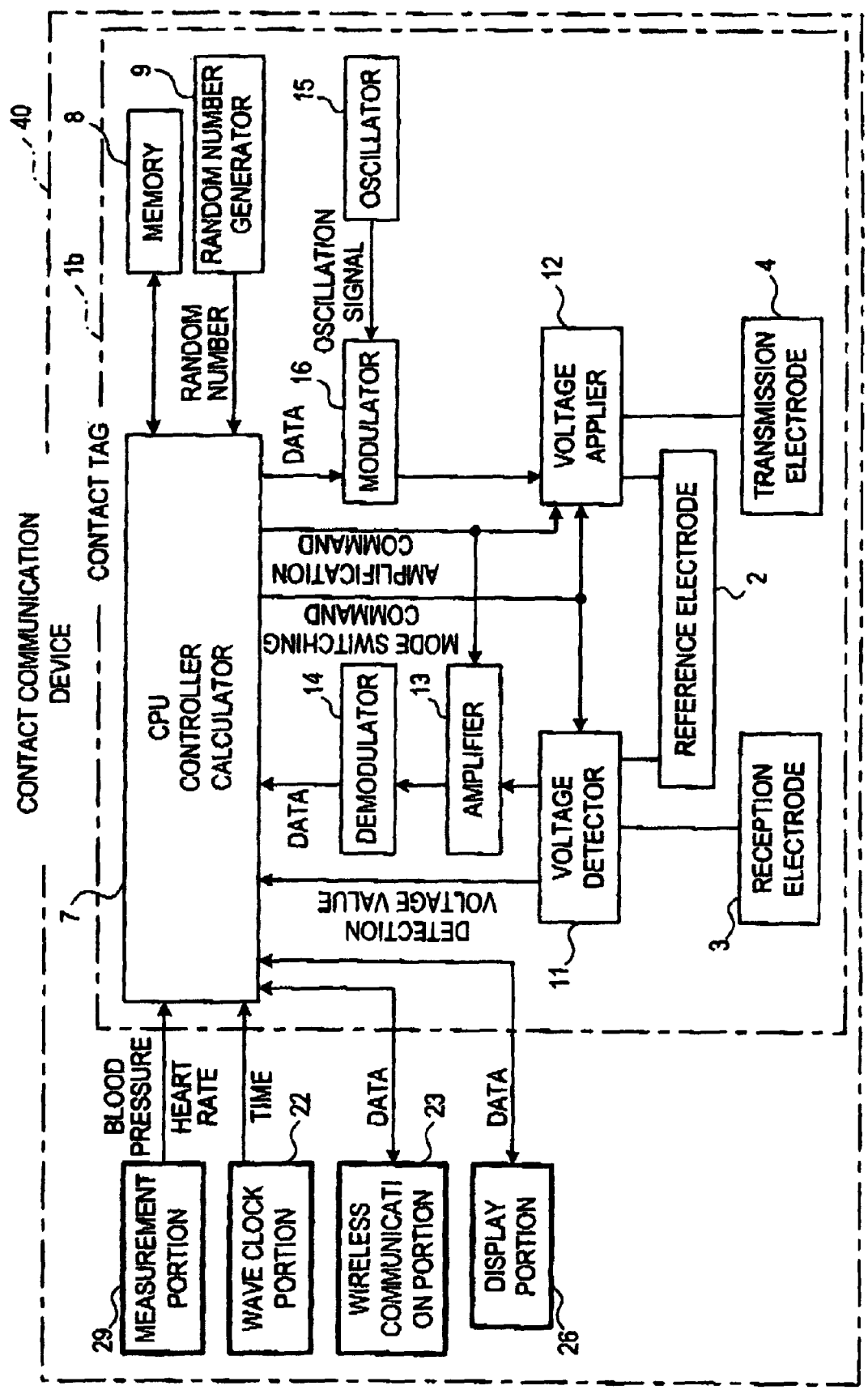
FIG. 12 is a block diagram schematically showing an internal structure of the contact communication device.

FIG. 12 is a block diagram schematically showing an internal structure of the contact communication device 20 for patient. The contact communication device 20 for nurse is structured substantially the same with the contact communication device 40, except that the measurement portion 29 is not provided.

Referring to FIG. 12, blood pressure and heart rate detected by the measurement portion 29 and time measured by the wave clock portion 22 are inputted to the CPU 7 of the contact tag 1b. Also, communication data is inputted/outputted between the CPU 7 and the wireless communication portion 23. Display data is inputted/outputted between the CPU 7 and the display portion 26. It is preferable that only the contact tag is attached to a small sized instrument like a later explained injector of FIG. 13, and that the contact communication device including various equipment added to the contact tag is used in the case without problem with relatively large size like in the case born by human.

Figure 13:
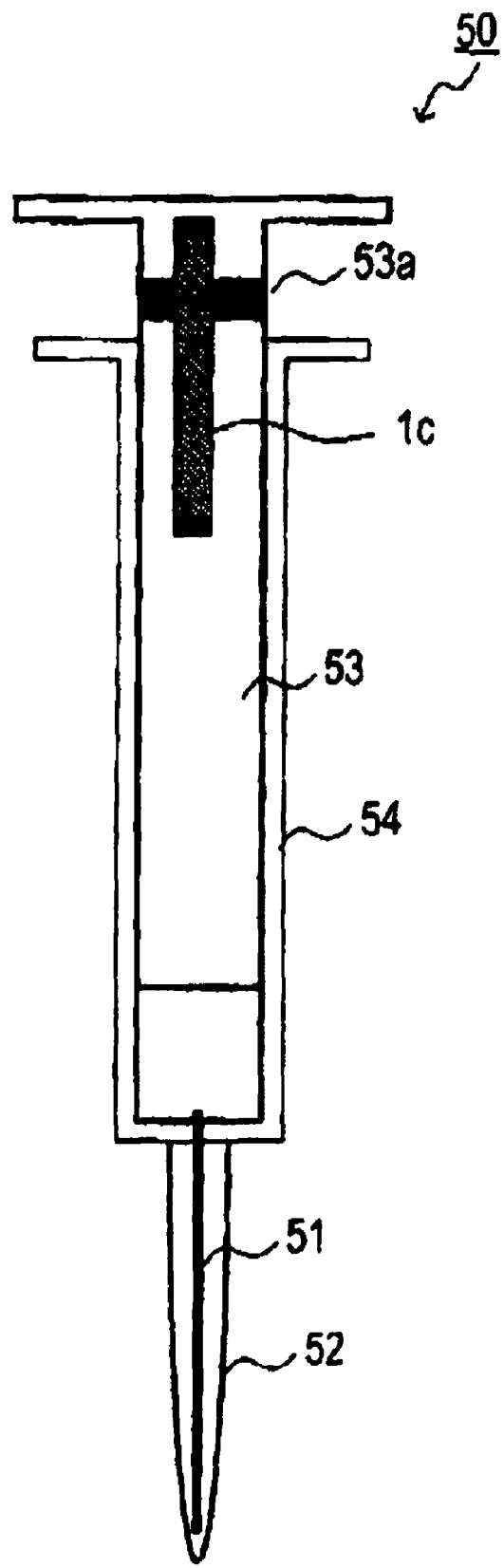
FIG. 13 is an explanatory view showing a structure of an injector in the aforementioned application example to medical services.

Next, FIG. 13 is an explanatory view showing a structure of an injector 50 used in the present application example. Nearly whole of the injector 50 including a needle 51 and a cap 52 is composed of conductive material. There is an insulating portion 53a in a vicinity of a lug of a piston 53 along for a predetermined width. Also, the outer surface of a cylinder 54 is insulated by insulating paint. Moreover, inside the piston 53, a contact tag 1c is embedded through the insulating portion 53a. Accordingly, when a nurse gives an injection, electricity can be carried along a path though the nurse's right hand, the lug of the piston 53, the contact tag 1c, the interior of the piston 53, the interior of the cylinder 54, and the needle 51.

Figure 14:
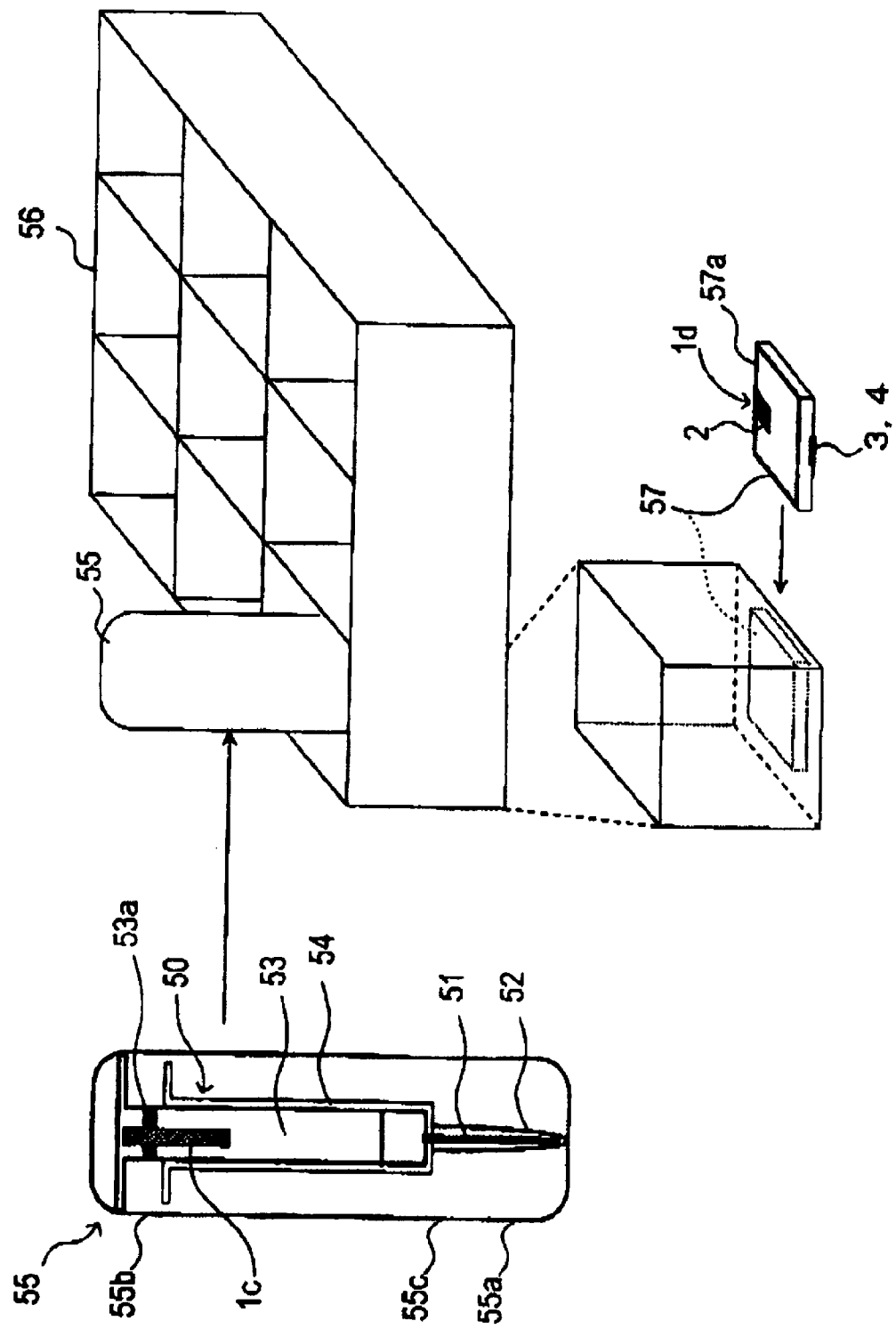
FIG. 14 is an explanatory view showing structures of an injector bag and an injector box in the application example.

FIG. 14 is an explanatory view showing structures of an injector bag 55 and an injector box 56 which accommodates this injector 60. Nearly whole of the injector bag 55 is composed of conductive material. However, an insulating portion 65c is provided to insulate a lower portion 56a that covers the outer circumference of the needle 51 and an upper portion 55b that covers the outer circumference of the piston 53 from each other.

The injector box 66 is partitioned into nine sections so that nine injector bags 56, each bearing an unused injector 50, can be stored. The side wall of the injector box 56 is composed of insulating material. The bottom plate of the injector box 56 is composed of conductive material. At the bottom surface of each section, a support plate 57 is arranged which is composed of insulating material formed into a flattened rectangular parallelepiped. A contact tag 1d is supported by this support plate 57 as follows.

That is, an upper surface 57a of the support plate 57 is entirely coated with conductive paint. One of the electrodes (e.g., the reference electrode 2) of the contact tag 1d is arranged on the upper surface 67a. The other electrode (e.g., the reception electrode 3 or the transmission electrode 4) of the contact tag 1d is arranged on the under surface of the support plate 57, and electrically conducted to the bottom plate of the injector box 56.

Figure 15:
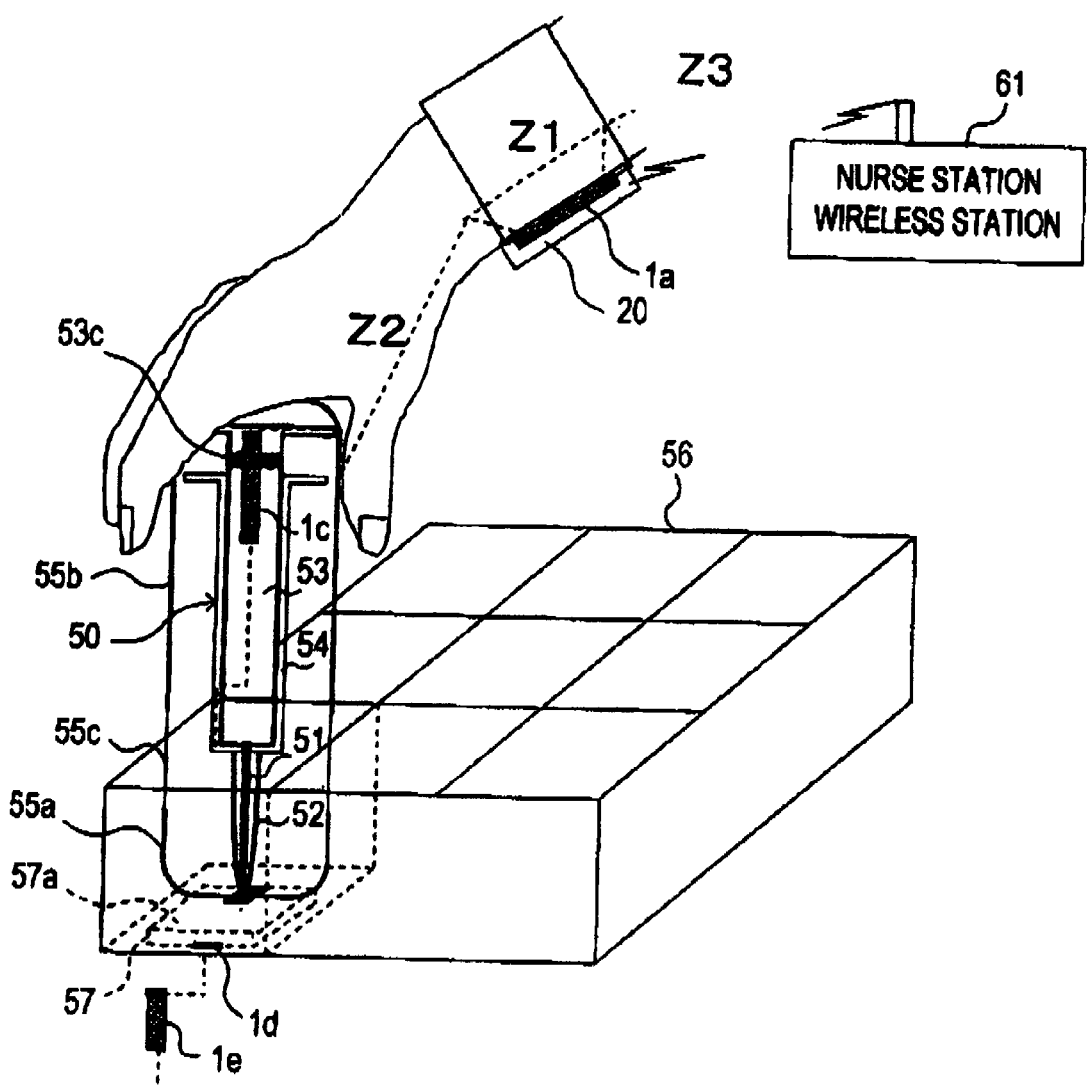
FIG. 15 is an explanatory view illustrating a contact path via the injector bag and the injector box.

Moreover, as shown in FIG. 15, in a contact path extending from the injector box 56 toward a floor surface (not shown), of a rack (not shown) mounting the injector box 56 thereon, a contact tag 1e corresponding to the rack is arranged. The floor surface, nurse shoes, and nurse clothing are also composed of conductive material.

Accordingly, as shown in FIG. 15, when a nurse touches the upper portion 55b of the injector bag 55 to take out the injector 50 stored in the injector box 56, a contact path as follows is created through the nurse's body. That is, the contact path is created which passes through the nurse's body→the nurse's right arm→the upper portion 55b of the injector bag 55→the lug of the piston 53→the contact tag 1c→the interior of the piston 53→the interior of the cylinder 54→the needle 51→the cap 52→the lower portion 55a of the injector bag 55→the upper surface 57a of the support plate 57→the contact tag 1d→the bottom plate of the injector box 56→the upper portion of the aforementioned rack→the contact tag 1e→the lower portion of the aforementioned rack→the floor→the nurse's leg→the nurse's body.

Figure 16:
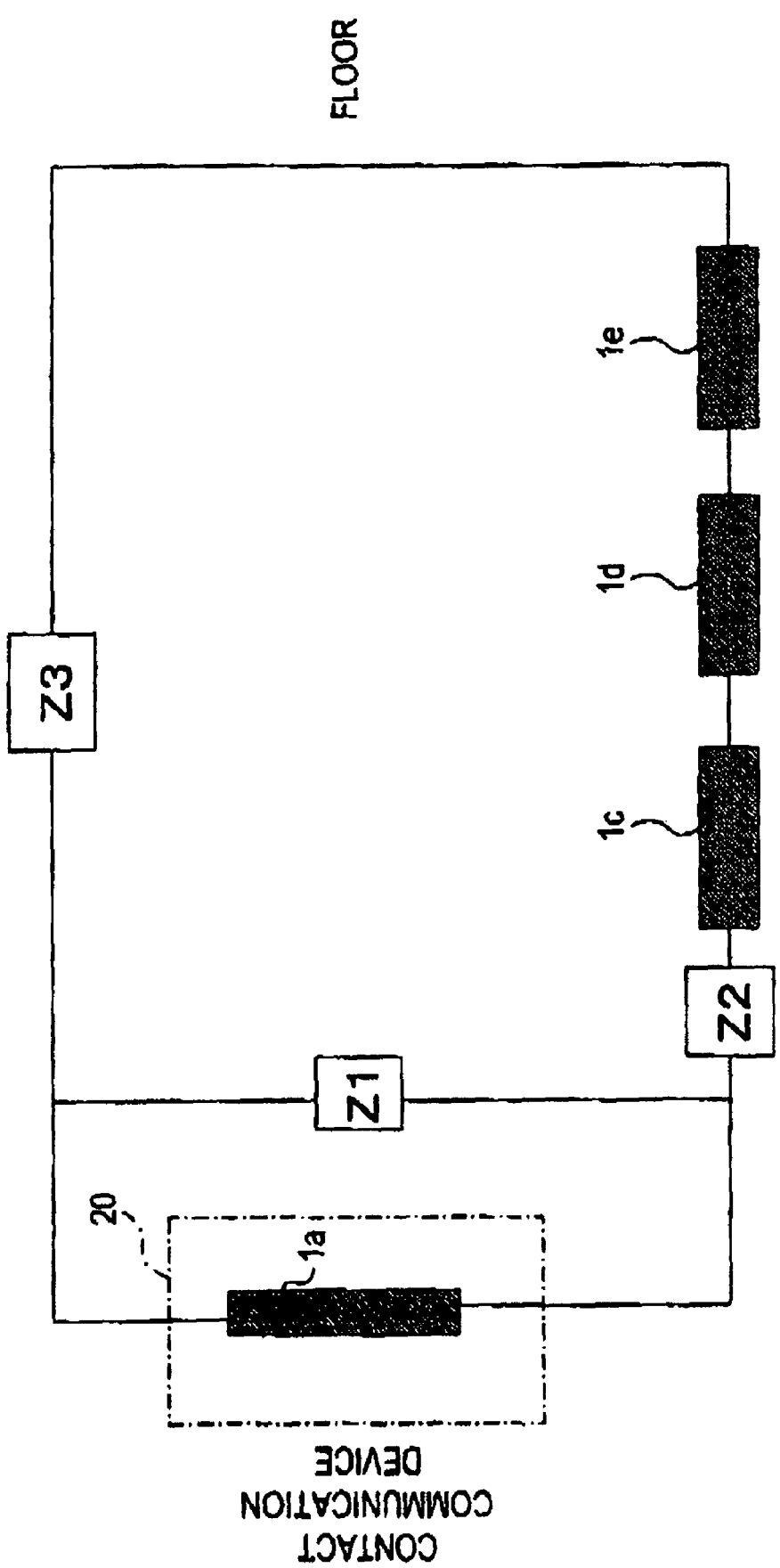
FIG. 16 is an explanatory view showing an equivalent path of the contact path.

The nurse's body has a certain degree of impedance. Let us assume that an impedance of a portion on the nurse's right arm where the contact tag 1a of the contact communication device 20 is abutted is set to Z1, an impedance of a portion from the contact communication device 20 to the fingertip is set to Z2, and an impedance of a portion from the contact communication device 20 to the leg via the nurse's body is set to Z3. Then, an equivalent path as shown in FIG. 16 can be envisaged. The contact tags 1a, 1c, 1d and 1e perform contact communication through this path as noted above. At this time, the contact tag 1a stores communication content of contact communication with the other ends of contact communication, that is, contact tags 1c, 1d and 1e, on its own communication list in the memory 8 of the contact tag 1a. Likewise, the other contact tags also store communication content on the communication list of its own memory.

Figure 17:
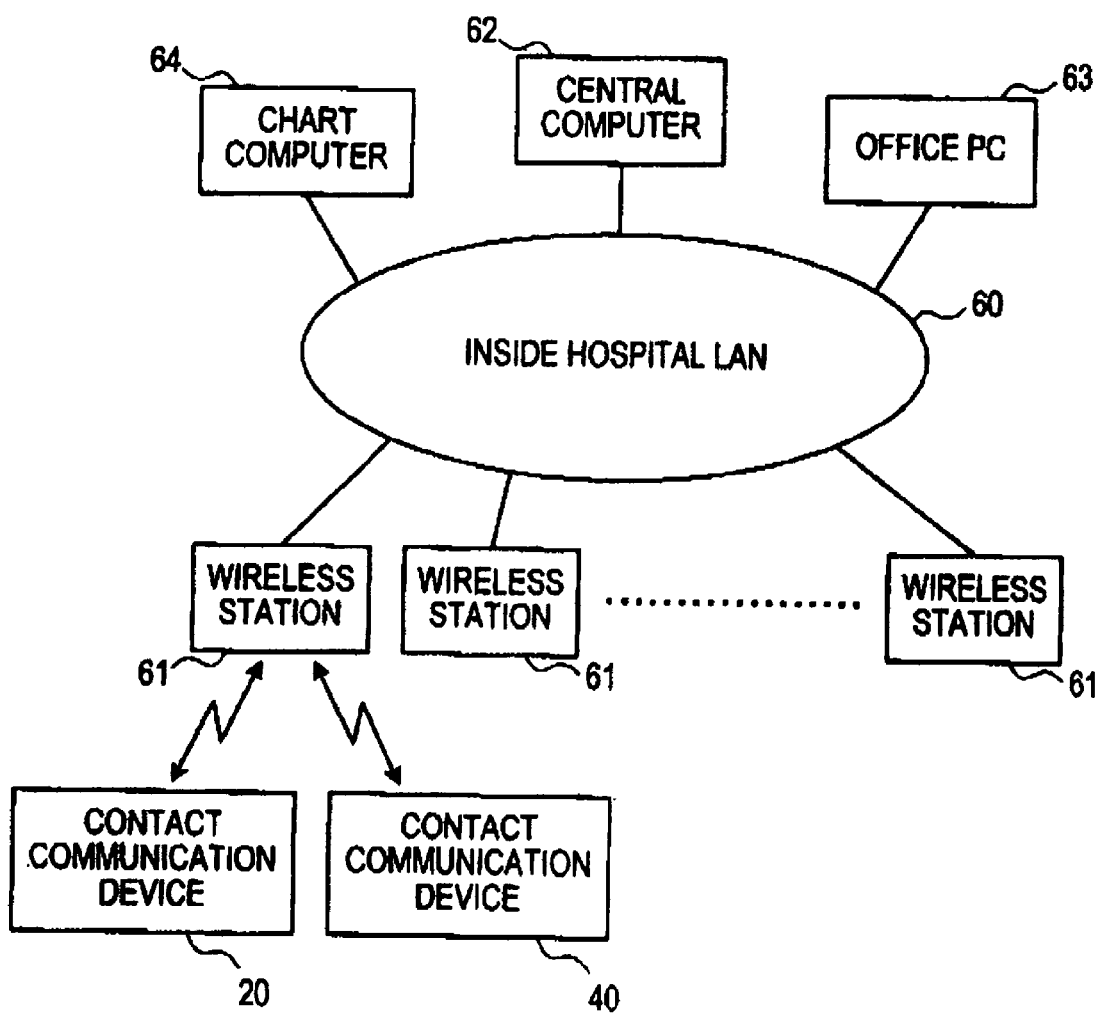
FIG. 17 is an explanatory view showing an overall structure of a system in the aforementioned application example to the medical services.

Referring to FIG. 17, each nurse station, patient room, and pharmacy inside hospital is provided with a wireless station 61. This wireless station 61 is capable of wirelessly communicating with various wireless contact communication devices such as the contact communication device 20, the display device 30, the contact communication device 40, a scale 260 in a pharmacy, etc. Each wireless station 61 is connected to each other via the inside hospital LAN 60. Also, a central computer 62, an office personal computer (office PC) 63, and a chart computer 64 are connected to the inside hospital LAN 60. Each apparatus connected to this inside hospital LAN 60 exchanges data in its own memory and always updates the data to the latest via the central computer 62. Thereby, a chart with records, for example of condition of patient and treatment method, is updated to the latest. Communication lists of the other contact tags can be also obtained.

Generally, in contact communication, there is no communication of enormous amounts of data so that the communication is completed in a short time. However, contact communication may be used to update chart information or obtain communication lists of other contact tags as noted above. In this manner, even in places where wireless communication is difficult or in a state in which a wireless LAN is not operated due to power failure, etc., information can be exchanged every time the contact communication devices are in contact with each other. As information is exchanged by contact communication with a new contact communication device in sequence like whisper down the lane, transmission and update of information can be conducted.

Figure 18:
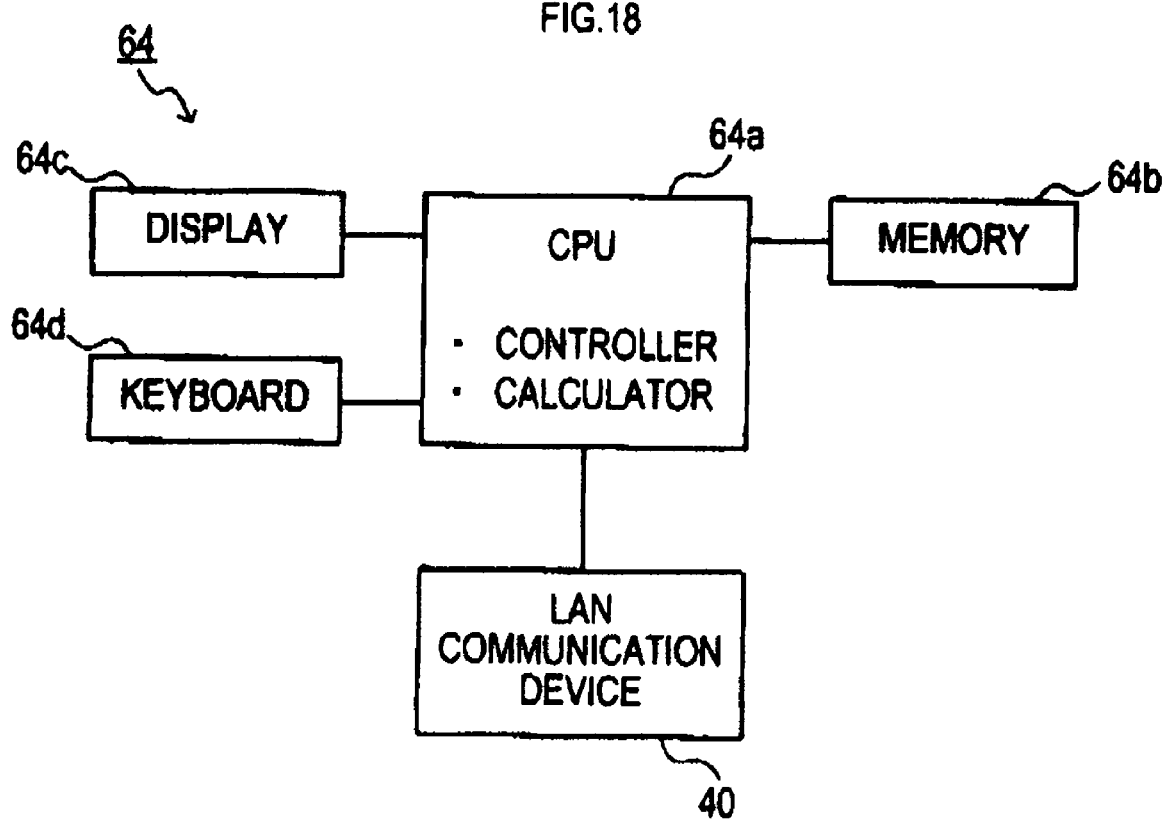
FIG. 18 is a block diagram showing a structure of a chart computer of the system.

As shown in FIG. 18, the chart computer 64 includes a CPU 64a, a memory 64b, a display 64c, a keyboard 64d, and a LAN communication device 64e. The CPU 64a incorporates a controller and a calculator therein. The memory 64b stores various data. The display 64c displays various images. The keyboard 64d is used for various inputs. The LAN communication device 64e is for communication with the inside hospital LAN 60. The chart computer 64 is provided with a function as a contact communication device. The CPU 64a is provided with a function of the CPU 7 of the contact tag 1. The memory 64b is provided with a function of the memory 8 of the contact tag 1.

Processes in the chart computer 64 and in the contact tag 1 will be explained later. Now, explanation will be given on the contact tag 1 in instruments other than the injector 50.

FIG. 19(A) is a longitudinal sectional view showing a structure of a liquid medicine bottle 70. FIG. 19(B) is a perspective view showing a structure of a lid 71 of the liquid medicine bottle 70. FIGS. 19(C) and (D) are a cross sectional view taken by the line B-B and a cross sectional view taken by the line C-C of FIG. 19(A). In each view, a screw portion for securing the lid 71 to a container body 72 is omitted. In FIG. 19(B), conductive portions are shown by hatching. In other figures, conductive portions are shown by heavy line.

Figure 19:
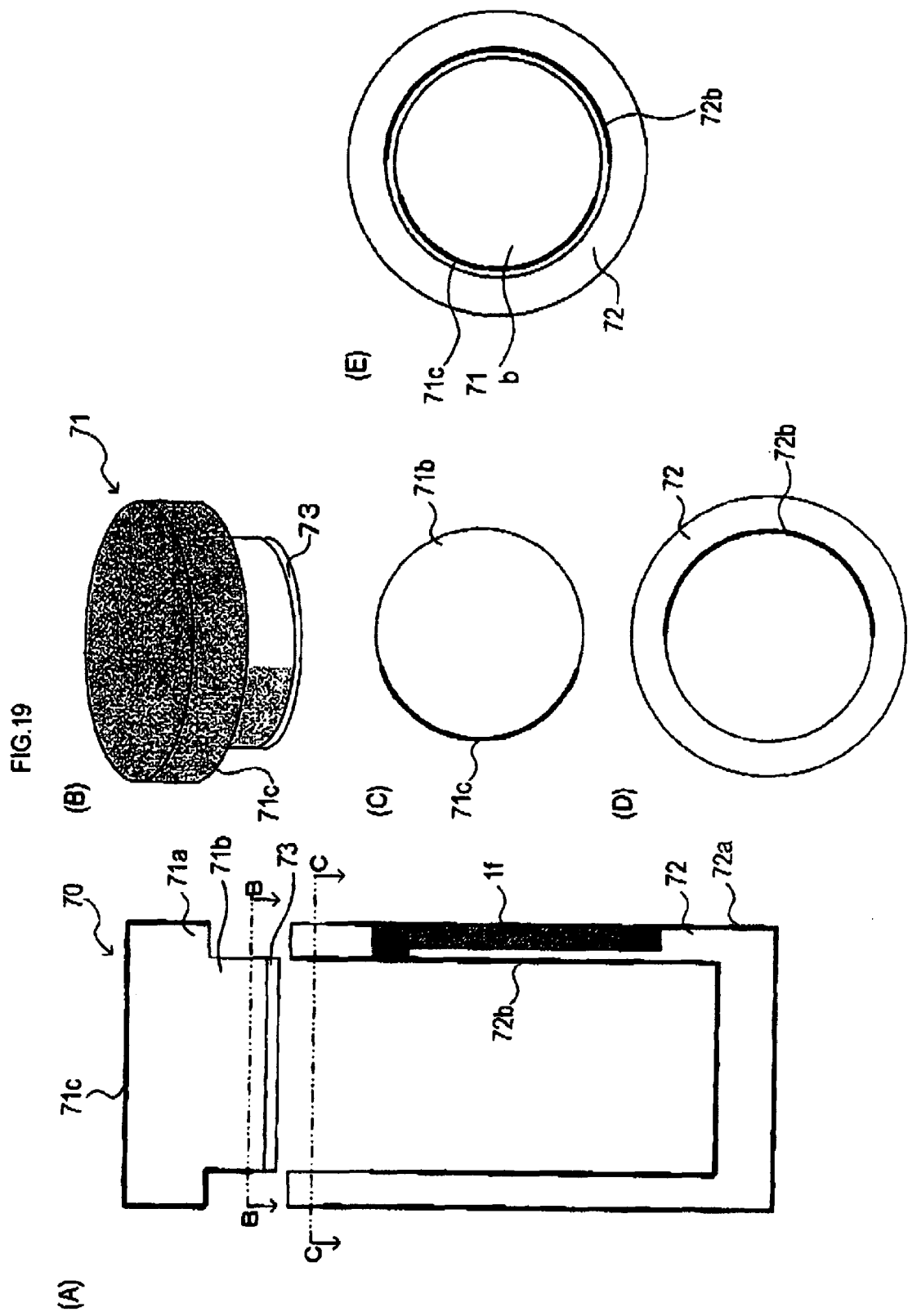
FIG. 19 is a longitudinal sectional view, a perspective view, a cross sectional view taken by the line B-B, a cross sectional view taken by the line C-C, and an operation explanatory view showing a structure of a liquid medicine bottle in the aforementioned application example to medical services.

Referring to FIGS. 19(A) to (C), the lid 71 includes a conductive portion 71c composed of the outer circumferential surface and the upper surface of a large diameter portion 71a, and less than half of the outer circumferential surface in a circumferential direction of a small diameter portion 71b. The conductive portion 71c is formed on part of the under surface of the large diameter portion 71a. Thus, the lid 71 is electrically conducted as a whole. In the container body 72, a conductive portion 72a is formed on the nearly whole outer circumferential surface, and a conductive portion 72b is formed on the nearly whole inner wall surface, respectively. The conductive portion 72b is not formed at a portion facing the conductive portion 71c of the small diameter portion 71b in a tightly stoppered state to allow for a little margin. Moreover, the conductive portion 72a is not formed on the upper end surface facing the large diameter portion 71a and the upper outer circumferential end adjacent to the outer circumference of the large diameter portion 71a. Therefore, the conductive portion 72b of the inner wall surface of the container body 72 and the conductive portion 71c of the outer circumferential surface of the small diameter portion 71b are, as shown in FIG. 19(E), not electrically conducted in a tightly stoppered state. In FIG. 19, a gap is provided between the outer circumferential surface of the small diameter portion 71b and the inner circumferential surface of the container body 72 as a matter of convenience. However, the both surfaces are closely attached in practice.

Also, at the lower end of the small diameter portion 71b of the lid 71, an insulating sealing rubber 73 is provided so that, even if a liquid medicine 79 (see FIG. 22) is conductive, the conductive portion 72b and the conductive portion 71c are not electrically conducted in a tightly stoppered state. Moreover, the sealing rubber 73 is designed to swell as the liquid medicine bottle 70 is once opened, so that the liquid medicine bottle 70 is no longer stoppered. Also, a contact tag 1f is embedded between the conductive portions 72a and 72b of the container body 72.

Figure 20:
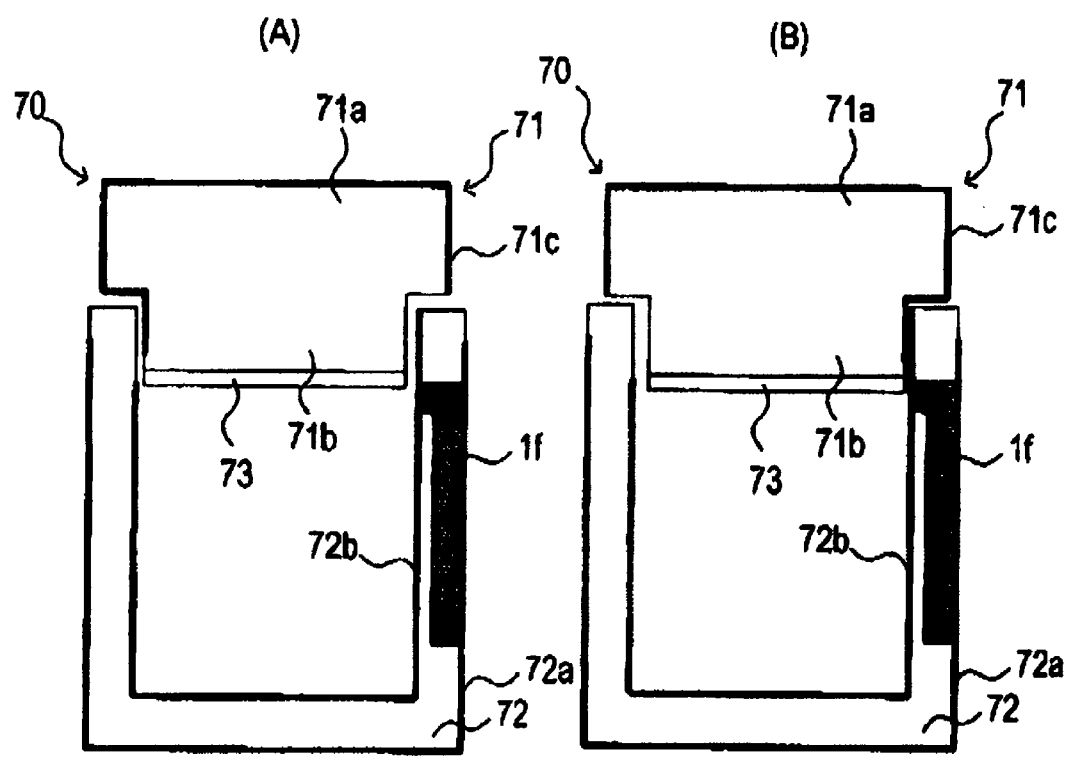
FIG. 20 is an explanatory view showing operation of the liquid medicine bottle in a longitudinal cross section.

In the above structured liquid medicine bottle 70, the conductive portion 71c and the conductive portion 72b are perfectly insulated in a stoppered state as shown in FIG. 20(A). Therefore, the conductive portion 72b is completely insulated from the outside. There is no path created which passes the contact tag 1f even if a nurse touches the liquid medicine bottle 70 in what manner.

Figure 21:
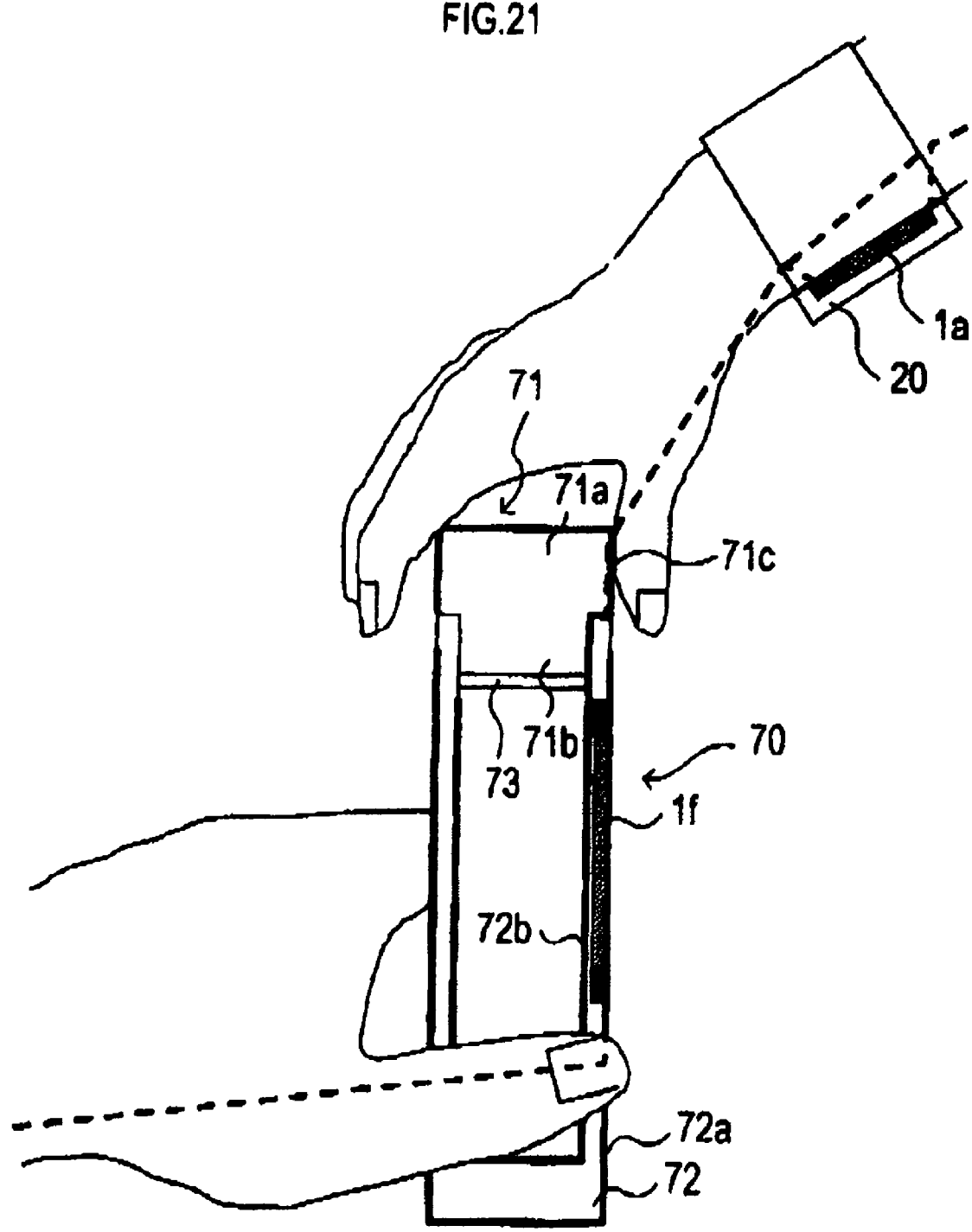
FIG. 21 is an explanatory view illustrating a contact path via the liquid medicine bottle.

When a nurse rotates the lid 71 to open the liquid medicine bottle 70, the conductive portion 71c and the conductive portion 72b are electrically conducted as shown in FIG. 20(B). Normally, at this time, the nurse holds the liquid medicine bottle 70 as shown in FIG. 21. That is, the nurse holds the outer circumference of the large diameter portion 71a of the lid 71 at the right hand, and the outer circumference of the container body 72 at the left hand. Then, a contact path is formed which passes through the nurse's body→the nurse's right arm→the conductive portion 71c→the conductive portion 72b→the contact tag 1f→the conductive portion 72a→the nurse's left arm→the nurse's body. Accordingly, as noted above, there is contact communication between the contact tag 1a of the contact communication device 20 and the contact tag 1f.

Figure 22:
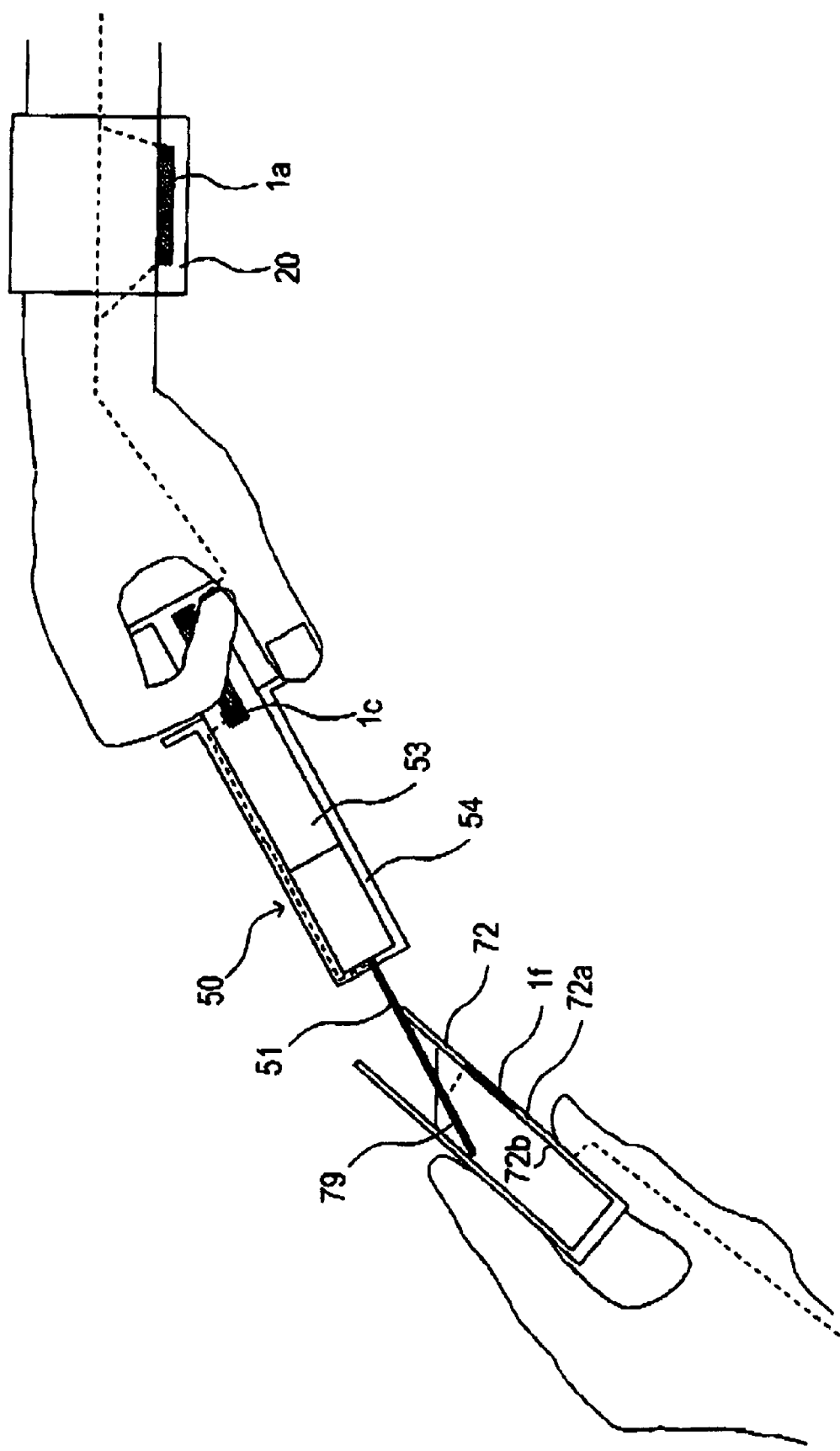
FIG. 22 is an explanatory view illustrating a contact path via the aforementioned injector and the aforementioned liquid medicine bottle.

Also, as in FIG. 22, after the liquid medicine bottle 70 is opened and when the inner surface of the container body 72 or the liquid medicine 79 and the needle 51 of the injector 50 are brought into contact in an attempt of the nurse to feed the liquid medicine 79 of the liquid medicine bottle 70 into the injector 50, the following contact path is generated. The contact path is created which passes through the nurse's body→the nurse's right arm→the lug of the piston 53→the contact tag 1c→the interior of the piston 53→the interior of the cylinder 54→the needle 51→the conductive portion 72b→the contact tag 1f→the conductive portion 72a→the nurse's left arm→the nurse's body. Accordingly, as noted above, there is contact communication among the contact tag 1a of the contact communication device 20, the contact tag 1c, and the contact tag 1f.

As noted above, the liquid medicine bottle 70 is designed never to be sealed once opened, due to swelling of the sealing rubber 73. Thus, it is possible to determine that the liquid medicine bottle 70 is opened when the ID of the contact tag 1f is detected for the first time. It is also possible that the liquid medicine bottle 70 is already opened in the case of detection for the second time onwards.

Figure 23:
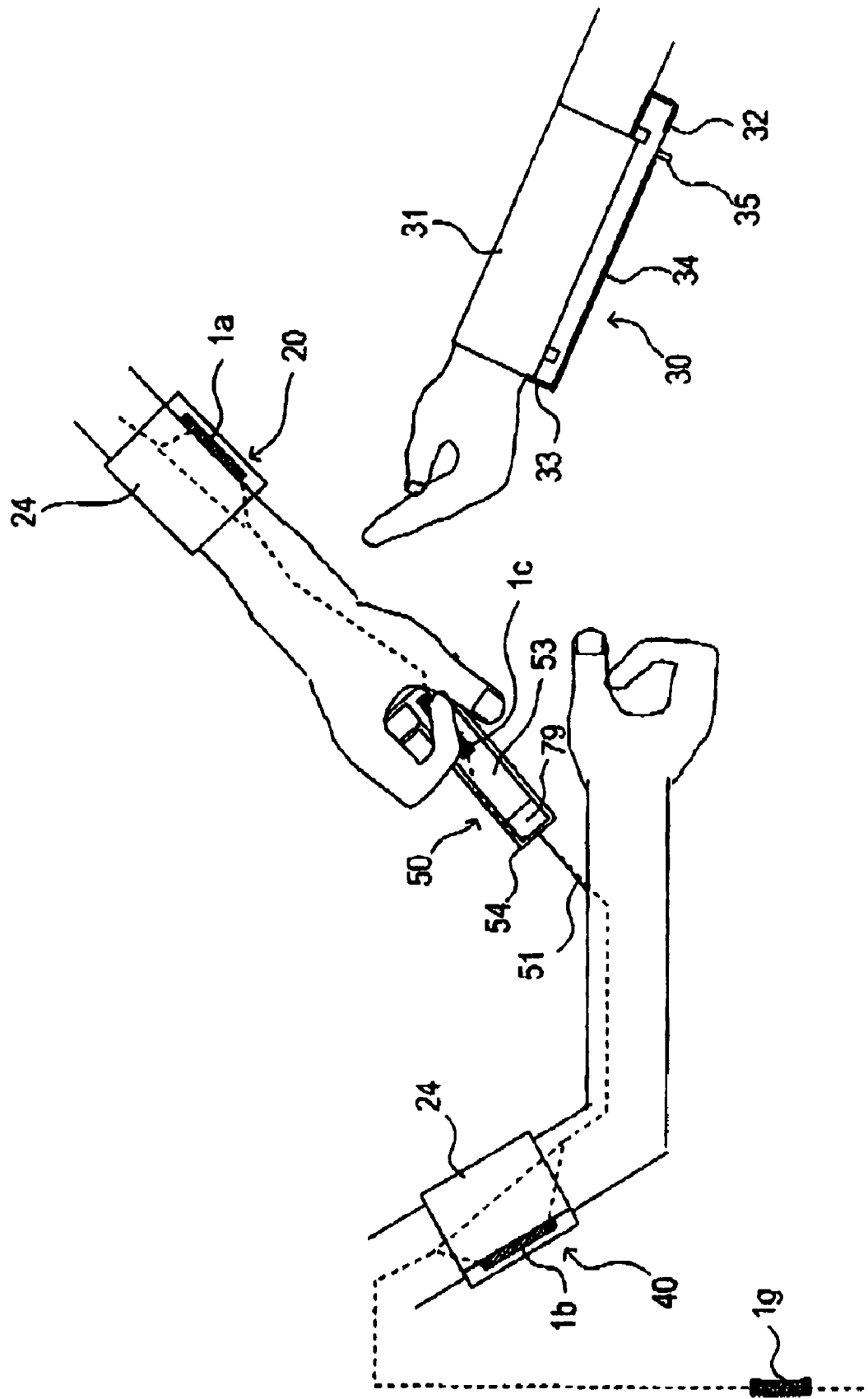
FIG. 23 is an explanatory view illustrating a contact path via the aforementioned injector and a patient.

Subsequently, when the nurse injects the liquid medicine 79 into a patient, the following contact path is created. It is assumed that patient clothing is also conductive, and a contact tag 1g is provided in a chair (not shown) with the patient sitting thereon, as in the case of the aforementioned rack of the injector box 56. In this case, as shown in FIG. 23, a contact path is created which passes through the nurse's body→the nurse's right arm→the lug of the piston 53→the contact tag 1c→the interior of the piston 53→the interior of the cylinder 54→the needle 51→the patient's arm→the patient's body→the contact tag 1g→the floor→the nurse's leg→the nurse's body. In this manner, contact communication is performed among the contact tags 1a, 1b, 1c and 1g.

Also, when the nurse gives injection, etc., the contact tag 1a of the contact communication device 20 of the nurse transmits stored data to the display device 30 to display detailed information, so that the treatment content, etc. can be confirmed. Largely, there could be three ways to achieve this method.

Figure 24:
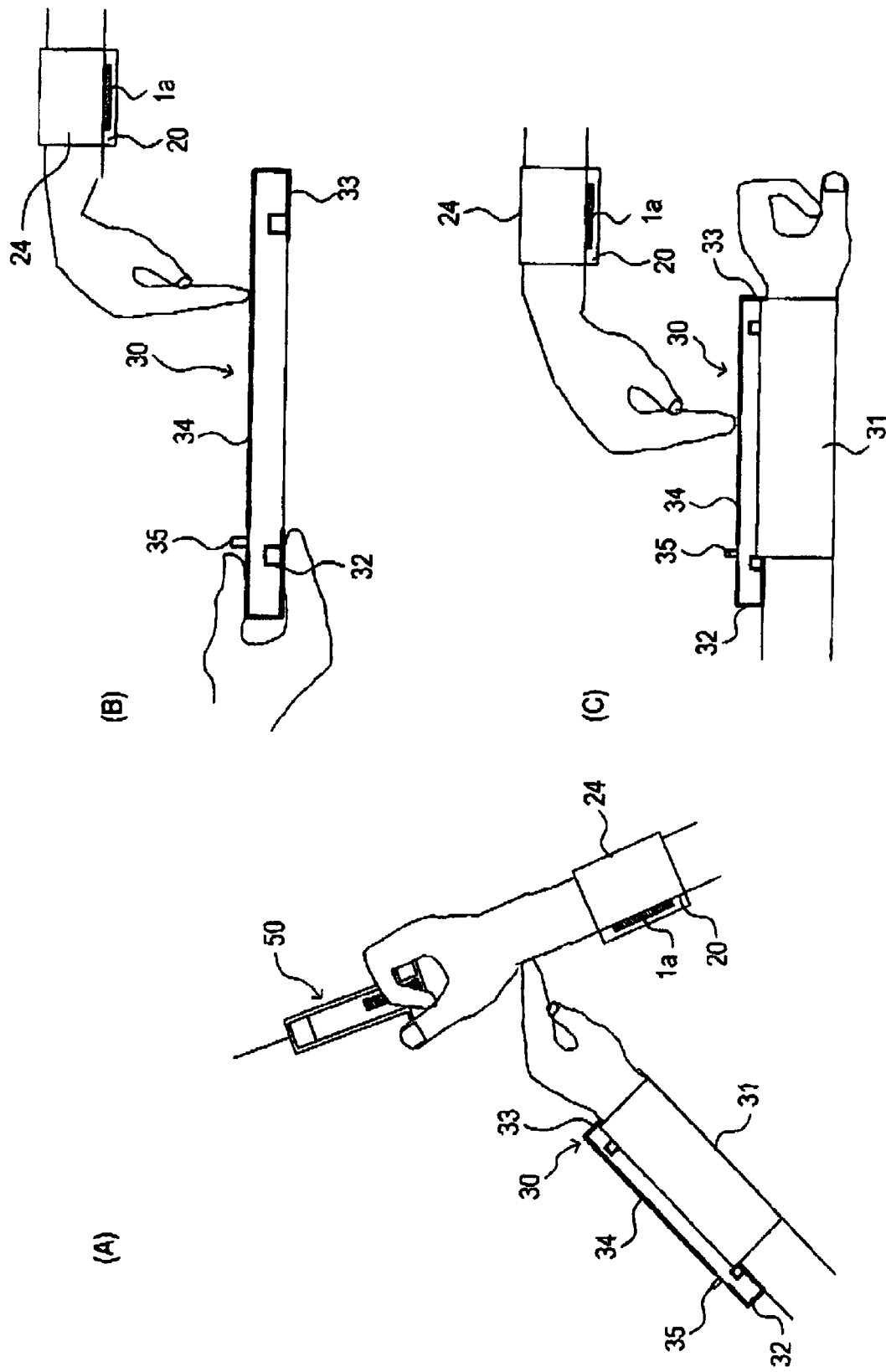
FIG. 24 is an explanatory view illustrating how to use a display device.

The simplest way is, as shown in FIG. 24(A), to bring the nurse's right hand and left hand into contact while the display device 30 is born on the nurse's left arm. In this case, data is transmitted from the contact tag 1a to the display device 30 via a path passing through the contact tag 1→the nurse's right hand→the nurse's left hand→the right hand grip portion 33 of the display device 30→the left hand grip portion 32 of the display device 30→the nurse's left arm→the nurse's body→the nurse's right arm→the contact tag 1a. In this case, the above display can be done with the injector 50 held by the right hand.

Also, as shown in FIG. 24(B), the display device 30 may be taken off from the left arm, the left hand grip portion 32 may be held by the left hand, and the right hand may be brought into contact with the display portion 34 or the right hand grip portion 33. Moreover, as shown in FIG. 24(C), while the display device 30 is born on the left arm, the right hand may be brought into contact with the display portion 34.

Next, FIG. 25(A) is an explanatory view showing a structure of a tablet bottle 80. As shown in FIG. 25(A), the tablet bottle 80 is composed of a lid 81 and a container body 82. The nearly whole of the tablet bottle 80 is composed of conductive material. However, a side wall portion 82a and a bottom plate portion 82b of the container bottle 82 are insulated by an insulating portion 82c. A contact tag 1h is embedded through the insulating portion 82c between the side wall portion 82a and the bottom plate portion 82b.

FIG. 25(B) shows a structure of a scale 85. The scale 85 is provided with a scalepan 86a capable of mounting the tablet bottle 80 on a body 86. Three out of four legs 87 supporting the body 86 is composed of insulating material. One leg 87a is composed of conductive material except for a base 87b composed of insulating material. That is, the tip of the leg 87a is insulated from the conductive scalepan 86a and the body 86 across the base 87b of insulating material. A contact tag 1i is embedded through the base 87b of insulating material between the tip of the leg 87a and the body 86.

Similarly, in a rack 88 which mounts the tablet bottle 80 or the scale 85 thereon, three out of four legs 89 has an insulating portion 89a at the tip, as shown in FIGS. 26(A) and (B). One leg 89b has an insulating portion 89c at the middle. The other portion of the rack 88 is composed of conductive material. A contact tag 1j is embedded through the insulating portion 89c between conductive portions of the leg 89b.

Accordingly, when the nurse touches the tablet bottle 80 mounted on the rack 88, a contact path is created which passes through the nurse's body→the nurse's right arm→the lid 81→the side wall portion 82a→the contact tag 1h→the bottom plate portion 82b→the upper portion of the rack 88→the upper portion of the leg 89b→the contact tag 1j→the tip of the leg 89b, the floor→the nurse's leg→the nurse's body, as shown in FIG. 26(A). In this manner, contact communication is performed among the contact tags 1a, 1h, and 1j.

Also, when the tablet bottle 80 is placed on the scale 85 mounted on the rack 88, A contact path is created which passes through the nurse's body→the nurse's right arm→the lid 81→the side wall portion 82a →the contact tag 1h→the bottom plate portion 82b→the scalepan 86a→the body 86→the contact tag 1i→the tip of the leg 87a→the upper portion of the rack 88→the upper portion of the leg 89b→the contact tag 1j→the tip of the leg 89b→the floor→the nurse's leg→the nurse's body, as shown in FIG. 26(B). In this manner, contact communication is performed among the contact tags 1a, 1h, 1i, and 1j.

There are general racks (conductive on the whole) without the contact tag 1j in hospital. In case that the tablet bottle 80 or the scale 85 is mounted on such racks, part of the aforementioned contact path, that is, "→the upper portion of the rack 88→the upper portion of the leg 89b→the contact tag 1j→the tip of the leg 89b→" is replaced with just "→the rack→". Contact communication is performed among the contact tags 1a, 1h, and 1i excluding the contact tag 1j.

Figure 25:
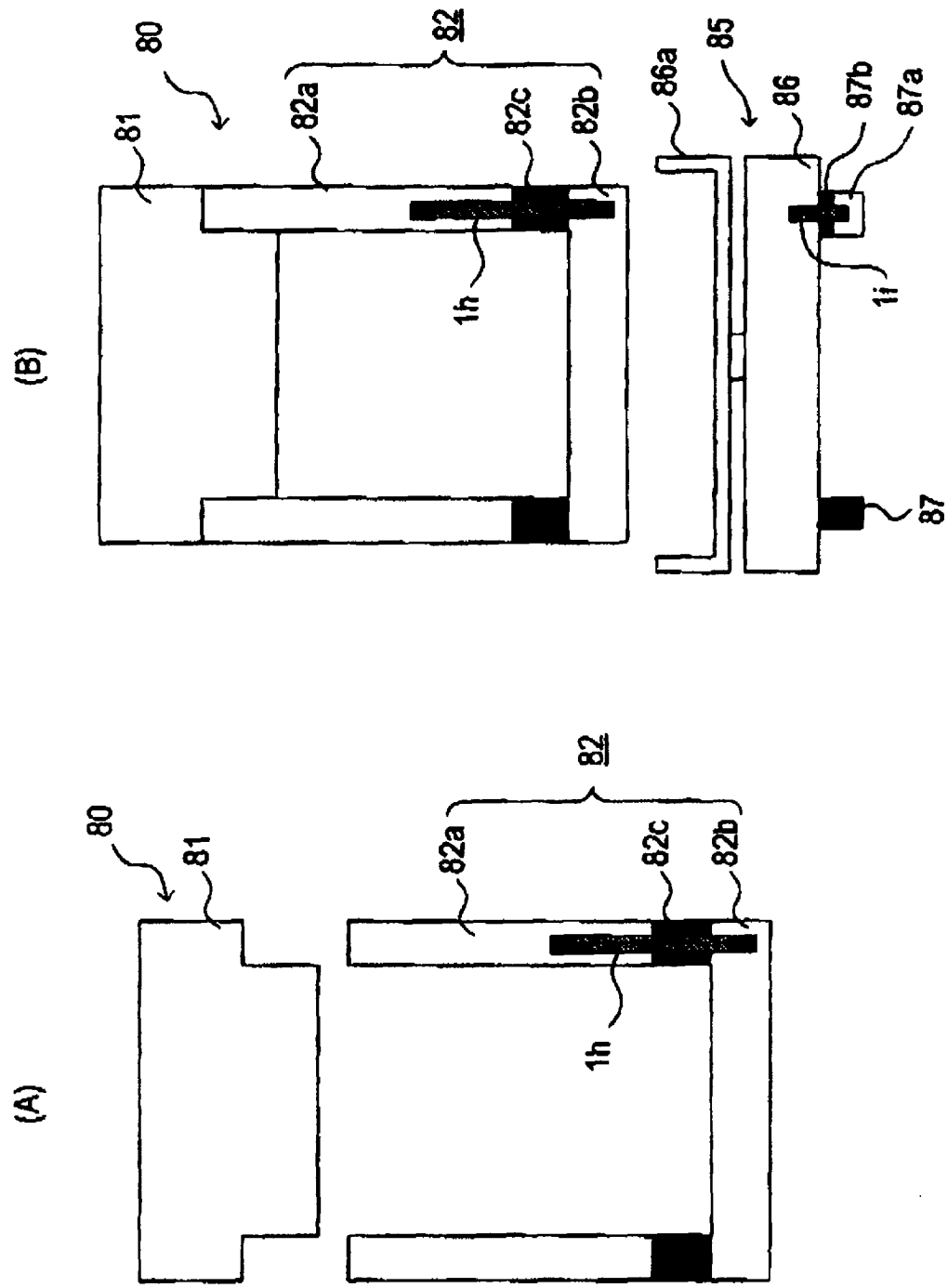
FIG. 25 is an explanatory view showing structures of a tablet bottle and a scale in the aforementioned application example to medical services.

Use of the table bottle 80 as shown in FIG. 25 allows to check such as missing of dose by patient, contraindication, medicine overdose, etc. Every time the patient opens the lid 81 of the tablet bottle 80 as shown in FIG. 25(A), a contact path is created between the patient and the tablet bottle 80, for example, as the lid 81 is held by the patient's right hand and the container body 82 is held by the left hand in an attempt to open the lid 81. In this manner, the contact tag 1h of the tablet bottle 80 performs contact communication. Then, opening of the lid 81 is detected. If a clock is equipped with the tablet bottle 80, when the tablet bottle 80 is opened is recorded to check missing of dose. The patient is not necessarily provided with the contact communication device 20. If the patient is provided with the contact communication device 20, the contact tag 1h of the tablet bottle 80 can detect who opened the lid 81. However, normally, who takes the medicine is obvious. Thus, detection of only whether the lid 81 has been opened is necessary. If the contact tag 1h of the tablet bottle 80 is a contact tag of simultaneous transmission/reception type which receives self-transmitted data, the above check can be achieved (explanation will be given later on the contact tag of simultaneous transmission/reception type).

Also, the scale 85 as shown in FIG. 25(B) may be integrated into the table bottle 80. Every time the medicine is taken, the amount of dose may be capable of being detected. In this case, a contact path is created for detection by contact communication, which passes through the patient→the lid 81 of the tablet bottle 80→the container body 82 of the tablet bottle 80→the contact tag 1h→the scalepan 86a→the contact tag 1i→the leg 87a of the scale 85→the floor→the patient. The amount of dose can be detected by contact communication. In this case, not only missing of dose can be checked, but also notification may be given by a buzzer when a necessary amount of medicine is taken out even if the medicine is not subdivided beforehand into doses since the taken amount of the medicine is detected.

Figure 27:
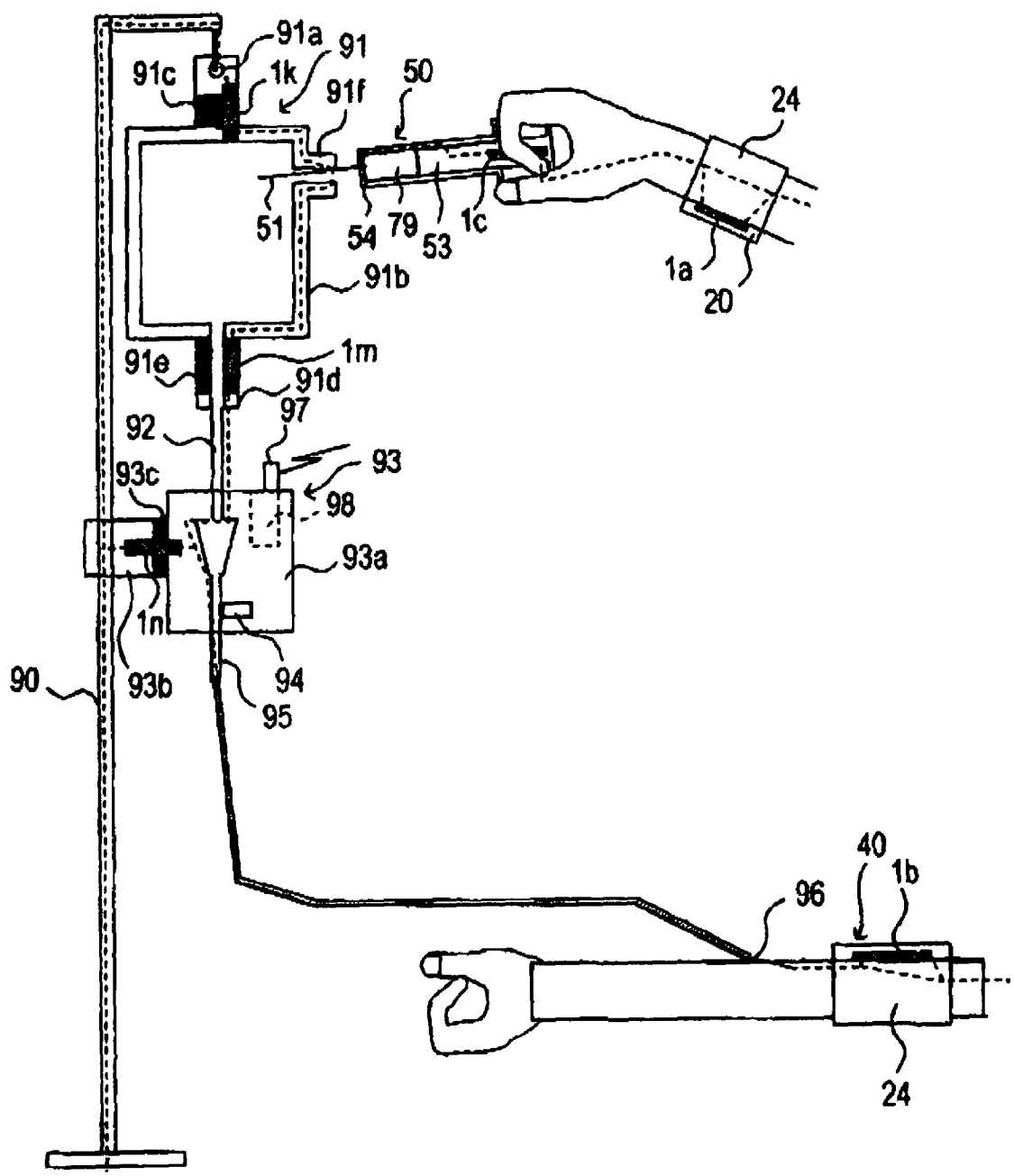
FIG. 27 is an explanatory view showing various structures relating to intravenous drip in the aforementioned application example to medical services.

FIG. 27 is an explanatory view showing structures of various equipment related to intravenous drip. In this case as well, most parts are composed of conductive material. However, an insulating portion 91c, an insulating portion 91e, and an insulating portion 93c are respectively formed between a hanging hole 91a for hanging an intravenous bottle 91 from a stand 90 and an intravenous bottle body 91b, between a tube opening 91d for connecting a tube 92 to the lower portion of the intravenous bottle 91 and the intravenous bottle body 91b, between a body 93a of a dropper 93 and a fixing portion 93b for fixing the body 93a to the stand 90.

A contact tag 1k which connects a vicinity of the hanging hole 91a and the intravenous bottle body 91b across the insulating portion 91c, a contact tag 1m which connects the intravenous bottle body 91b and the tube opening 91d across the insulating portion 91e, and a contact tag 1n which connects the body 93a and the fixing portion 93b across the insulating portion 93c are respectively arranged.

The dropper 93 is provided with a not shown infrared ray sensor. The dropper 93 controls a pressure amount in the tube 95 by a pressure stick 94 so that a dripping amount of the liquid medicine 79 detected by the infrared ray will be a scheduled amount. The tube 92 connected to the tube opening 91d is connected to the upper portion of the dropper 93. To the tip of the tube 95, an intravenous needle 96 is connected so as to be connected to the patient's arm. Also, the dropper 93 has an antenna 97 and a wireless portion 98. The dropper 93 is connected to the inside hospital LAN via wireless communication.

Figure 28:
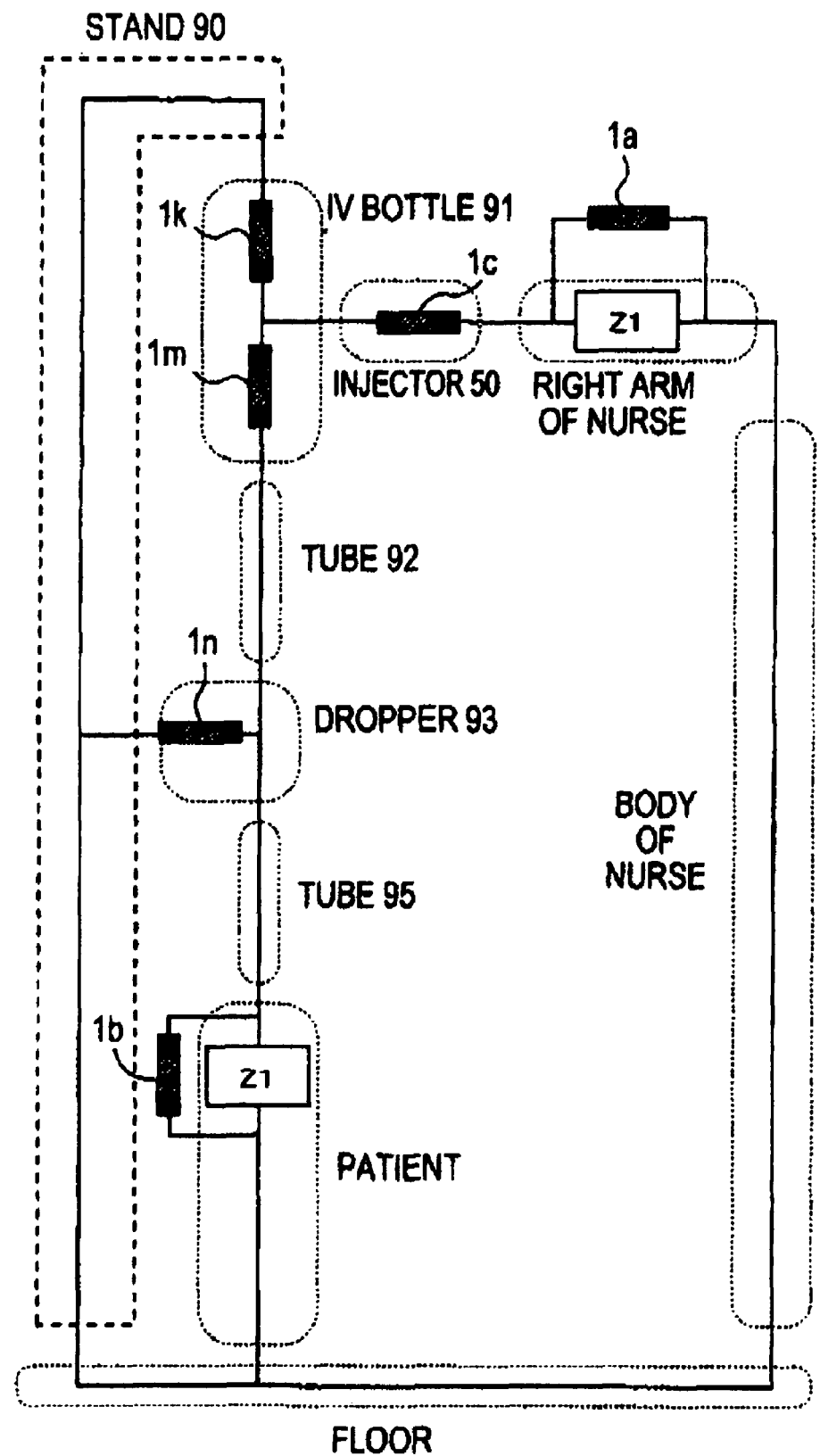
FIG. 28 is an explanatory view illustrating an equivalent path of a contact path via the structures.

In this case, if the nurse attempts to inject the liquid medicine 79 by the injector 50 from an inlet 91f of the intravenous bottle 91, a complex path as shown in FIG. 28 is created. In FIG. 28, an impedance at a portion on the patient's arm where the contact tag 1b of the contact communication device 40 is abutted is also set to Z1. In this manner, contact communication is performed among the contact tags 1a, 1b, 1c, 1k, 1m and 1n.

Next, a contact communication method using data such as the above ID, etc. will be explained. As described above, each ID directly corresponds to the contact tag 1 or a room (a nurse station, a patient room, etc.). However, hereinafter, the ID of the contact tag 1a, the ID of the contact tag 1b, the ID of the contact tag 1f, etc. may be represented as an equivalent of each ID such as the ID of the nurse A, the ID of the patient B, the ID of the liquid medicine bottle F, etc., as a matter of convenience.

Figure 35:
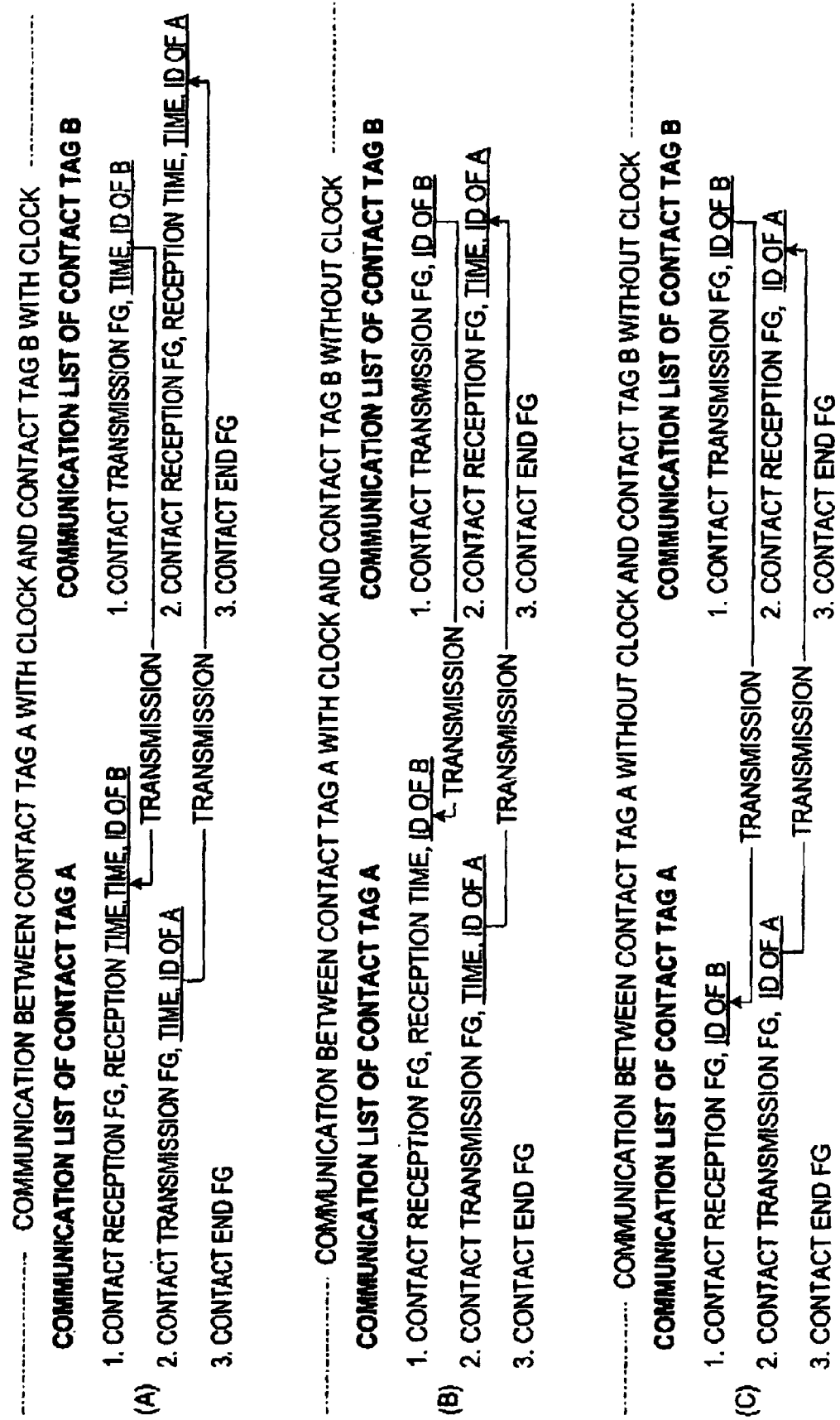
FIG. 35 is an explanatory view illustrating various patterns of contact communication.

First of all, each contact tag 1 stores results of transmission/reception of the IDs as above on its own communication list as follows. For example, FIG. 35(C) illustrates a communication list when contact communication is performed between two contact tags both without clock. The explanation is given herein.

Firstly, the contact tag B, when transmitting data (its own ID=ID of the contact tag B) by contact communication, stores the transmitted data (ID of the contact tag B) together with a contact transmission FG indicating that the data has been transmitted by contact communication as a first item of the communication list of its own (the contact tag B). Next, the contact tag A, when receiving the data (ID of the contact tag B) transmitted from the contact tag B by contact communication, stores the received data (ID of the contact tag B) together with a contact reception FG indicating that the data has been received by contact communication as a first item of the communication list of its own (the contact tag A).

Next, when the data (ID of the contact tag A) is transmitted from the contact tag A to the contact tag B, the data is stored in a storage manner of the same sort as a second item of the communication list of the contact tag A and as a second item of the communication list of the contact tag B.

Next, when contact is lost and contact communication can no longer be performed, a contact end FG indicating the end of contact communication is stored as a third item of both communication list. Since contact communication is performed among a plurality of contact tags, the transmission/reception mode is switched over several times. If reception could not have been performed for several consecutive times, contact communication is determined to have completed. A lamp or a buzzer is operated. Furthermore, if the times to ring the buzzer or the times to light the lamp depend on the number of the contact tags of the other ends of contact communication, it can be useful for human to confirm whether contact communication is actually performed in all the contact paths on the contact path.

Based on the case of FIG. 35(C) above, a storage example of the communication lists when contact communication is performed between the contact tag A and the contact tag B both with clock, for example as shown in FIG. 35(A). Firstly, the contact tag B transmits its own ID (ID of the contact tag B) and the current time. At this time, in the contact tag B, the transmitted data (time and its own ID) is stored as a first item of its own communication list together with a contact transmission FG. At this time, the contact tag A receives the transmitted data (time and ID of the contact tag B). In the contact tag A, the transmitted data (time and ID of the contact tag B) is stored as a first item of its own communication list together with the current time from the clock provided in the contact tag A and a contact reception FG.

Next, in case that data is transmitted from the contact tag A to the contact tag B, storage is made as a second item of both communication lists in the same manner.

Next, when there is no contact and contact communication is unable to be performed, a contact end FG indicating the end of contact communication is stored as a third item of both communication lists.

Next, in FIG. 35(B), explanation is given on contact communication in case that only one of the contact tags is provided with clock. This communication is basically the same communication as the communication in FIG. 35(A). However, since the contact tag B is not provided with clock, the contact tag B cannot transmit time or store data together with reception time by contact communication. Nevertheless, since the contact tag A transmits transmission time at the time of contact transmission, it is possible to store the time as reception data as in a second item of the communication list of the contact tag B. In this manner, time can be obtained from the other end of contact communication, and time of contact communication is known. The time can be utilized in various determinations in later explained control flows.

Figure 29:
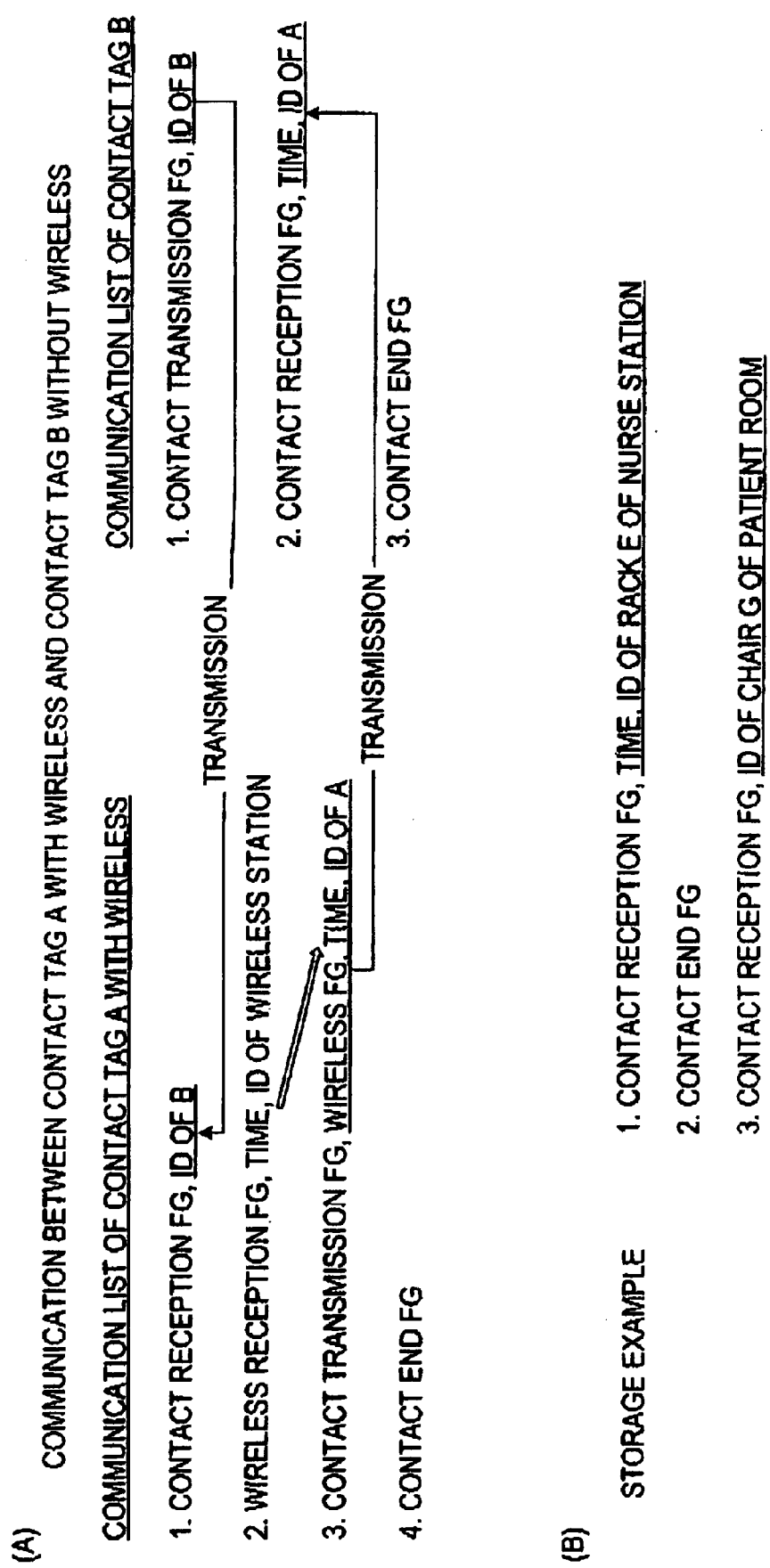
FIG. 29 is an explanatory view showing a generation process of a communication list and its storage example.

As shown in FIG. 36(C), in case that contact communication is performed between contact tags both without clock, neither transmission nor reception of time is possible. Thus, no time can be stored on communication lists. However, even in the case of contact communication between contact tags without clock, if one of the contact tags is provided with the wireless communication portion 23 or a wired LAN communication device as shown in FIG. 29, time can be obtained therefrom. That is, during contact communication or by wireless communication immediately after contact communication, time may be received from the wireless station. Thereby, time when contact communication has been performed can be known.

For example, as in FIG. 29(A), during contact communication, a wireless contact tag A wirelessly receives time and the ID of the wireless station 61 from the wireless station 61 as reception data. The reception data is stored as a second item of the communication list of its own (contact tag A), together with a wireless reception FG indicating that the data has been received wirelessly.

Moreover, in case that the wirelessly received time is transmitted to the other tags by contact communication, the time received from the wireless station, a wireless FG indicating that the time is wirelessly obtained, and its own ID (ID of the contact tag A) are transmitted in contact as transmission data. The transmission data is stored as a third item of the communication list of its own (contact tag A), together with a contact S transmission FG. The contact tag B which has received the data stores the received data (wireless FG, time, ID of the contact tag A) as a second item of the communication list of its own (contact tag B), together with a contact reception FG.

In this manner, the contact tag B neither with clock nor wireless/wired LAN is also able to obtain time. In case that the wirelessly received time is transmitted, the time data is transmitted with a wireless flag (wireless FG) in the present embodiment since the time is not necessarily a correct time. Also, as in the second item of the communication list of the contact tag A, time with a wireless reception FG or the wireless station ID is determined as time wirelessly obtained. Also, in the case of transmission by wireless communication, the transmitted data is stored on its own communication list together with a wireless transmission FG. By means of these FGs, it is possible to determine whether the data is obtained by contact communication or wirelessly.

As to selection of the aforementioned operation modes (transmission mode, suspension mode, and reception mode), it is preferable that probability of selecting the transmission mode is high in the contact tag with clock. Thereby, chances of transmitting time data are increased. The contact tag without clock is easy to obtain chances of obtaining time data.

FIG. 29(A) explains a manner of wirelessly obtaining time of contact communication. However, as in FIG. 29(B), time when contact communication has been performed may be estimated from place data described on the communication list. In case that there is description on the communication list as in FIG. 29(B), a nurse station is identified from the ID of the rack E of the nurse station, and a patient room is identified from the ID of the chair G of the patient room. Then, based on the inside hospital standard travel time list stored in the memory of the contact tag, a standard travel time between the nurse station and the patient room is obtained. The travel time is added to the time in the first item of the communication list. In this manner, the time when contact communication has been performed with respect to the third item of the communication list can be estimated.

The position of the nurse may be detected from the contact tag ID that allows specification of position. However, the position may be estimated by using the ID of the wireless station 61 at the time when wireless communication has been performed or GPS, or from the ID of apparatus having a wireless tag with which wireless communication has been performed.

Also, not the whole floor may be conductive, but, for example seams of tiles may be partially conductive and the contact tag 1 may be arranged thereon. Then, the ID of the contact tag 1 can be received, for example by the contact communication device 20. That is, the aforementioned contact path is composed only through a specified portion of the floor. The contact tag 1 is arranged at the specified portion. Thus, the ID of the contact tag 1 can be received, for example by the contact communication device 20, so as to detect the position of the nurse, etc.

Figure 30:
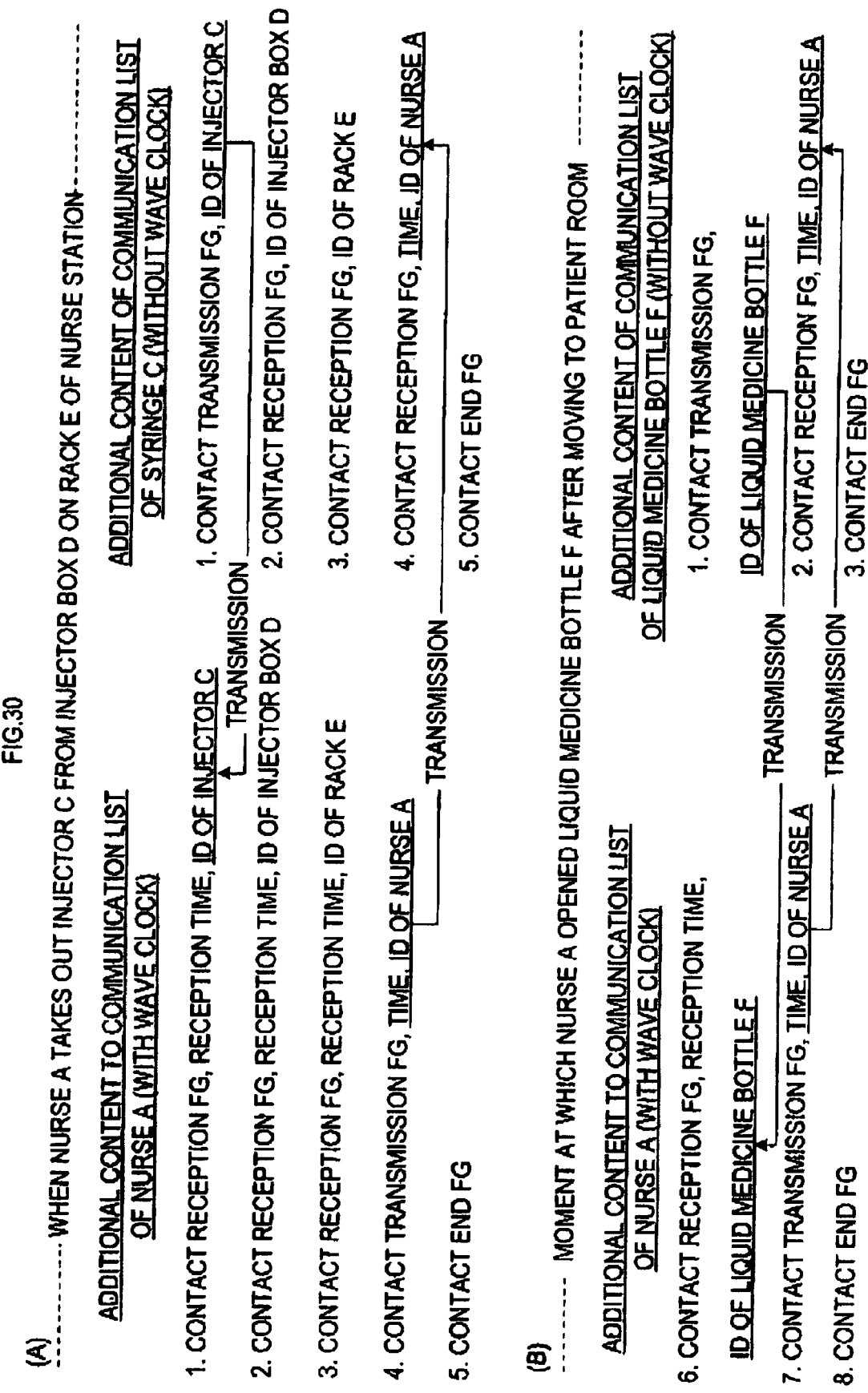
FIG. 30 is an explanatory view showing another storage example of the communication list.
Figure 31:
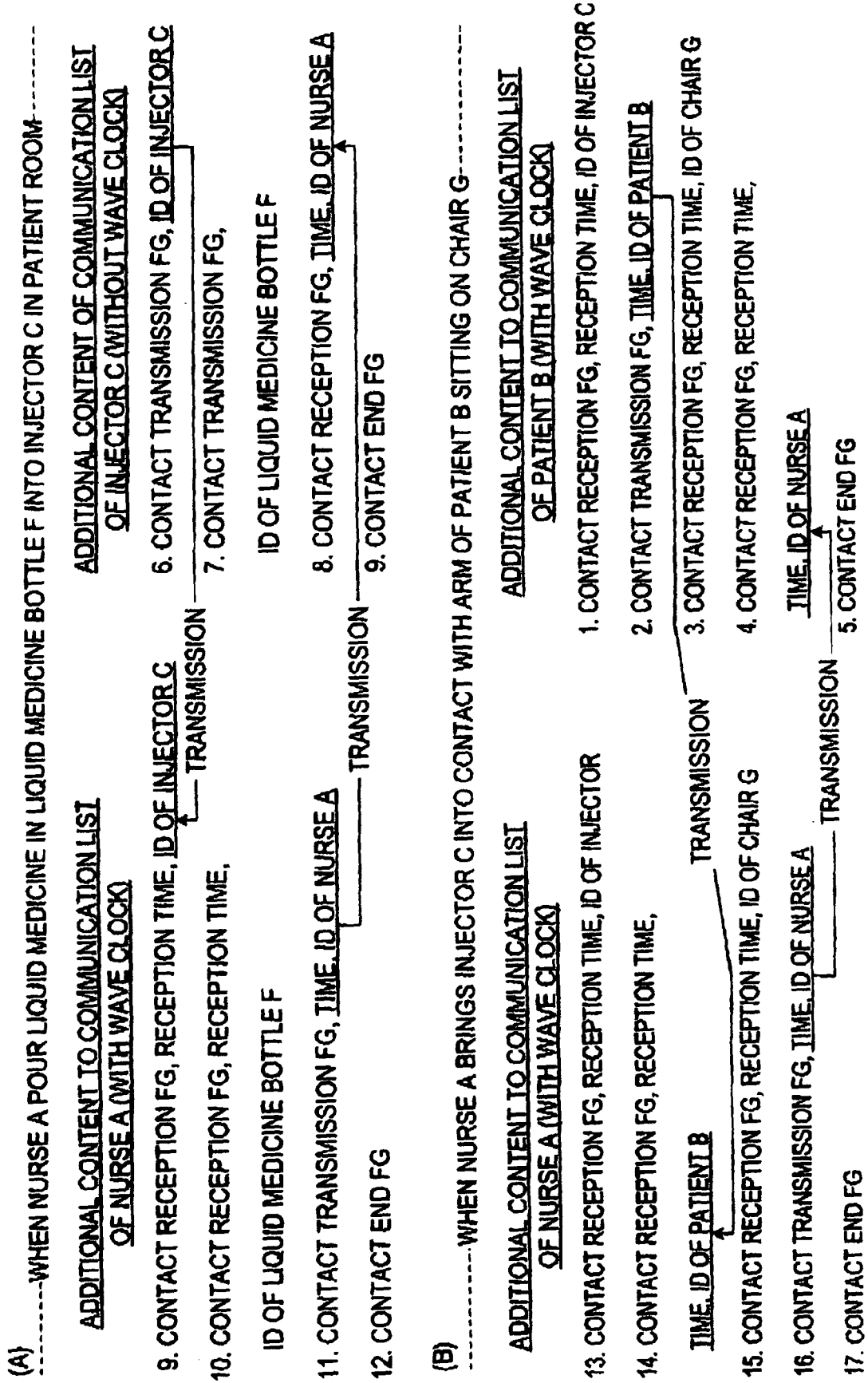
FIG. 31 is an explanatory view showing further another storage example of the communication list.

Here, explanation is given, by way of FIGS. 30 and 31, on a storage example of memory of a communication list at the time when a series of medical treatment is continuously performed until the nurse A gives the patient B an injection as shown in FIG. 15, and FIG. 21 to FIG. 23. FIG. 30(A), as in FIG. 15, shows the communication list of the nurse A at the time when the nurse A has taken out the injector C from the injector box D on the rack E in a nurse station, and a communication list of one of the other ends of communication, the injector C. FIG. 30(B), as in FIG. 21, shows the communication list of the nurse A at the time when the nurse A has opened the liquid medicine bottle F after moving into a patient room, and a communication list of one of the other ends of communication, the liquid medicine bottle F. FIG. 31(A), as in FIG. 22, shows the communication list of the nurse A at the time when the nurse A injects liquid medicine in the liquid medicine bottle F into the injector C, and a communication list of one of the other ends of communication, the injector C. FIG. 31(B), as in FIG. 23, shows the communication list of the nurse A at the time when the nurse A has brought the injector C into contact with the arm of the patient B sitting on the chair G, and a communication list of one of the other ends of communication, the patient B.

In FIGS. 30 and 31, explanation is given, setting out the communication list of the nurse A on the left side, and the communication list of one of the other ends of communication on the right side. The others of the other ends of communication are omitted. Each underlined portion on the communication list in FIG. 30(A) indicates transmission data or reception data. The direction of transmission is described by an arrow from the contact tag on the transmission side to the contact tag on the reception side. The same applies to the other communication lists. For example, two underlined portions and an arrow in FIG. 30(A) indicate that the ID of the injector C has been transmitted as transmission data from the contact tag of the injector C to the contact tag of the nurse A.

Here, a determination process performed in the contact tag 1 is described in detail.

The contact tag 1 executes the human error check process and the question referral process in parallel in a time-sharing manner with respect to the communication list. The communication list stores data of medical treatment by a nurse, etc. immediately after the medical treatment is performed. Thus, medical error check and question referral can be conducted substantially simultaneously with medical treatment.

The chart computer 64, which is one type of contact communication device, performs the same procedures (the human error check process and the question referral process) with respect to inputs by a doctor from the keyboard 64*d*. As noted above, the chart computer 64 is one type of contact communication device provided with the contact tag 1. The CPU 64*a* of the chart computer 64 has a function of the CPU 7 of the contact tag 1. The memory 64*b* has a function of the memory 8 of the contact tag 1. Accordingly, the CPU 64*a* of the chart computer 64 performs the human error check process and the question referral process.

FIG. 33 is a flowchart showing the human error check process executed by the CPU 7 of the contact tag 1. When the process is started, the CPU 7 of the contact tag 1 firstly reads the communication list stored in the memory 8 in S1. At that time, each ID is converted to what is represented by the ID in reference to the ID list and read. That is, the ID of the contact tag 1*a*, the ID of the contact tag 1*c*, etc. is converted to the nurse A, the injector C, etc. and read. As noted in the explanation on the ID list, there are cases in which an ID may represent various information. For example, the ID of a liquid medicine bottle represents a variety of information such as the liquid medicine bottle itself, the state of preservation, the name of the content, the purpose of use of the liquid medicine like injection, intravenous drip, etc., a flag indicating the state like opened and not opened of the liquid medicine bottle. In such cases, explanation will be complicated if all the information represented by the ID is described. Thus, the explanation will be given in a simple manner, like the liquid medicine bottle, the liquid medicine bottle (opened), etc.

In subsequent S3, data having strong relevance in the communication list is extracted based on the relevance criteria in the aforementioned relevance criterion list to create relevant data combination. Thereby, data having strong relevance is extracted from the data in the communication list.

For example, let us take a look at the communication list of the nurse A of FIG. 30(A) to FIG. 31(B), recorded at the time when the nurse A has performed a series of medical treatment, which will be later explained in detail, in a consecutive manner. The series of the medical treatment includes procedures from when the nurse A takes the injector C out of the injector box 56 to give the patient B an injection until when the nurse A brings the needle of the injector C into contact with the patient B, as shown in FIG. 15 and FIG. 21 to FIG. 23.

The communication list of the nurse A at the time includes descriptions shown respectively on the left sides of FIG. 30(A) to FIG. 31(B). Data combination having strong relevance is extracted from the communication list if all the conditions of the aforementioned relevance criteria (1), (2), and (3) are satisfied. The extracted data combination having strong relevance is "nurse A, patient B, injector C, liquid medicine bottle F (opened), and chair G" (the details will be explained later).

Moreover, in subsequent S5, the above relevant data combination is referred to the aforementioned check lists for error check. For example, the following check will be done to the above combination of "nurse A, patient B, injector C, liquid medicine bottle F (opened), and chair G".

For example, if the liquid medicine bottle F is the liquid medicine bottle 70 filled with "xylocaine 10%", the fact that the liquid medicine bottle F contains "xylocaine 10%" is already identified at the time of reference to the ID list in S1. Since "xylocaine 10%" is for intravenous drip and not for injection, a combination of "injection xylocaine 10%" is described in one of the check lists, the medicine list, as NG keyword combination. Due to consistency with NG keyword combination, the above combination is determined as NG.

Also, in reference to one of the check lists, the chart, there are instructions for "xylocaine 2%" but there are no instructions for "xylocaine 10%". Thus, the above combination is determined as NG. Moreover, in reference to one of the check lists, the human error list, the combination of "xylocaine 10% and injection is registered as an example of NG. Thus, the above combination is determined as NG even based on the human error list. Synonyms are included in the above check lists in determination of keyword correspondence. For example, the "injector" corresponds to "injection" stored in the chart.

In S7 following S5, in response to the above check results in S5, notification and recording are performed. If the extracted combination corresponds to the above NG keyword combination, warning is given. The results of determination (OK, NG, or unknown) are notified by voice or on display, etc. The results are stored in the check result list. For example, in the above example, if the liquid medicine bottle F contains "xylocaine 10%", the extracted combination is determined as NG. Then, warning is given. In this manner, as in FIG. 23, immediately after the nurse A brings the injector C into contact with the patient B, warning can be given to avoid medical error. Moreover, in case that there is high level of risk, NG level is determined as high so that the results of determination may be notified to the other devices. Then, emergency contact can be immediately done, for example to the other doctors.

In subsequent S9, it is determined whether the process is END. If not END (S9: NO), the steps from the above S1 are again repeated. If the process is END (S9: YES), the process is ended.

Here, the extraction method of relevant data combination in the above S3 is more particularly explained. Explanation is given with respect to the communication list of the contact communication device of the nurse A described respectively on the left sides of FIG. 30(A) to FIG. 31(B).

The data upon simultaneous contact in the reference criterion (1) can be determined from a contact end FG, the separator. The contact end FG is recorded at the point when a contact state has been changed to a non-contact state. That is, data in contact communication in a range from data in contact communication after one contact end FG to prior to the next contact end FG can be determined as data in simultaneous contact. Thereby, when extraction is performed by means of the relevance criterion (1) from the communication list of the contact communication device of the nurse A, the items 1 to 4 in FIG. 30(A), the items 6 to 7 in FIG. 30(B), the items 9 to 11 in FIG. 31(A), and the items 13 to 16 in FIG. 31(B), respectively, can be determined as data in simultaneous contact. That is, a combination A of "nurse A, injector C, injector box D and rack E" in the items 1 to 4, a combination B of "nurse A and liquid medicine bottle F (opened)" in the items 6 to 7, a combination C of "nurse A, injector C, and liquid medicine bottle F (opened)" in the items 9 to 11, and a combination D of "nurse A, injector C, patient B and chair G" in the items 13 to 16 are extracted. Data in each combination is determined as data in simultaneous contact.

Next, by means of the reference criterion (2), combination having higher relevance is further extracted out of the four combinations extracted above. Here, let us assume that it takes six minutes for the nurse A to travel to the patient room A, and it takes less than five minutes from when the nurse A opens the liquid medicine bottle F in the patient room A until when the nurse A attempts to give the patient B an injection. Then, between the items 4 and 6 in the communication list of the nurse A, more than five minutes have passed. As the combination of data in contact communication in less than five minutes, the combinations B, C and D, excluding the combination A, are extracted to be determined as data combination having stronger relevance.

Moreover, by means of the relevance criterion (3), relevance among the above three combinations is determined as follows The combinations B and C include identical data, that is the nurse A and the liquid medicine bottle F. Thus, strong relevance is determined. The combinations C and D include identical data, that is the nurse A and the injector C. Thus, strong relevance is determined. Since the combinations B and C have high relevance and the combinations C and D have high relevance, the combinations B, C and D are collectively determined to have strong relevance in the end. In this manner, data of the combination B, the combination C and the combination D, that is "nurse A, patient B, injector C, liquid medicine bottle F (opened), and chair G", are extracted as data combination having high relevance in the end.

In the above S3, the relevant data combination is created based on relatively physical elements like time proximity. However, the relevance criteria may be modified depending on characteristics of what is identified by the ID. For example, only those directly related to medical services such as medical staff, medical equipment, medicine, etc. may be targeted for determination by the relevance criteria. Then, the IDs for the rack E and the injector box D can be ignored. Also, since "xylocaine 10%" for intravenous drip is to be fed into specific instruments like the injector 50 and the intravenous bottle 91, such instruments may be associated as data having stronger relevance.

Next, FIG. 34 is a flowchart showing the question referral process executed by the CPU 7 of the contact tag 1 in parallel to the aforementioned human error check process. In this flow, as noted above, whether or not there is any human error cannot be determined as in the human error check process. However, a question of whether there is any probability of error can be checked. When the process is started, the CPU 7 of the contact tag 1 firstly reads the communication list inputted, for example by contact communication, to detect the currently working item, in S11. For example, when a nurse has opened the liquid medicine bottle 70 containing "Taxol", the ID of the contact tag 1f of the liquid medicine bottle 70 is detected by contact communication to be stored on the communication list. This communication list is read to detect the ID of the current working item. Instead, the ID of old data on the communication list may be read so that the process is executed with respect to the ID.

Also, when a doctor has entered "SUZUKI Ji(Ji)ro" from the keyboard 64d of the chart computer 64, the input data is detected by the CPU of the chart computer 64.

In subsequent S13, the item detected by the ID among the currently working items detected above is converted to what is represented by the ID to be identified. In case that the doctor has directly entered the patient name, etc. from the keyboard 64d of the chart computer 64, the present step that identifies the patient from the patient ID is not necessary. Thus, the process moves to the next step of S15. In S15, what is detected in S11 or identified in S13 is referred to the question referral list. In subsequent S17, results of the question referral are notified by voice or on display. The results are stored on the question referral result list.

In subsequent S19, whether the process is END is determined. If not END (S19: NO), the steps are again repeated from the above S11. If there is an input of END (S19: YES), the process is ended.

For example, a nurse opens the liquid medicine bottle 70 containing "Taxol". The contact communication device 20 of the nurse has detected the ID of the liquid medicine bottle 70 by contact communication, so that the ID is already stored as data on the communication list. The contact communication device 20 of the nurse detects the ID of the liquid medicine bottle 70 from this communication list in S11. Next, in S13, the content of the liquid medicine bottle 70 is identified as "Taxol" from the ID of liquid medicine bottle 70. Moreover, in S15, when question referral is made with respect to "Taxol", "Taxol" is found in the combination list of "Taxol and Taxotere" registered as easily mistaken medicine in the question referral list. In S17, notification is given such that "Not Taxol but Taxotere?"

Also, when a doctor enters "SUZUKI Ji(Ji)ro" from the keyboard 64d of the chart computer 64, a similar process is performed. That is, in S11, the chart computer 64 detects "SUZUKI Ji(Ji)ro" entered from the keyboard 64d. Since "SUZUKI Ji(Ji)ro" is already acknowledged and no ID identification is necessary, the process moves to next S15. In S15, since "SUZUKI Ji(Ji)ro" is found in "SUZUKI Ji(Ni)ro, SUZUKI Ji(Ji)ro" registered as easily mistaken patients in the question referral list, notification is given such that "Not SUZUKI Ji(Ji)ro but SUZUKI Ji(Ni)ro?"

In this process, other than the ease in which easily mistaken keywords are combined, important medicine is listed. If the important medicine is detected, notification is given. In this manner, in the present embodiment, cases with high probability of human error in medical fields can be checked in advance.

The human error check process and the question referral process may be collectively performed by the chart computer 64. However, as noted above, the memory 8 of each contact tag 1 stores the aforementioned ID list, communication list, relevance criterion list, check lists including the medicine list, the chart, and the human error list, check result list, question referral list, question referral result list, inside-hospital travel time list, etc. The above processes are performed in each contact tag 1. In this manner, the contact communication device born by a nurse, a doctor, etc. or the medical instrument provided with the contact tag 1 itself gives warning. Accordingly, medical error can be promptly avoided. Also, time for LAN communication or communication failure is no longer necessary to be taken into account. Thus, faster check can be performed.

From now on, an application example to a pharmacy will be explained. This pharmacy is the aforementioned pharmacy inside hospital. The contact communication device described in this application example to the pharmacy is capable of being communicated with the aforementioned hospital LAN, for example wirelessly. Also, various devices like the scale 260, a prescription computer 220, etc. are included in the contact communication device.

Figure 36:
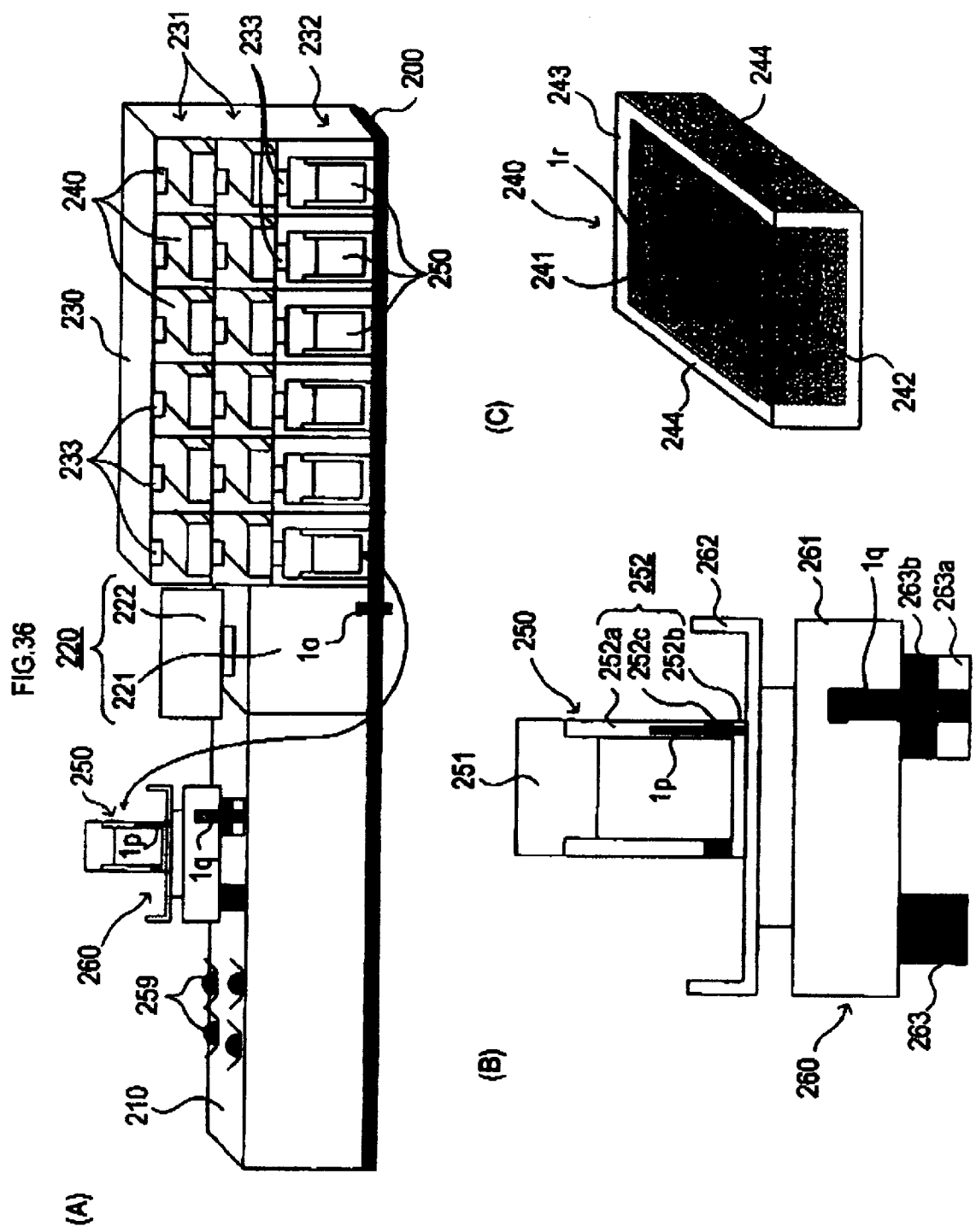
FIG. 36 is an explanatory view showing an application example of the present invention to a pharmacy, in which (A) shows an overall structure, (B) shows structures of a powdered medicine bottle and a scale, and (C) shows a structure of a medicine case, respectively.

FIG. 36(A) to FIG. 40 are explanatory views showing the application example to the pharmacy. As shown in FIG. 36(A), this pharmacy is provided with a dispensing table 210, the prescription computer 220, and a medicine rack 230 on an insulating board 200. In this embodiment as well, a pharmacist bears the contact communication device 20 similar to the one noted above.

Each of the dispensing table 210, the prescription computer 220, and the medicine rack 230 is provided with a surface composed of conductive material. The dispensing table 210, the prescription computer 220, and the medicine rack 230 are arranged in contact with each other, centering around the prescription computer 220. Between the surface of the prescription computer 220 and the conductive floor, a contact tag $1o$ is arranged across the board 200. The prescription computer 220 includes a display portion 222 on a body 221. This display portion 222 is in the form of touch panel.

The medicine rack 230 is provided with a two-tier medicine case storage portion 231 above and a one-tier powdered medicine bottle storage portion 232 below. The medicine case storage portion 231 stores a medicine case 240, and the powdered medicine bottle storage portion 232 stores a powdered medicine bottle 250. Also, the medicine case storage portion 231 and the powdered medicine bottle storage portion 232 is provided with an indicator 233 for showing information of medicine stored in each portion. The dispensing table 210 is designed such that a powdered medicine 259 can be dispensed on the upper surface. The scale 260 is mounted on the dispensing table 210.

FIG. 36(B) is an explanatory view showing in detail structures of the powdered medicine bottle 250 and the scale 260. The powdered medicine bottle 250 and the scale 260 are composed in a manner similar to the aforementioned tablet bottle 80 and the scale 85. That is, the powdered medicine bottle 250 is provided with a lid 251 and a container body 252. Almost all the powdered medicine bottle 250 is composed of conductive material. However, a side wall portion 252a and a bottom board portion 252b of the container body 252 are insulated by an insulating portion 252c. Across the insulating portion 252c, a contact tag $1p$ is embedded between the side wall portion 252a and the bottom board portion 252b.

The scale 260 is provided on a body 261 with a scalepan 262 which can mount the powdered medicine bottle 250 thereon. Three out of four legs 263 supporting the body 261 are composed of insulating material. One leg 263a is composed of conductive material except for a base 263b. Across this base 263b, a contact tag $1q$ is embedded between the tip of the leg 263a and the body 261.

FIG. 36(C) is an explanatory view showing a structure of the medicine case 240. In FIG. 36(C), conductive portions are indicated with hatching. This medicine case 240 has a known box-like shape which includes a front plate 242, a back plate 243, and a pair of side plates 244 standing on the periphery of a rectangular bottom plate 241. A contact tag $1r$ is embedded in the bottom plate 241. The inner surface of the medicine case 240 and the outer surface of the front plate 242 are electrically conducted to each other to be electrically conducted to one electrode of the contact tag $1r$. The bottom plate 241, the back plate 243, and the outer surface of the side plates 244 are electrically conducted to each other to be electrically conducted to the other electrode of the contact tag $1r$.

Figure 37:
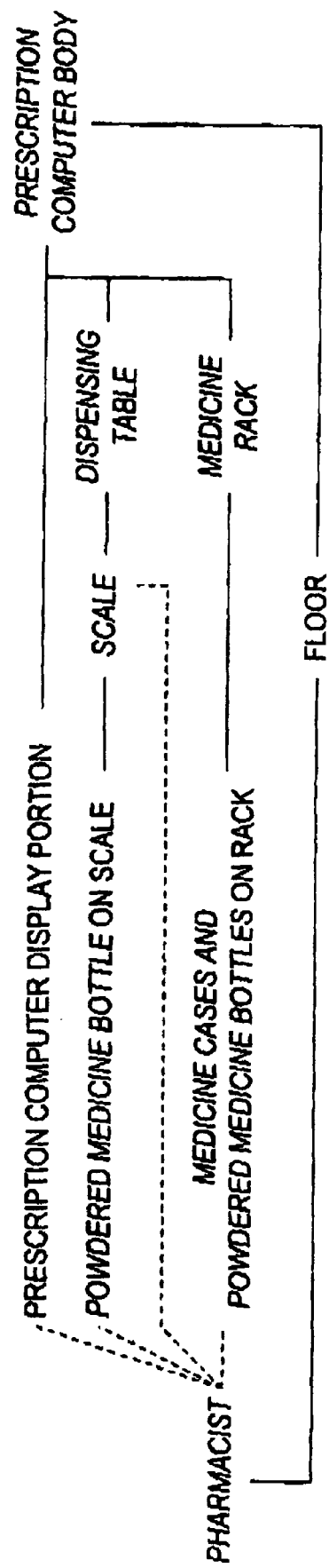
FIG. 37 is an explanatory view schematically showing a contact path created in the application example.

Accordingly, various contact paths are created, and contact communication is conducted through the paths as follows. FIG. 37 schematically shows each contact path for reference. That is, when a pharmacist touches the display portion 222 of the prescription computer 220, a contact path is created which passes through the pharmacist's body→the display portion 222→the body 221→the contact tag $1o$→the floor→the pharmacist's body. When the pharmacist touches the medicine case 240 stored in the medicine rack 230, a contact path is created which passes through the pharmacist's body→the front plate 242→the inner surface of the bottom plate 241→the contact tag $1r$→the bottom plate 241 or the outer surface of the side plates 244→the medicine rack 230→the body 221 of the prescription computer 220→the contact tag $1o$→the floor→the pharmacist's body. When the pharmacist touches the powdered medicine bottle 250 stored in the medicine rack 230, a contact path is created which passes through the pharmacist's body→the side wall portion 252a→the contact tag $1p$→the bottom plate portion 252b→the medicine rack 230→the body 221 of the prescription computer 220→the contact tag $1o$→the floor→the pharmacist's body. Moreover, when the pharmacist places the powdered medicine bottle 250 on the scale 260, a contact path is created which passes through the pharmacist's body→the side wall portion 252a→the contact tag $1p$→the bottom plate portion 252b→the scalepan 262→the body 261→the contact tag $1q$→the tip of the leg 263a→the dispensing table 210→the body 221 of the prescription computer 220→the contact tag $1o$→the floor→the pharmacist's body.

Figure 38:
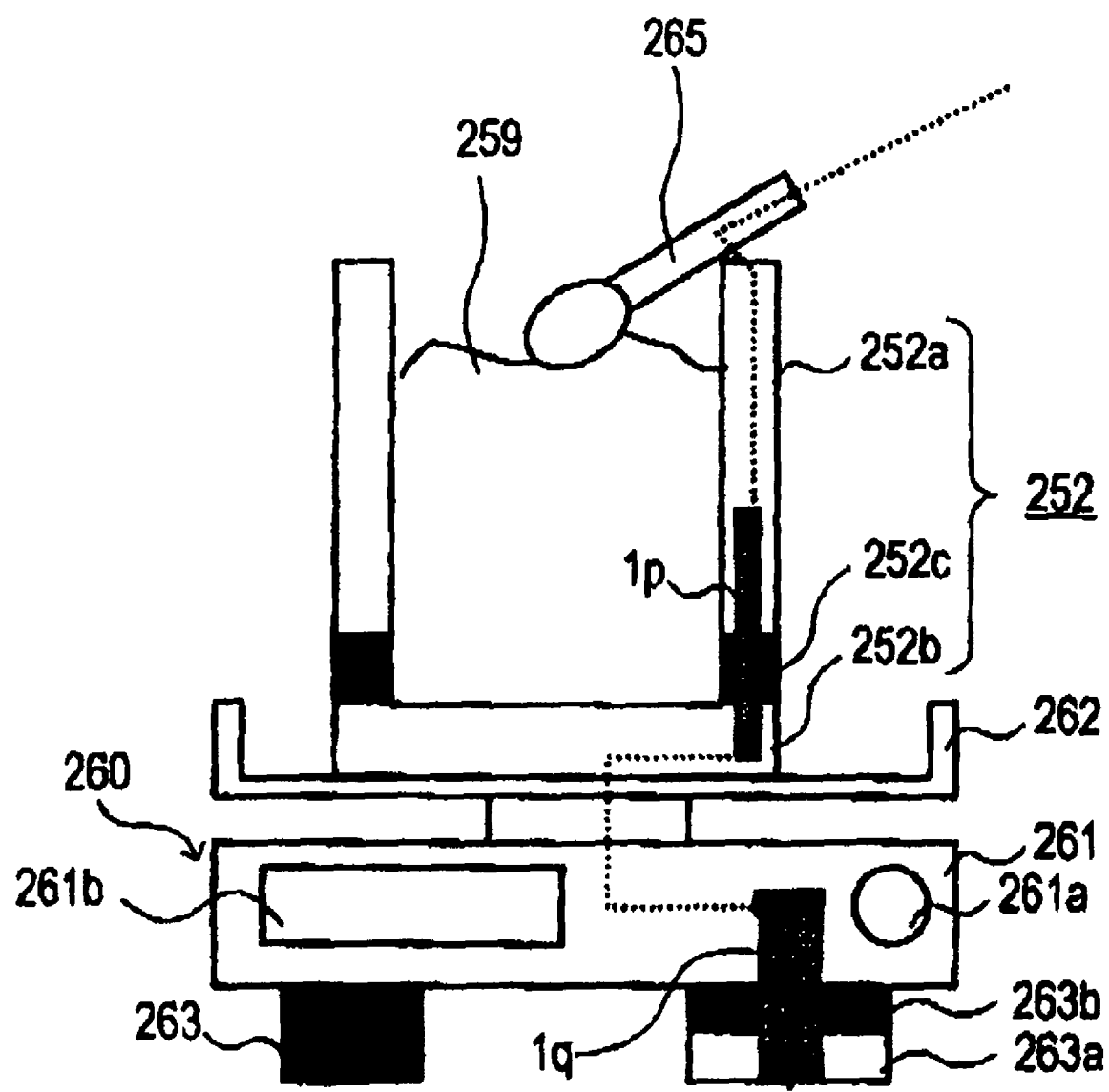
FIG. 38 is an explanatory view illustrating a contact path via the powdered medicine bottle and the scale.
Figure 39:
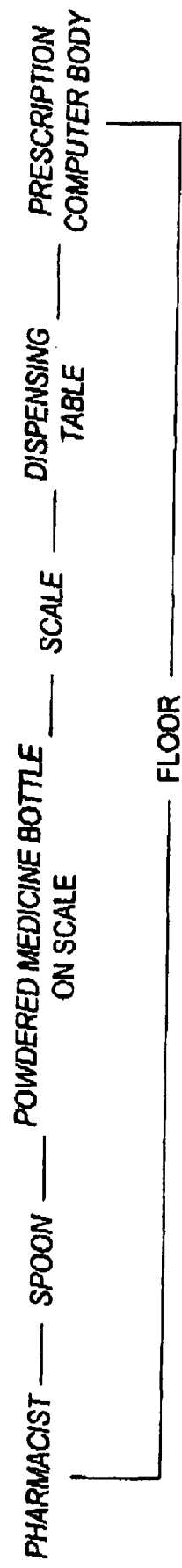
FIG. 39 is an explanatory view schematically showing the contact path.

A dispensing spoon 265 is also composed of conductive material. As shown in FIGS. 38 and 39, as the spoon 265 touches the side wall portion 252a of the powdered medicine bottle 260 mounted on the scale 260, a contact path is created which passes through the pharmacist's body→the spoon 265→the side wall portion 262a→the contact tag $1p$→the bottom plate portion 252b→the scalepan 262→the body 261→the contact tag $1q$→the tip of the leg 263a→the dispensing table 210→the body 221 of the prescription computer 220→the contact tag $1o$→the floor→the pharmacist's body. As shown in FIG. 38, a reset button 261a and a display portion 261b are provided at the front of the body 261 of the scale 260.

Figure 40:
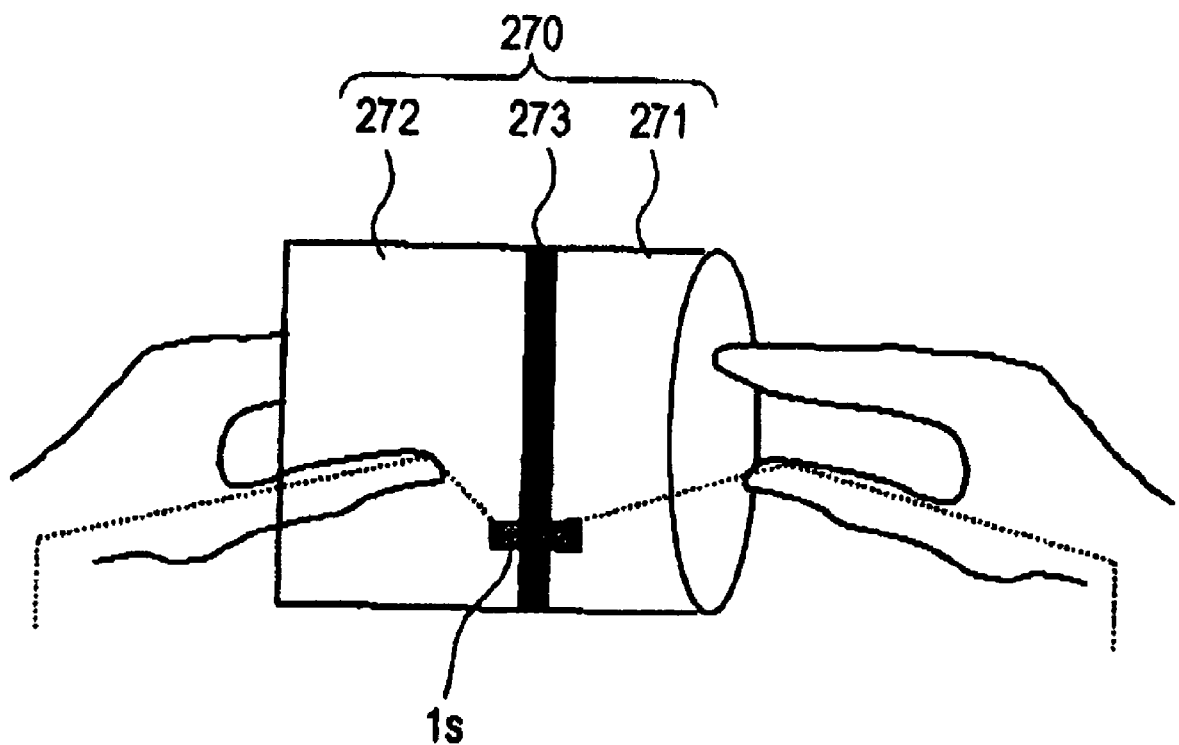
FIG. 40 is an explanatory view showing a structure of a medicine bag in the aforementioned application example to the pharmacy.

Similar to a known medicine bag, the medicine bag 270 for delivering medicine to a patient is opened at one end 271 and closed at the other end 272 as shown in FIG. 40. The ends 271 and 272 are composed of conductive material, and an insulating portion 273 is provided therebetween. Across the insulating portion 273, a contact tag 1s is arranged to connect the one end 271 and the other end 272. Accordingly, when the pharmacist touches both ends of the medicine bag 270, a contact path is created which passes through the pharmacist's body→the one end 271→the contact tag 1s→the other end 272→the pharmacist's body.

Next, each process executed at this pharmacy will be explained.

When the pharmacist turns ON the prescription computer 220, the prescription computer 220 communicates with the central computer 62 and a prescription of a patient to be treated is displayed on the display portion 222. Also, the prescription is transmitted to the contact communication device 20 born by the pharmacist. If necessary, the prescription is transmitted to the scale 260. The aforementioned transmission may be conducted by contact communication by the pharmacist touching the prescription computer 220 and the scale 260, or by wireless communication.

Figure 41:
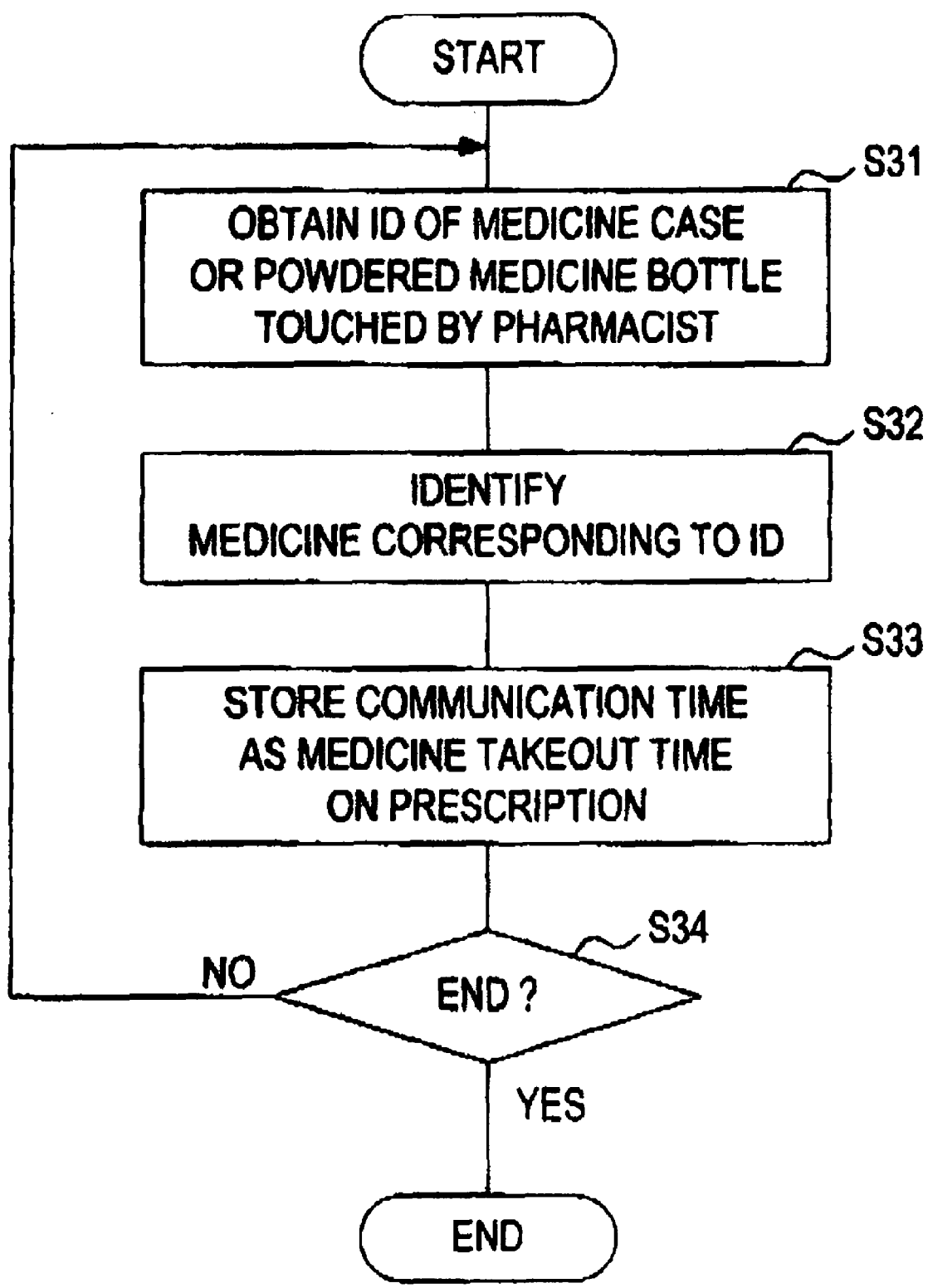
FIG. 41 is a flowchart showing a takeout medicine detection process executed by a prescription computer in the application example.
Figure 42:
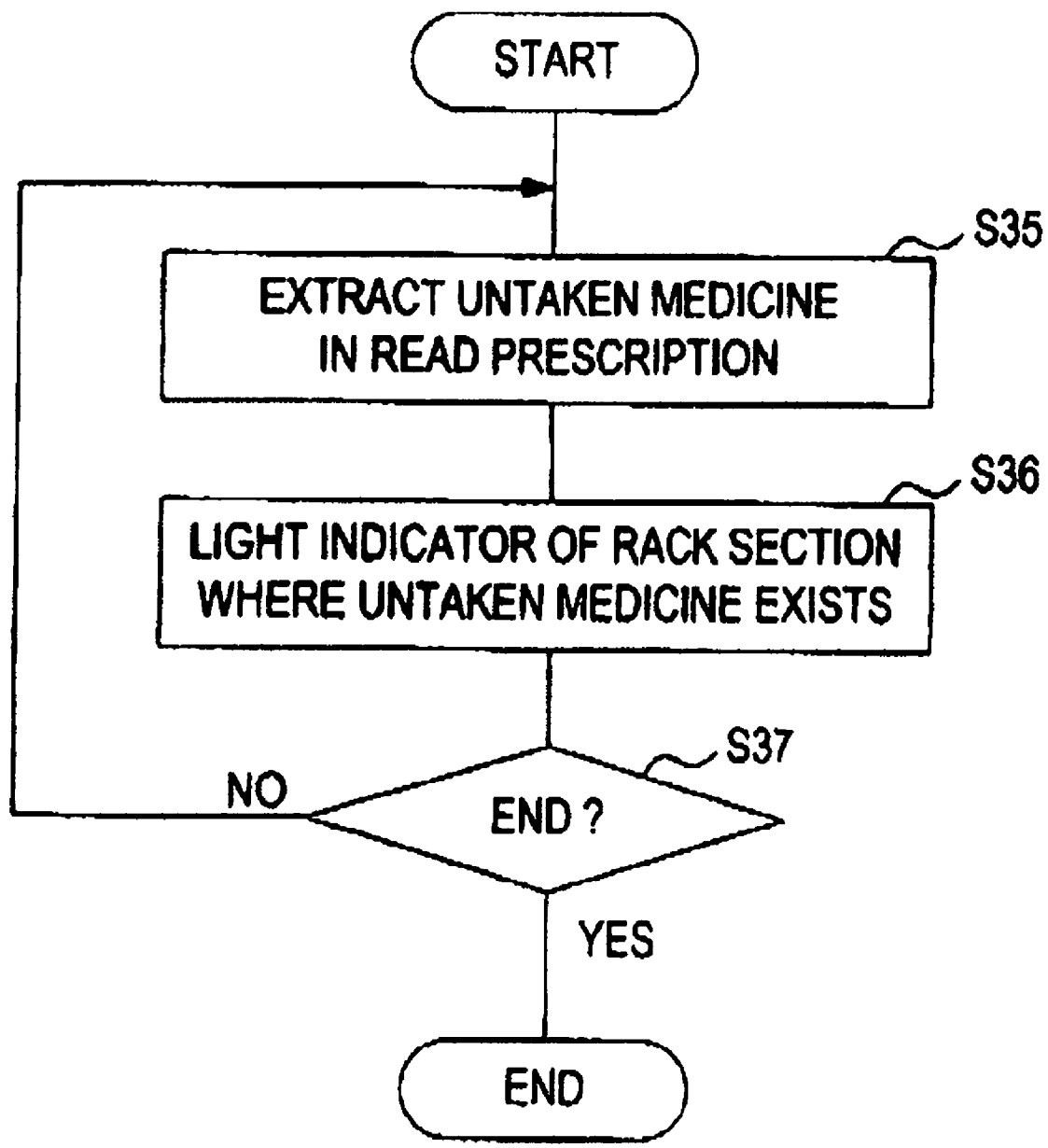
FIG. 42 is a flowchart showing an indicator control process executed by the prescription computer.
Figure 44:
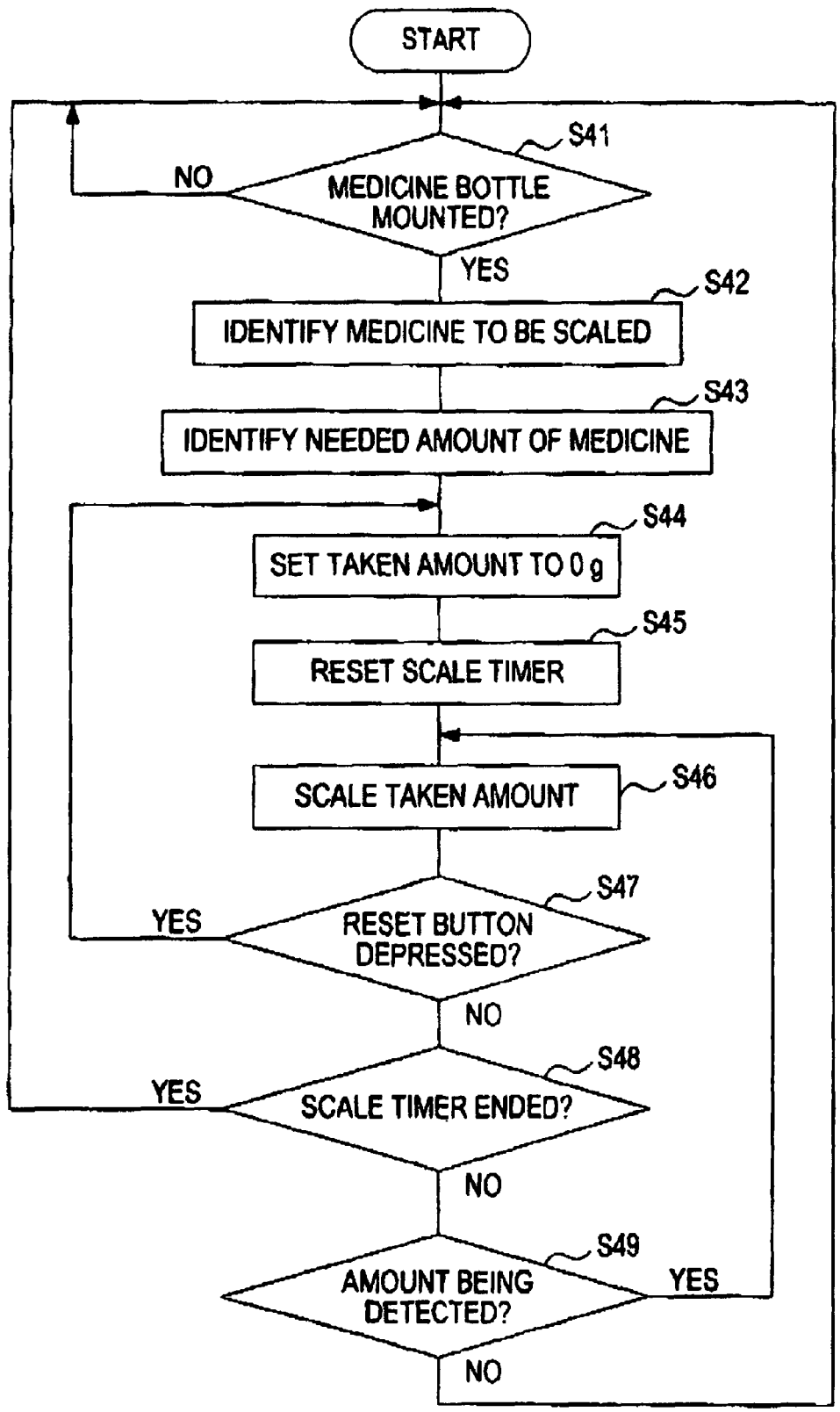
FIG. 44 is a flowchart showing a scaling process executed by a microcomputer of the aforementioned scale.

The contact communication device 20 of the pharmacist and the prescription computer 220 perform procedures as shown in FIG. 41. The prescription computer 220 performs procedures as shown in FIG. 42. The scale 260 performs procedures as shown in FIG. 44. These procedures are processed in parallel and information is exchanged at all times. Thereby, medicine prescribed to one patient can be collected without mistake. When the collected medicine is put into the medicine bag 270 of FIG. 40, the contact communication device 20 of the pharmacist performs procedures of FIG. 45. Then, prescription of medicine for one patient is ended, and the process moves to prescription of medicine for the next patient.

The contact communication device 20 of the pharmacist, the prescription computer 220, and the later explained scale 260 communicate with each other wirelessly or by contact communication so as to update working prescription to the latest at all times. Also, the contact communication device 20 of the pharmacist, the prescription computer 220, and the scale 260 communicate with the central computer 62 via the inside hospital LAN for update to the latest.

FIG. 41 is a flowchart showing a takeout medicine detection process for detecting medicine taken out from the medicine rack 230. The process is executed by the contact communication device 20 of the pharmacist and the prescription computer 220. When the process is started, in S31, whether the pharmacist has touched the medicine case 240 or the powdered medicine bottle 260 stored in the medicine rack 230 is detected by contact communication. The ID of the medicine case 240 or the powdered medicine bottle 250 taken out is obtained by contact communication. As mentioned above, this becomes possible by designing the medicine rack 230 to detect medicine taken out by contact communication with the contact communication device 20 of the pharmacist.

In subsequent S32, medicine corresponding to the ID is identified. When the medicine is identified, time when the above ID has performed contact communication is stored in the working prescription as the medicine takeout time in S33. At this time, the name of the pharmacist is also stored in the prescription.

In subsequent S34, it is determined whether the process is END, for example by shut down of the contact communication device 20 of the pharmacist or the prescription computer 220. If not END (S34: NO), the process moves to S31 and the aforementioned steps are repeated. If END (S34: YES), the process is once ended.

Next, FIG. 42 is a flowchart showing an indicator control process for controlling the indicator 233 of the medicine rack 230. The process is executed by the prescription computer 220. In S35, untaken medicine which is not yet taken from the medicine rack 280 is extracted from the working prescription. In this step, all the medicine described in the prescription is extracted at first. However, every time the medicine taken out from the medicine rack 230 is detected by the aforementioned takeout medicine detection process (FIG. 41), the number of medicine extracted in this step is reduced. Whether or not the medicine is untaken can be determined on whether or not the medicine takeout time in the prescription is blank (see FIG. 33).

In subsequent S36, an indicator 333 is lighted which is provided in a rack section where there is untaken medicine. In this step, if there are instructions on the number of medicine in the prescription, the number is displayed in the indicator 333. Moreover, in subsequent S37, whether the process is END, for example by shut down of the prescription computer 220. If not END (S37: NO), the process moves to S35 and the aforementioned steps are repeated. If END (S37: YES), the process is once ended.

Figure 43:
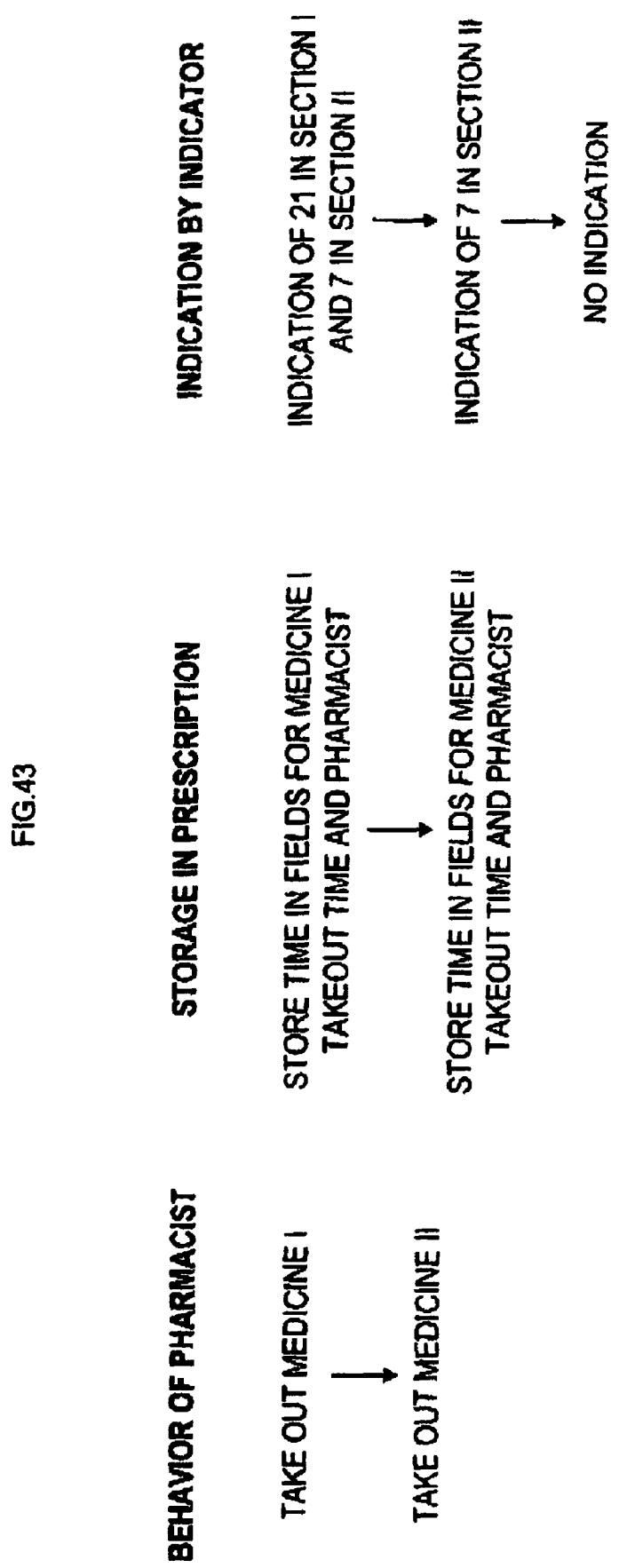
FIG. 43 is an explanatory view illustrating change in the prescription and the indicator in accordance with behavior of a pharmacist.

By the processes of FIGS. 41 and 42, for example, if it is necessary to take out twenty-one medicines I and seven medicines II stored in respective rack sections I and II, storage in the prescription and display on the indicator 33 are changed as shown in FIG. 43, depending on behavior of the pharmacist.

Next, a case that necessitates scaling, like the case of powdered medicine, will be explained. A scaling flowchart of FIG. 44 explains a case of taking out a powdered bottle containing powdered medicine and scaling by mounting the powdered bottle on the scale 260 as in FIG. 38.

FIG. 44 is the scaling flowchart showing a scaling process executed by a CPU of the scale 260 when a pharmacist mounts the powdered medicine bottle 250 on the scalepan 262 of the scale 260 and preparing medicine while scaling. The CPU of the scale 260 starts this process when the power of the scale 260 is turned ON. When power is turned OFF, the process is ended. The scale 260 is one type of contact communication device. Thus, the CPU of the scale 260 has a function as the CPU 7 of the contact tag. Also, a memory of the scale 260 has a function as the memory 8 of the contact tag.

Firstly in S41, whether the powdered medicine bottle 250 is placed (mounted) on the scalepan 262 is determined. This can be detected as below, as in FIG. 38. That is, when the pharmacist places the powdered medicine bottle 260 on the scalepan 262, a contact path is created via the pharmacist. Via the contact path, the contact tag 1q of the scale 260, the contact tag 1p of the powdered medicine bottle 250, and the contact communication device of the pharmacist perform contact communication.

If the powdered medicine bottle 260 is not placed on the scalepan 262 (S41: NO), the process stands by in S41. When it is determined that the powdered medicine bottle 250 is placed on the scalepan 262 (S41: YES), the process moves to S42.

In S42, from the ID of the powdered medicine bottle 250 obtained by contact communication with the contact tag 1p, the scaled medicine is identified. In subsequent S43, the prescription is referred to specify the necessary amount of the medicine.

In subsequent S44, a taken amount is set to 0 g. The following indication is made on the display portion 261b. That is, until the weight scaled by the scale 260 is stabled, an indication of "NO TAKEN" is shown on the display portion 261b. After the weight is stabled, the taken amount at that point is set to 0 g. Indication on the display portion 261b is changed to "TAKEN AMOUNT 0 g". That is, at the time when the powdered medicine bottle 250 is put on the scale 260, the taken amount of the powdered medicine is set to 0 g.

Subsequently, a scale timer is reset and restarted in S45. At the same time, notification enabling takeout of the powdered medicine is given by voice and on display.

In subsequent S46, each time the weight is stabled after takeout of the powdered medicine by the pharmacist, the taken amount is scaled. Excess or deficient amount is calculated from the taken amount and the needed amount specified in S43, and displayed on the display portion 261b. Even in case that the taken amount and the needed amount are completely consistent, the consistency is notified by voice and on display.

In subsequent S47, S48 and S49, whether or not the reset button 261a has been depressed, whether or not the scale timer has measured predetermined time and is ended, or whether or not the detection of weight, for example of the powdered medicine bottle 250, is continued, are sequentially determined. If the reset button 261a is not depressed (S47: NO), the scale timer is not ended (S48: NO), and detection of weight, for example of the powdered medicine bottle 250, is continued (S49: YES), the process returns to S46. The steps from S46 to S49 are repeated to continue scaling of the taken amount.

While the steps from S46 to S49 are repeated as such, if the reset button 261a is depressed (S47: YES), the aforementioned steps from S44 are repeated. This is the case of subdividing the same medicine to a plurality per the above needed amount.

On the other hand, while the steps from S46 to S49 are repeated, if the powdered medicine bottle is removed from the scalepan 262 and no weight is detected (S49: NO), or the scale timer is ended (S48: YES), the process to the medicine is ended. The process moves to the above S41 and stands by until the powdered medicine bottle 250 is again mounted.

Figure 45:
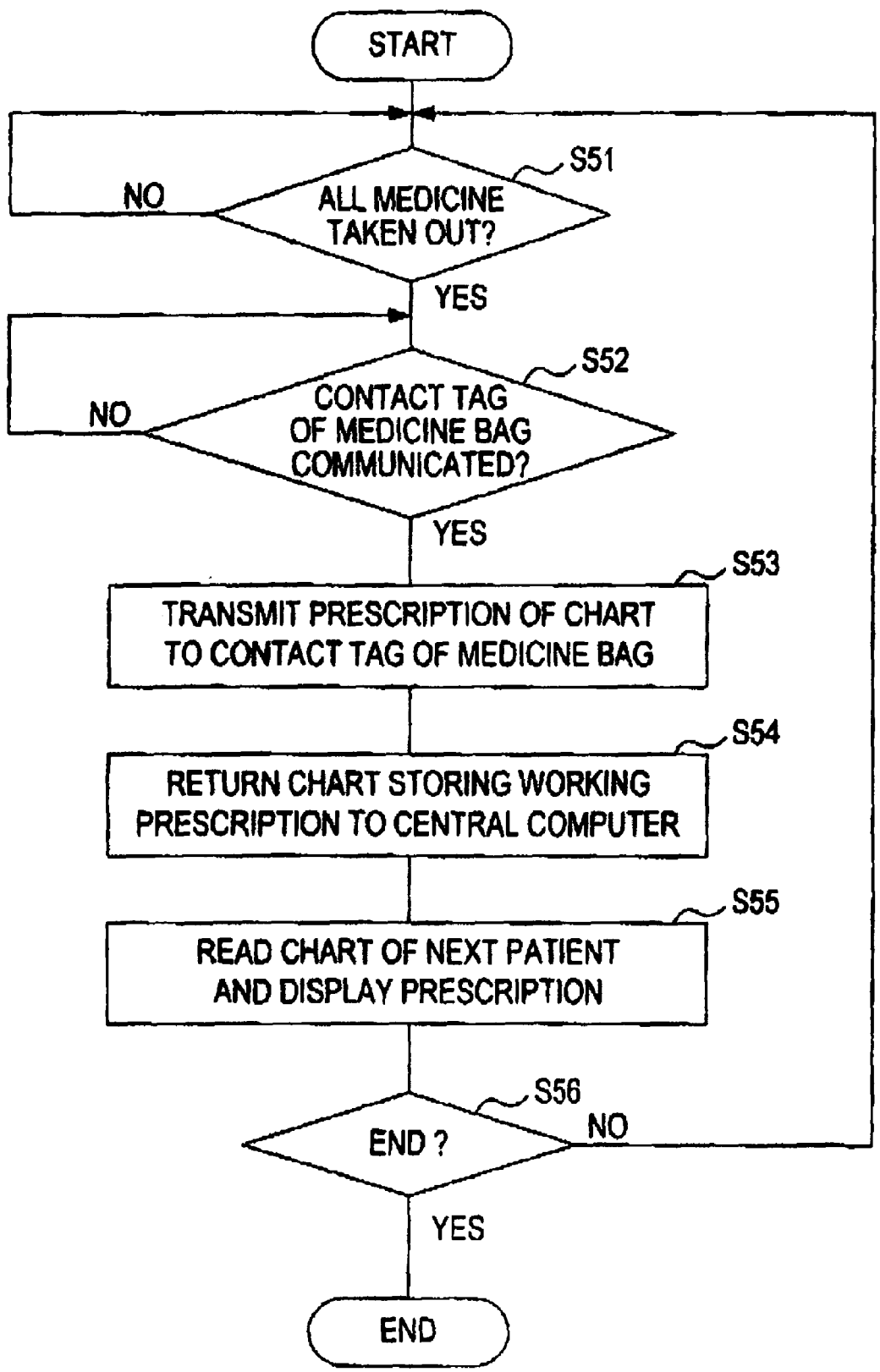
FIG. 45 is a flowchart showing a prescription end process executed by the aforementioned prescription computer.

Next, FIG. 45 is a flowchart showing a prescription end process for sequentially switching the prescription displayed on the display portion 222 by the prescription computer 220. When the process is started, the prescription computer 220 determines whether all the medicine in the prescription is taken out in S51, in the similar manner as in the above S35. If not all the medicine is not taken out (S51: NO), the process stands by. If all the medicine is taken out (S51: YES), the process moves to S52. In S52, the aforementioned contact path is created which passes the contact tag 1s of the medicine bag 270, and it is determined whether the contact tag 1s has performed contact communication.

That is, when prescription is completed, the pharmacist fills the medicine into the medicine bag 270. Thus, in S52, the process stands by until operation of filling the medicine into the medicine bag 270 is performed. When the medicine is filled into the medicine bag 270 and the contact tag 1s of the medicine bag 270 performs contact communication (S52: YES), the process moves to S53, and the prescription of the chart is transmitted to the contact tag 1s of the medicine bag 270. At this time, how to take the medicine, contraindication information, etc., described in the prescription are also transmitted to the contact tag 1s. In subsequent S54, the chart storing the prescription displayed on the display portion 222 till then is returned to a not shown central computer. In S55, a chart of the next patient is read and the prescription is displayed on the display portion 222.

In subsequent S56, it is determined whether the process is END, for example by shut down of the prescription computer 220. If not END (S56: NO), the process moves to S51 and the above steps are repeated. If END (S56: YES), the process is once ended.

In this manner, instructions are given so that there is no error (in kind and amount) in prescription of medicine. Even if an error may occur, checking is performed. Moreover, checking is performed when other than the pharmacist has made contact. Thus, theft or unauthorized use of medicine can be avoided.

Figure 46:
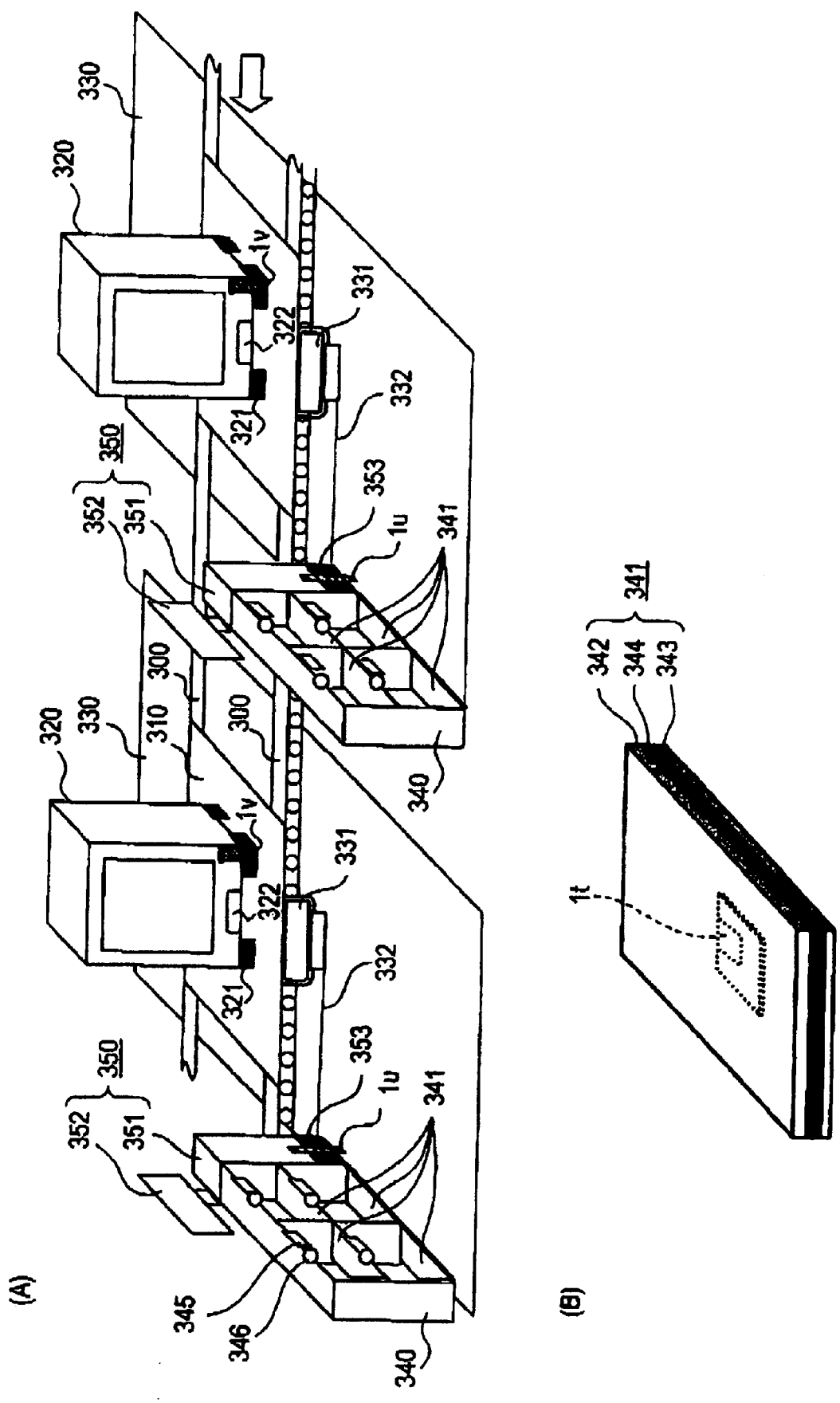
FIG. 46 is an explanatory view showing an application of the present invention to a factory, specifically in which (A) shows an overall configuration and (B) shows a rack board of a parts rack.

Next, FIG. 46 is an explanatory view showing an application of the present invention to a factory. As shown in FIG. 46(A), a belt conveyor 300 is disposed in the factory, and a refrigerator 320 in a manufacturing process is placed on a conveyor plate 310 arranged on the belt conveyor 300. The belt conveyor 300 is arranged so as to pass through a plurality of operation booths 330 zoned for respective process steps. An instruction computer 350 for instructing an operation and a parts rack 340 for storing tools and parts are disposed in one area of each operation booth 330. Also in this example, a floor of the each operation booth 330 is conductive, and an operator in the factory wears a contact communication device 20 which is the same as described above.

An entirety of the parts rack 340 is made of a conductive material, and an insulating material is applied to an undersurface of a bottom plate, and inner surfaces of both sides and a ceiling surface of each section. As shown in FIG. 46(B), a rack board 341 placed at a bottom of the each section has a sandwiched configuration, including an insulating plate 344, conductive plates 342, 343 sandwiching the insulating plate 344, and a contact tag 1t disposed so as to extend between and connect the conductive plates 342 and 343. An indicator 345 and a rack lamp 346 are provided in an upper portion of the each section of the parts rack 340.

An entirety of the instruction computer 350, including a display portion 352 and a main body 351, is made of a conductive material, and is provided to the operation booth through an insulating rack 353. A contact tag 1u is disposed so as to extend between the floor in the operation booth 330 and the main body 351. Accordingly, when the operator touches a tool or a part stored in the parts rack 340, a contact communication is performed through the contact tags 1t and 1u, in the same manner as in a case of the above described pharmacy. The contact tag 1u is also connected to a CPU in the instruction computer 350.

Figure 47:
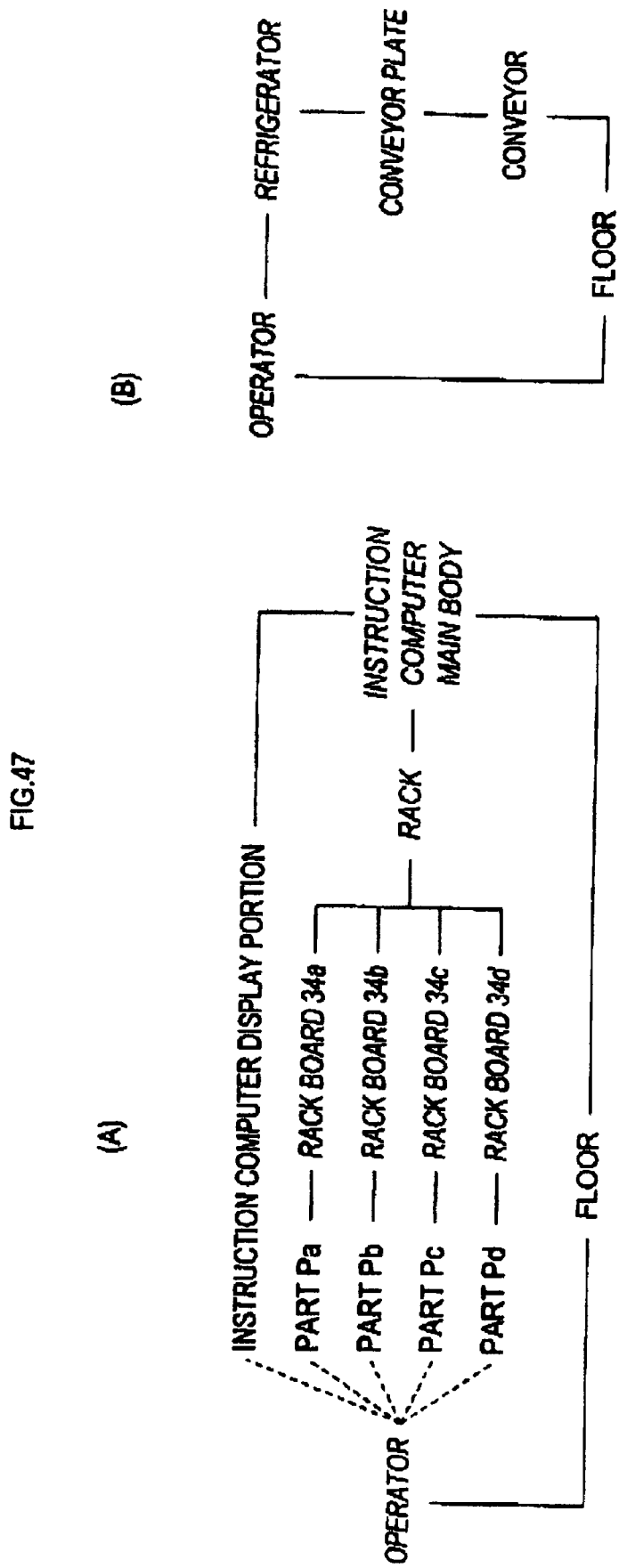
FIG. 47 is an explanatory view schematically showing a contact path in the application.

FIG. 47(A) schematically shows a contact path through which the contact communication is performed. In FIG. 47(A), parts stored in respective sections of the parts rack 340 are indicated by Pa, Pb, Pc, . . . , and same suffixes (hereinafter the same will apply) are assigned to respective rack boards 341 which constitute the respective sections.

All four legs 321 of the refrigerator 320 are made of an insulating material. A contact tag 1v is disposed over one of the legs 321 so as to extend between the conductive main body of the refrigerator 320 and the conductive conveyor plate 310. The conveyor plate 310 may be a simple iron plate, but may have a same configuration as the rack board 341, which includes an insulating material embedded with a contact tag 1 and conductive plates sandwiching the insulating material. In both cases, contact communication is performed through the contact tag 1v when the operator assembles a part to the refrigerator 320. In the latter case, the contact communication is performed also through the contact tag 1 embedded in the conveyor plate 310. A contact path of the contact communication is schematically shown in FIG. 47(B).

In addition, a wireless tag 322 is fixed to a front surface of the refrigerator 320, and a wireless tag receiver 331 communicating with the wireless tag 322 is provided in a position adjacent to the belt conveyor 300 in the operation booth 330. The wireless tag receiver 331 constantly detects the wireless tag 322 on the refrigerator 320 placed on the belt conveyor 300 in the operation booth 330. The wireless tag receiver 331 constantly transmits an ID of the refrigerator 320 detected from the wireless tag 322 respectively to the instruction computer 350 in the operation booth 330 through a communication bus 332 and to the contact communication device 20 of the operator wirelessly.

Next, a description will be provided about processings performed by the instruction computer 350 in the operation booth 330 configured as above. First, the instruction computer 350 is capable of storing a manufacturing chart and a rack parts list in the memory thereof.

In the manufacturing chart, a specification and a manufacturing procedure, such as an order of assembly of parts, for each product to be manufactured are stored. While detailed instructions on the order of parts to be assembled are stored, columns for storing detailed data when an actual manufacturing is performed are provided. For example, a manufacturing chart is prepared for each refrigerator 320 to be manufactured, and various procedural steps, such as parts to be assembled, painting, and inspection items are stored. Columns (a retrieval time column and an assembly time column) are provided for each part to be assembled so as to store an operator ID, and a time of retrieval of the part from the parts rack 340 and a time of assembly of the part by the operator, and storage into appropriate columns is always available.

The instruction computer 350, which has received an ID of a refrigerator 320 received through the wireless tag receiver 311, receives a manufacturing chart corresponding to the refrigerator 320 from a central computer through a not-shown LAN. When an operation on the refrigerator 320 in the operation booth 330 is completed, the instruction computer 350 sends back the manufacturing chart to the central computer.

The rack parts list is a list of parts stored in the respective sections of the parts rack 340 and the respective rack boards 341 in the operation booth 300. In the list, the rack boards 341 and the parts on the respective rack boards 341 are stored in a corresponding manner. Accordingly, when the operator touches one of the parts, and thereby a contact communication is performed through the contact tag 1t embedded in the rack board 341 under the part, the part can be identified by referring to the rack parts list.

The instruction computer 350 and the contact communication device 20 of the operator in the same operation booth 330 constantly wirelessly intercommunicate stored information, such as detected information and the manufacturing chart, thereby to update the information.

Figure 48:
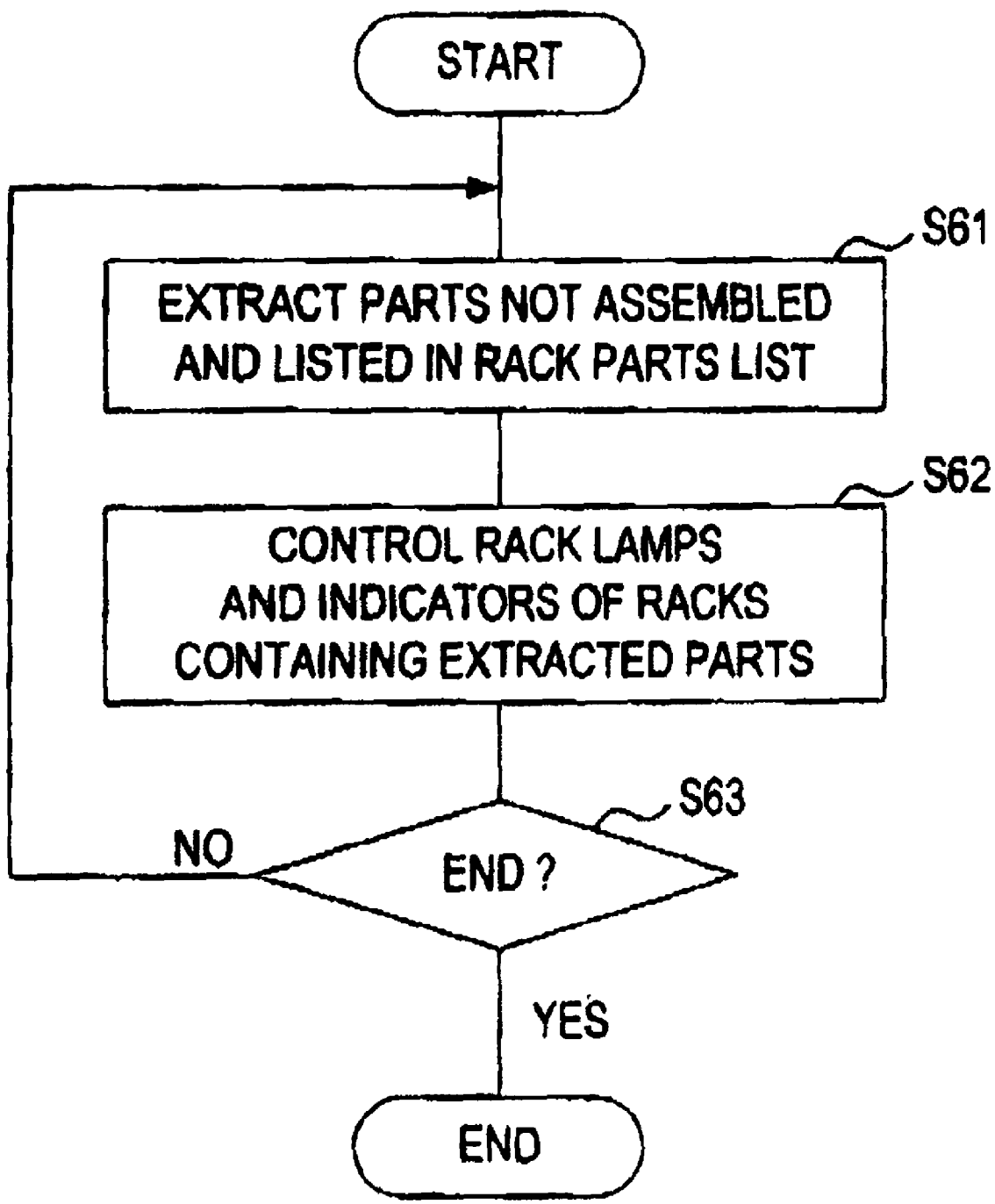
FIG. 48 is a flowchart showing an indication control process executed by an instruction computer in the application.

Next, FIG. 48 is a flowchart showing an indication control process executed by the instruction computer 360 to control the indicators 345 and the rack lamps 346. When the process is started, the instruction computer 350 first extracts, in S61, parts which have not yet been assembled and are listed in the rack parts list of the operation booth 330 from the parts included in the manufacturing chart received as described above. Whether or not a part has been assembled is stored in the manufacturing chart in accordance with a later-described process.

Subsequently, in S62, rack lamps 346 and indicators 345 of sections, where the parts extracted in S61 are stored, are controlled as below. Specifically, in this step, a rack lamp 346 of a section, where a part assigned an earliest order of assembly is stored, is lit in blue, while, a rack lamp 346 of a section, where a part assigned a second earliest order of assembly is stored, is lit in yellow. In a case of unspecified order of assembly, all rack lamps 346 of the sections, where the parts extracted in S61 are stored, are lit in blue. When it is necessary to assemble a plurality of same parts, a number of the same parts is indicated by the indicator 345.

Subsequently, in S63, it is determined whether or not the instruction computer 350 has been ended by a shutdown or the like. When it is determined as not ended (S63: NO), the present process proceeds to S61 and the above processings are repeated. When it is determined as ended (S63: YES), the present process is terminated here.

Figure 49:
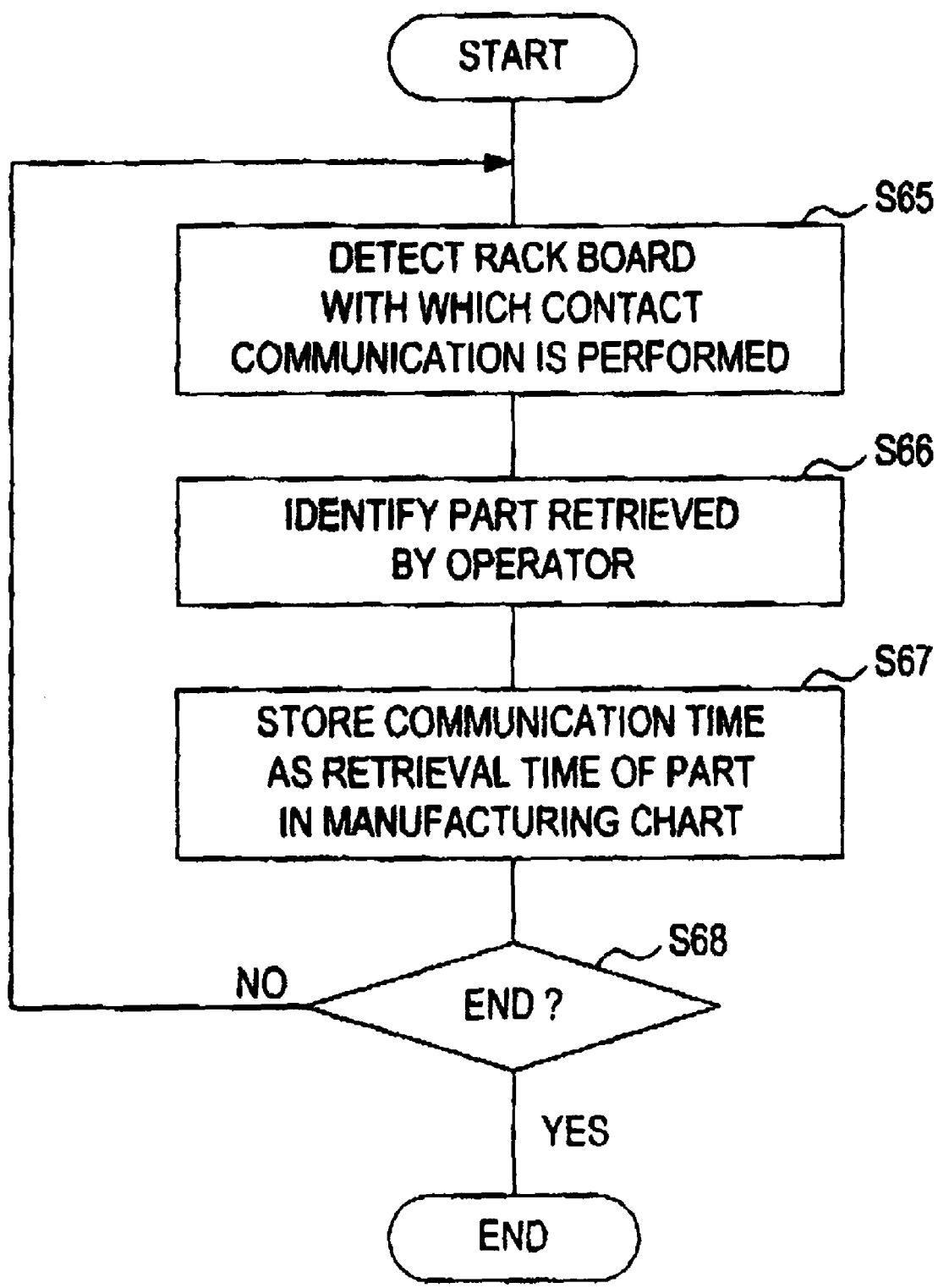
FIG. 49 is a flowchart showing a retrieval detection process executed by the instruction computer.

FIG. 49 is a flowchart showing a retrieval detection process for detecting a state of retrieval of a part by the operator, which is executed by the instruction computer 350 and the contact communication device 20 of the operator. When this process is started, the operator retrieves a part or the like and a contact path is formed among the rack board 341 on which the part is stored, the contact communication device 20 of the operator, and the instruction computer 350, and thereby a contact communication is performed through the contact tag 1t of the rack board 341, the contact communication device 20 of the operator, and the contact tag 1u of the instruction computer 350. Thus, an ID of the rack board 341 is detected (S65). Subsequently, in S66, the rack board 341 is referred to the rack parts list, and thereby the part retrieved by the operator is identified.

Further subsequently in S67, a communication time when the above contact communication is performed is regarded as a time when the operator retrieves the part from the parts rack 340 and is stored in a retrieval time column of the above identified part in the manufacturing chart. Also, an ID of the operator is stored in a retriever column of the part in the manufacturing chart. Subsequently in S68, it is determined whether or not the instruction computer 350 or the contact communication device 20 of the operator has been ended by a shutdown or the like. When it is determined as not ended (S68: NO), the present process proceeds to S65 and the above processings are repeated. When it is determined as ended (S68: YES), the present process is terminated here.

Figure 50:
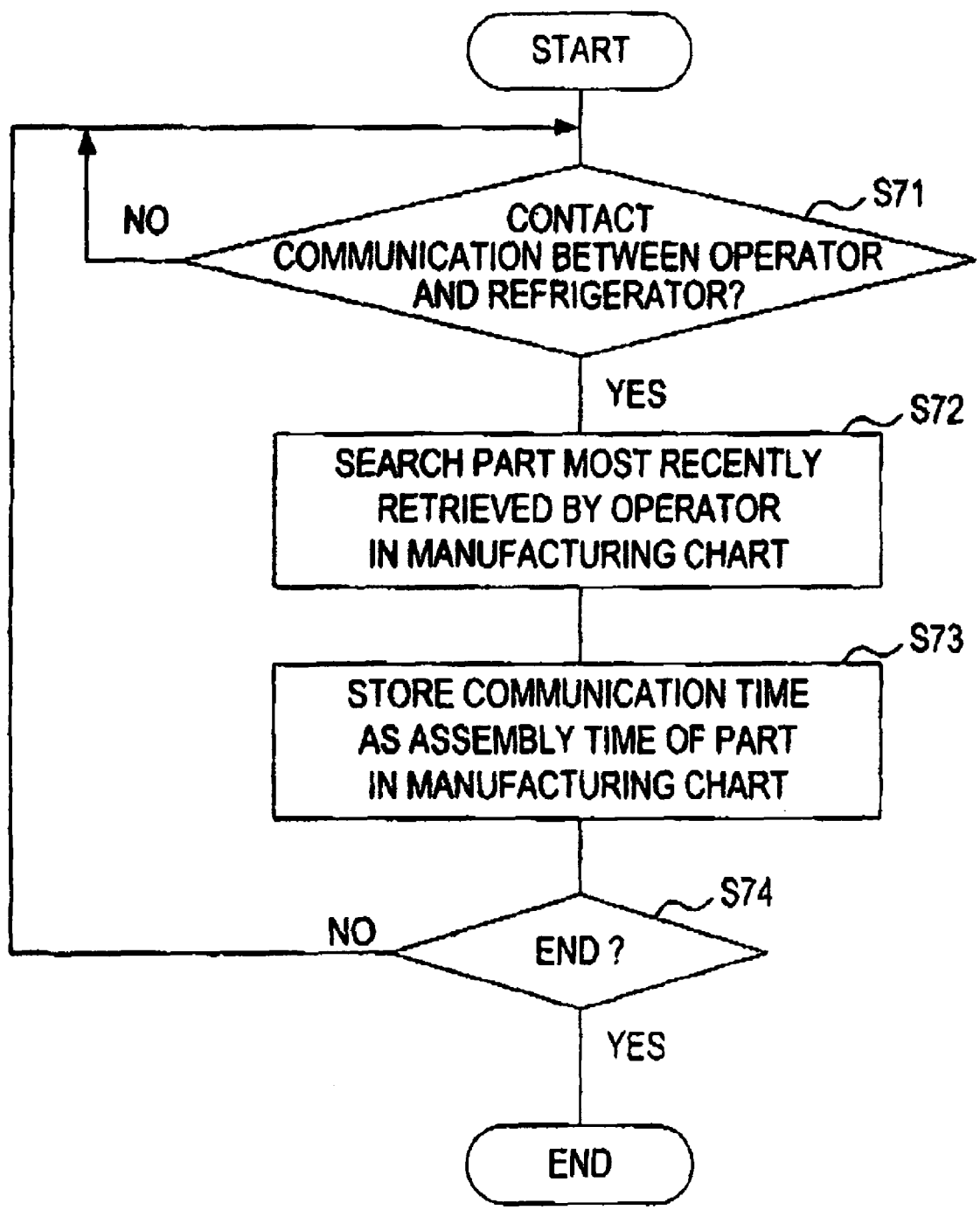
FIG. 50 is a flowchart showing an assembly detection process executed by the instruction computer.

FIG. 50 is a flowchart showing an assembly detection process for detecting a state of assembly of a part by the operator. When this process is started, the instruction computer 350 first waits, in S71, for contact communication to be performed between the contact communication device 20 of the operator and the contact tag 1v of the refrigerator 320. When it is determined that contact communication is performed between the contact communication device 20 of the operator and the contact tag 1v of the refrigerator 320 (S71: YES), it is regarded that a part most recently retrieved by the operator from the parts rack 340 is assembled to the refrigerator 320, and the following processing is performed. Specifically, a part with a most recent time in the retrieval time column stored by the above-described retrieval detection process is extracted from the manufacturing chart, and the part is identified (S72).

Subsequently in S73, a communication time when the contact communication is performed between the contact communication device 20 of the operator and the contact tag 1v of the refrigerator 320 is regarded as a time of assembly of the part to the refrigerator 320 by the operator, and the time is stored in an assembly time column of the above identified part in the manufacturing chart. Also, the ID of the operator is stored in an assembler column of the part in the manufacturing chart. Subsequently in S74, it is determined whether or not the instruction computer 360 or the contact communication device 20 of the operator has been ended by a shutdown or the like. When it is determined as not ended (S74: NO), the present process proceeds to S71 and the above processings are repeated. When it is determined as ended (S74: YES), the present process is terminated here.

A parts search in S72 may be performed by searching a part with a filled retrieval time column and an empty assembly time column, or may be performed by storing data of a part at the time of most recent contact communication with the parts rack 340 instead of referring to the manufacturing chart. While a part, regarding which the rack lamp 346 and the like should be controlled, is extracted in the above S36 based on whether or not the part has been assembled (see S 73), the part may be extracted based on whether or not the retrieval time column for storing the retrieval time in the manufacturing chart in S67 is filled.

Figure 51:
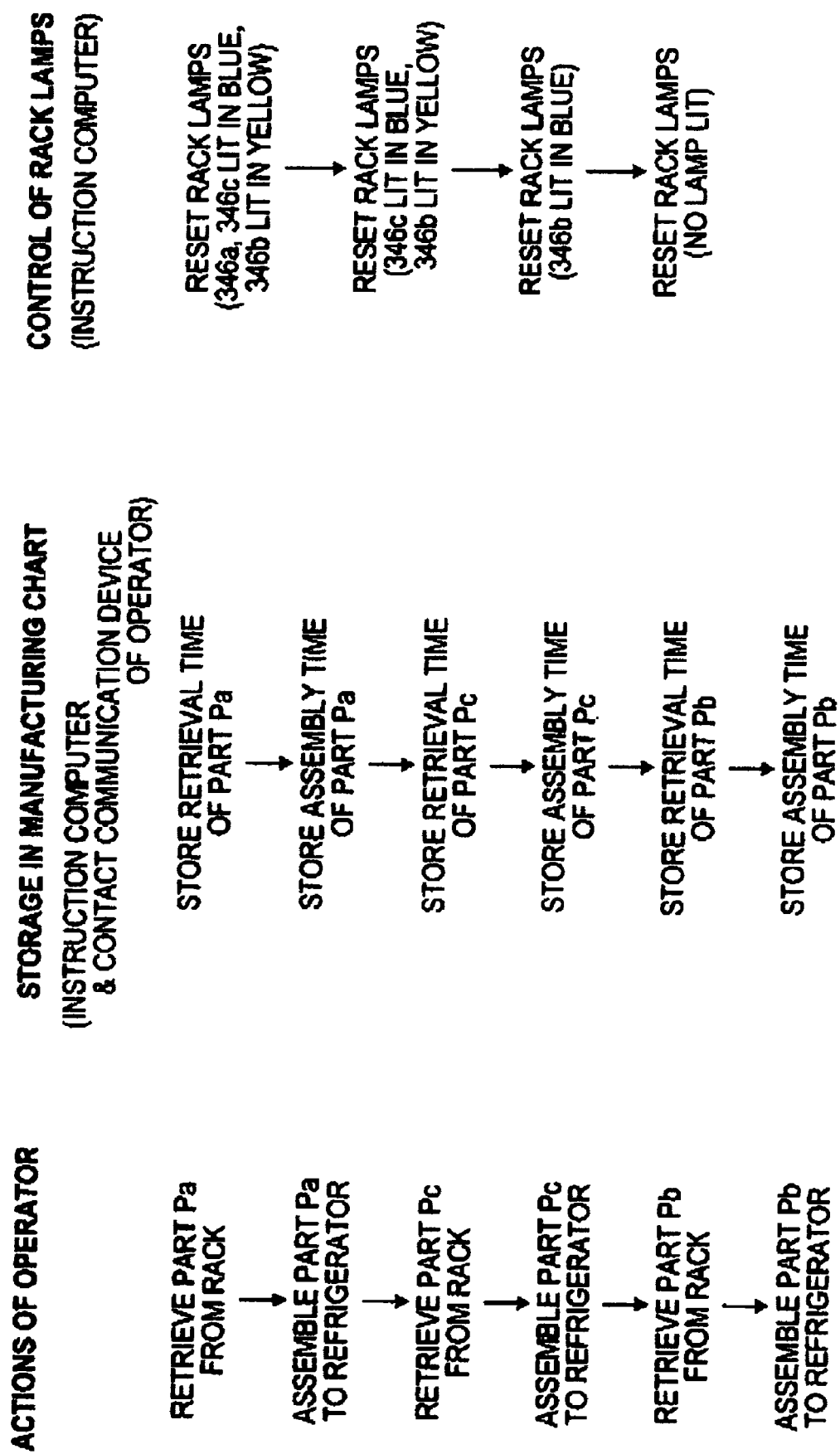
FIG. 51 is an explanatory view showing an example of changes in a manufacturing chart and rack lamps in accordance with actions of an operator.

According to the processings in FIG. 48 through FIG. 50, when it is required, for example, to retrieve the parts Pa, Pc, Pb sequentially from the parts rack 340 and assemble the same to the refrigerator 320, storage in the manufacturing chart and a control state of the rack lamp 346 are changed as shown in FIG. 51 in accordance with the operator's actions.

In a factory where the above described system is employed, when the refrigerator 320 is conveyed to the operation booth 330 by the belt conveyor 300, the wireless tag receiver 331 detects the wireless tag 322 on the refrigerator 320, and the instruction computer 350 and the contact communication device 20 of the operator receive the manufacturing chart of the refrigerator 320. Subsequently, retrieval of parts from the parts rack 340 and assembly of the parts to the refrigerator 320 by the operator are detected according to the above described processings in FIG. 48 through FIG. 50, and the indicators 345 and the rack lamps 346 are controlled in accordance with the detection. When assembly of all parts is completed, all the rack lamps 346 are turned off, and the manufacturing chart is sent back to a central computer by the instruction computer 350 and the contact communication device 20 of the operator.

However, if the refrigerator 320 is likely to be conveyed to another operation booth 330 during operation or if the operator leaves the operation booth 330 during operation, the belt conveyor 300 is required to be stopped. Accordingly, the instruction computer 350 sets a conveyor stop flag FG to 1 or resets to 0 according to the following conveyor stop process. The central computer observes a state of the conveyor stop flag in the instruction computer 350 of each of the operation booths 330, and stops the belt conveyor 300 when a conveyor stop flag FG is set in any one of the operation booths 330.

Figure 52:
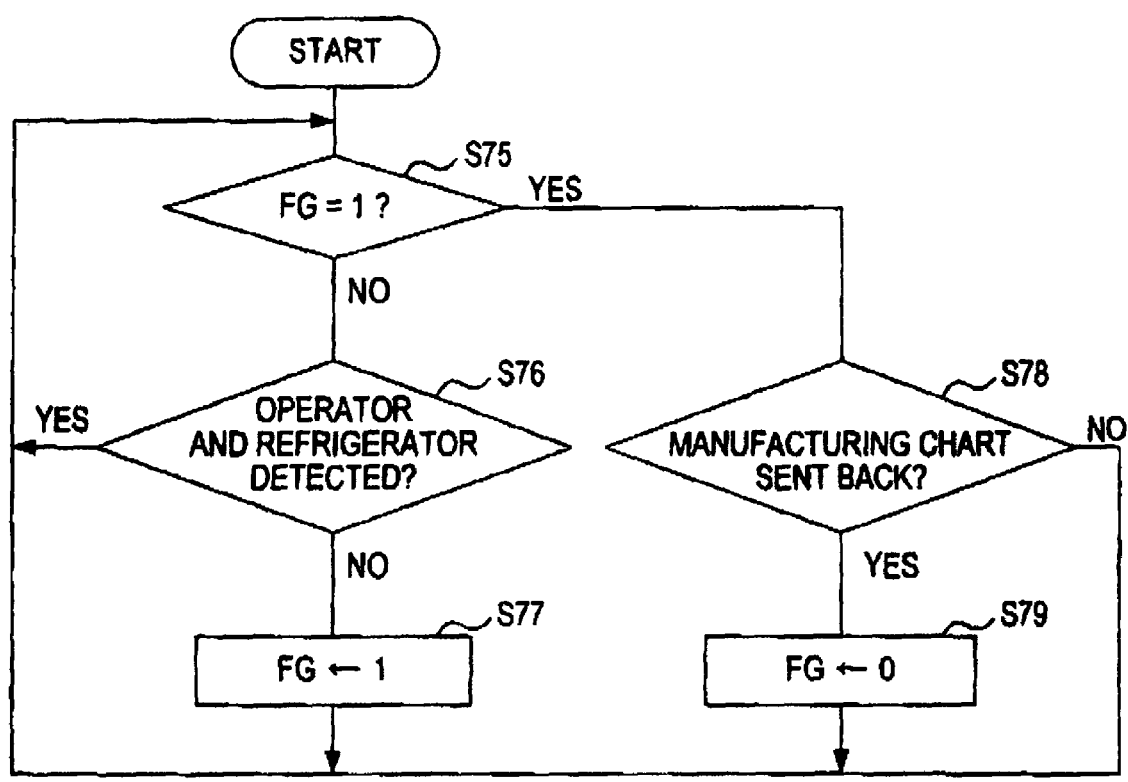
FIG. 52 is a flowchart showing a conveyor stop process executed by the instruction computer.

FIG. 52 is a flowchart showing a conveyor stop process executed by the instruction computer 350. When this process is started, the instruction computer 350 determines whether or not the conveyor stop flag FG is set (S75). When it is determined as not set (S75: NO), it is determined whether or not the operator and the refrigerator 320 are detected in the operation booth 330 based on a communication state with the contact communication device 20 and a receiving state of the wireless tag receiver 331.

When both of the operator and the refrigerator 320 are detected (S76: YES), the present process proceeds to the above S75, and the processings in S75 and S76 are repeatedly performed. When one of the operator and the refrigerator 320 is not detected (S76: NO), the conveyor stop flag FG is set in S77, and then the present process proceeds to the above S75.

After the conveyor stop flag FG is set (S75: YES), the present process proceeds from S75 to S78, and it is determined whether or not the instruction computer 350 has detected assembly of all the parts according to the above described processings and has sent back the manufacturing chart to the central computer. When it is determined that the manufacturing chart has not been sent back (S78: NO), the present process proceeds to S75. On the other hand, when it is determined that the manufacturing chart has been sent back (S78: YES), the conveyor stop flag FG is reset in S79, and then the present process proceeds to the above S75.

Specifically, once the conveyor stop flag FG is set (in S77), the processings in S75 and S78 are repeatedly performed waiting until the instruction computer 350 detects that all the parts have been assembled. When the assembly has been completed and the manufacturing chart has been sent back (S78: YES), the conveyor stop flag FG is reset (S79). According to the present process, it may be possible to stop the belt conveyor 300 until all the parts have been assembled and automatically restart the belt conveyor 300 after the completion of the assembly.

While the conveyor continuously advances at a constant speed in an ordinary state, it may also be possible to temporarily stop the conveyor until completion of assembly of the parts when it is detected that the refrigerator 320 is likely to move out of the operation booth before completion of assembly of the parts.

Further in this example, in the same manner as in the detection of medical errors, it may be possible to give an alarm by a buzzer or the like when the operator mistakenly retrieves a part to be assembled to the refrigerator 320 or mistakes the assembly order of a part. In addition, it may be possible to store such information in a storage column in the manufacturing chart, and review the information afterwards.

Furthermore, the present invention may be applied not only to prevent occurrence of an operation error, but also to detect various operational states and effectively utilize detection results. For example, FIG. 53 through FIG. 58 are explanatory views showing an application to a supermarket.

Figure 53:
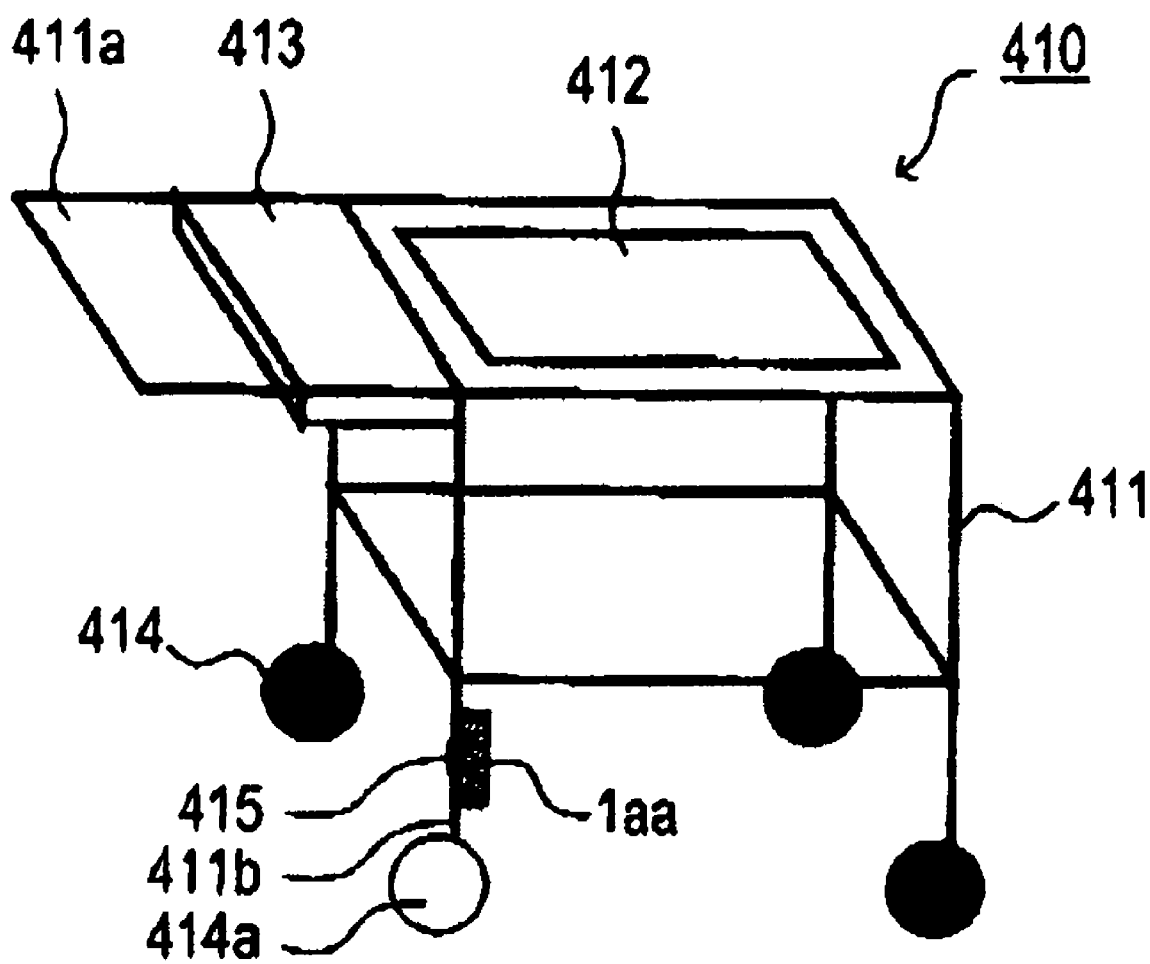
FIG. 53 is an explanatory view showing a configuration of a shopping cart in an application of the present invention to a supermarket.

FIG. 53 shows a configuration of a shopping cart 410. As shown in FIG. 53, a framework 411, including a handle 411a, of the shopping cart 410 is made of a conductive material, and a frame 412 for receiving a shopping basket (not shown) functions as an antenna for receiving radio wave from a later-described wireless tag 422 and the like. A receiver main body 413 for receiving the radio wave through the frame 412 is provided at a base of the handle 411a.

Three of four wheels 414 of the shopping cart 410 are made of an insulating material, and only one wheel 414a is made of a conductive material. A support portion 411b of the wheel 414a in the framework 411 is insulated from the remaining part of the framework 411 through an insulating portion 415, and a contact tag 1aa is disposed so as to extend over the insulating portion 415. Accordingly, when a shopper walks in the supermarket grabbing the handle 411a, a contact path is formed through a shopper's body→the handle 411a→the framework 411→the contact tag 1aa→the support portion 411b→the wheel 414a→a floor→the shopper's body.

Figure 54:
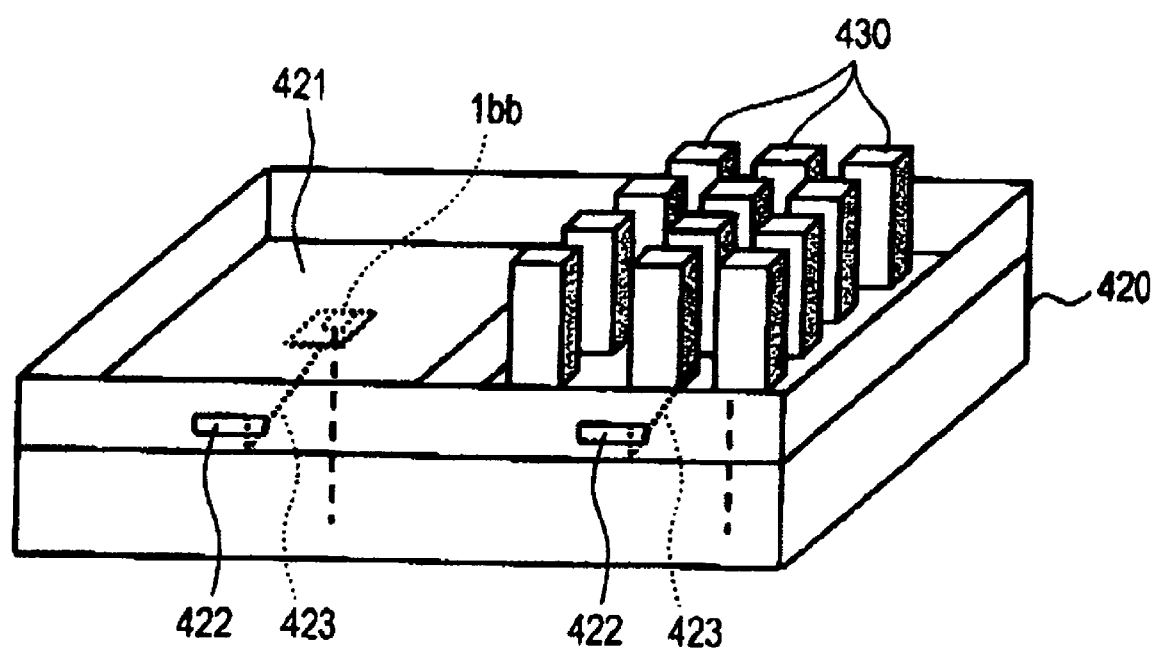
FIG. 54 is an explanatory view showing a configuration of a showcase in the application.

FIG. 54 is an explanatory view showing a configuration of a showcase 420 in the supermarket. As shown in FIG. 54, products such as milk 430 packed with a surface made of a conductive material are displayed in the showcase 420. The showcase 420 is configured in substantially a same manner as in the above described parts rack 340. Specifically, a bottom board 421 includes an insulating material, two conductive plates sandwiching the insulating material, and a contact tag 1$bb$ disposed so as to extend between and connect the two conductive plates. Accordingly, when the shopper touches the milk 430, a contact path is formed and contact communication is performed by the contact tag 1$bb$.

A wireless tag 422 provided in front of the showcase 420 is connected to the contact tag 1$bb$ through a signal line 423. Accordingly, when the contact communication is performed by the contact tag 1$bb$, data such as a product's price may be transmitted from the wireless tag 422 to the shopping cart 410. Since milk of a same type 430 is displayed in one section, it is possible to identify the type and the price of milk 430 based on an ID of the contact tag 1$bb$.

Figure 55:
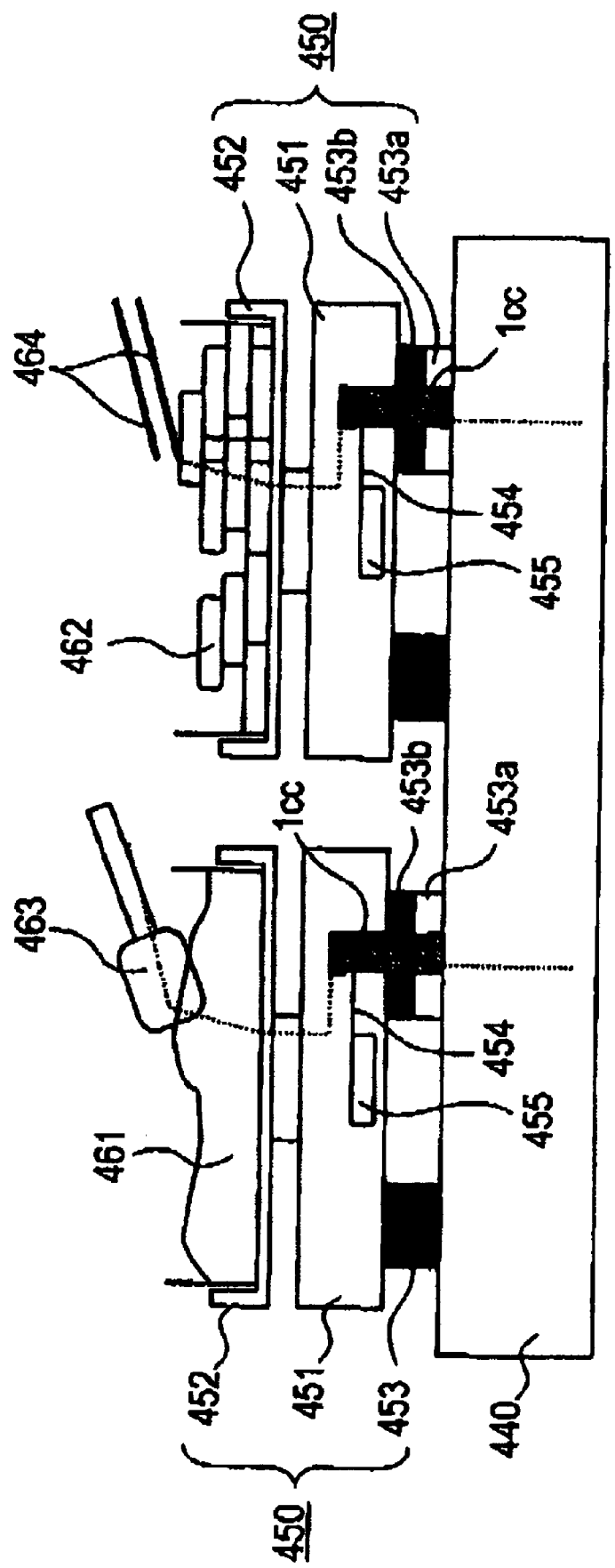
FIG. 55 is an explanatory view showing a configuration for selling by weight in the application.

FIG. 55 is an explanatory view showing a configuration for selling products such as prepared foods by weight. Scales 450 having a same configuration as the above described scale 260 are mounted on a conductive base 440. Each of the scales 450 includes a main body 451, a scale pan 462 above the main body 451, and four legs 463 supporting the main body 451. Three of the four legs 453 are made of an insulating material, while one leg 453$a$ is made of a conductive material except for a proximal end portion 453$b$ thereof. A contact tag 1$cc$ is disposed so as to extend over the proximal end portion 463$b$. In addition, a wireless tag 455 connected to the contact tag 1$cc$ through a signal line 454 is provided in front of the main body 451.

Accordingly, when the shopper scoops cooked rice 461 contained in the scale pan 462 with a conductive rice paddle 463, or picks up a piece of Hamburg steak 462 contained in the scale pan 452 with conductive chopsticks 464, a contact path is formed through the contact tag 1$cc$, and data, including a price of the product depending on a weight reduction, is transmitted from the wireless tag 455. In this case, the data may be transmitted after oscillation of the scale pan 452 is stabilized. A price of the cooked rice 461 or the like is calculated based on a weight reduction by gram unit, while a price of the Hamburg steak 462 or the like is calculated based on a value obtained by converting a weight reduction into a number of pieces. It is required to transmit the number of pieces of the Hamburg steak 462 to a contact communication device 20 of the shopper when the Hamburg steak 462 is picked out and weight measurement is enabled. However, after the Hamburg steak 462 is picked out, no contact path is formed and thus contact communication cannot be performed. Therefore, wireless tags are provided to the scale 450 and the contact communication device 20 of the shopper so that the number of pieces of the Hamburg steak 462 can be transmitted to the contact communication device of the shopper by performing wireless communication. As described above, a contact tag has a disadvantage that communication cannot be performed with an object that does not contact the contact tag although detection of only an object that contacts the contact tag can be performed accurately. Accordingly, a wireless tag is used as well. Specifically, an object that contacts the contact tag is accurately identified and communication to the identified object is performed wirelessly, so that transmission to a shopper who purchases a product is accurately performed. In other words, a wireless tag has a disadvantage that an object that contacts the wireless tag cannot be identified, and therefore the object should be identified by using a contact tag.

A detailed description will be provided taking an example in which a shopper scoops out a desired amount of cooked rice from a bowl placed on a scale. To accurately weighing cooked rice without a wireless system, the shopper is required to wait in front of the scale until the scale is stabilized after scooping out the cooked rice and to contact the scale again so that a weighed value can be received by a contact communication device of the shopper. Accordingly, not only is it necessary to wait in front of the scale until the scale is stabilized, but also there is a possibility of occurrence of a weight measurement error due to a contact with the scale for reception of the value. With a wireless system, however, when the shopper scoops out cooked rice from the bowl, the shopper is identified by the contact communication device, and thus the identified shopper can leave the scale and receive a weighed value wirelessly by the contact communication device when the scale is stabilized after scooping out the cooked rice. Accordingly, it may be possible to save a waiting time for weight measurement and prevent occurrence of a measurement error.

As described above, the contact communication device has a feature that identification of a shopper who contacts the contact communication device is capable, but communication with a remote place is incapable. In contrast, wireless communication has a feature that differentiation between the shopper and an adjacent shopper is incapable, but communication with a remote shopper is capable. The scale has characteristics that it requires time for accurate weight measurement and dislikes oscillation. That is, while a contact is required for identification of a shopper, the contact is undesirable for measurement. In wireless communication, while communication with a remote shopper is capable, identification of a shopper is incapable. Contact communication has an advantage that identification of a shopper is capable and a disadvantage that communication with a remote shopper is incapable. However, by combining a scale, wireless communication and contact communication, different disadvantages of the three elements are appropriately mutually compensated for, and only the above described advantages of the three elements can be brought out.

FIG. 56 shows a configuration for selling clothes. As shown in FIG. 56(A), substantially an entirety of each of clothes 500, a hanger 610 for hanging the clothes 500, and a hanger rack 520 for hanging a hanger 510 is made of a conductive material. However, an insulating portion 512 is provided to a proximal portion of a neck 511 of the hanger 510, and insulating portions 522, 522 are provided to the vicinities of bases of respective feet 521, 521 of the hanger rack 520. A contact tag 1$dd$ is provided so as to extend over the insulating portion 612 of the hanger 510, and a contact tag 1$ee$ is provided so as to extend over one of the insulating portions 522, 522 of the hanger rack 520.

Accordingly, when a shopper picks up the clothes 500, a contact path through the contact tags 1$dd$, 1$ee$ is formed, and a contact communication device 20 of a shopper performs contact communication with the contact tags 1$dd$, 1$ee$. Also, a wireless tag 530 is attached to the clothes 500 through a thread 540. Since same data, including a price, about an item is stored both in the wireless tag 530 and in the contact tag 1$dd$, receiving data stored in one of the tags is enough. However, a wireless tag has a disadvantage that data in a wireless tag 630 of a non-picked up item may also be received, or data in a wireless tag 530 of a picked up item may not be received. A contact tag has a disadvantage that communication is capable only while the contact tag is contacted. Accordingly, it is configured to identify an item and a shopper who has picked up the item, and also securely and accurately determine the picked up item by using a wireless tag and a contact tag. Even when contact communication becomes incapable, information of the picked up item can be transmitted via wireless communication to the shopper identified by the contact communication.

In a case of attaching a wireless tag having a flat configuration to the clothes 500, an antenna surface of the wireless tag is positioned in parallel with the clothes 500. Then, the wireless tag can detect only data from a direction perpendicular to a flat surface of the clothes 500 (for example, in a direction of arrow A in FIG. 56(A)). In this case, it is impossible to insert a wireless tag receiver into a place where reception is capable if the hanger rack 520 is located at a corner of a shop or a lot of clothes 500 are hung thereon. As a result, detection of data of the clothes 500 is likely to be incapable.

Accordingly, in the present embodiment as shown in FIG. 56(B), the wireless tag 530 is constituted by three flat surfaces (a first surface 531, a second surface 532, a third surface 533) perpendicular to one another. A chip and an antenna are provided to each of the surfaces. Accordingly, detection of data is capable even from a direction along the surface of the clothes 600 (for example, from a direction of arrow B in FIG. 56(A)). Since the chip and the antenna are provided to the third surface 533 which is usually arranged horizontally, detection of data is capable even when the wireless tag 530 is turned. However, the chip and the antenna on the third surface 533 may be omitted since the possibility of such a turn of the wireless tag 530 is low.

In the example shown in FIG. 56(B), the third surface 533 is provided in respective central portions of the first surface 531 and the second surface 532 arranged so as to have a common side and be perpendicular to each other. By providing the third surface 533 in respective central portions of the first surface 531 and the second surface 532, the first surface 531 and the second surface 532 may easily remain in a perpendicular position. Alternatively, as shown in FIG. 56(C), the third surface 533 may be provided at one end of each of the first surface 531 and the second surface 532 so as to constitute a corner of a rectangular parallelepiped box by the first surface 531, the second surface 532 and the third surface 533. In this case, it may be possible to effectively avoid the third surface 533 from intervening communication by the first surface 531 and the second surface 532. In a case of using the wireless tag 530 constituted by three surfaces, the three surfaces may be assigned respective IDs, for example, 123456a, 123456b and 123456c, so that processing using the IDs may be facilitated.

A further detailed description of a configuration of the first surface 531 will be provided with reference to FIG. 57(A). It is to be noted that each of the second surface 532 and the third surface 633 is configured in a same manner. As shown in FIG. 57(A), the first surface 633 includes planar tag portions 631*a*, 531*b*, each having a chip 551 and an antenna 552, and a radio wave blocking layer 531*c* disposed between the tag portions 531*a* and 531*b*. This configuration in the present embodiment serves to prevent a detection error as described below.

Specifically, while a wireless tag facilitates easy detection due to wirelessness, a detection error, such as a detection failure or a detection of unintended target may be caused. Accordingly, it may be possible to determine whether or not a detection error is caused based on a direction of detection.

A typical wireless tag is constituted only by the above described tag portion 531*a* or 531*b*, and data or the like can be received from each of a front side and a reverse side of a surface facing an antenna 552. In contrast, when the radio wave blocking layer 531*c* for blocking radio transmission is applied to the reverse side of the surface, data cannot be received from the reverse side while a sensitivity on the front side may be improved. When the radio wave blocking layer 531*c* is disposed and attached between the two tag portions 531*a* and 531*b*, as shown in FIG. 57(A), favorable communication may be performed on both the front and reverse sides. Furthermore, since the first surface 631, the second surface 532 and the third surface 533 are configured to be perpendicular to one another in the present embodiment, a radio wave from the wireless tag 530 may be received from any direction, and it may be possible to determine whether or not a detected radio wave is due to a detection error based on a direction of the detected radio wave.

The wireless tag 530 exemplarily shown in FIG. 56(C) may be manufactured by previously forming a mounting board 560, including the first surface 561, the second surface 562 and the third surface 563 perpendicular to one another, and by applying wireless tags to the surfaces. Further, it may be possible to form the mounting board 560 by using a radio wave blocking material capable of blocking radio waves, and apply wireless tags to both front and reverse sides of the respective three surfaces. This enables reception of a radio wave from any direction, and also serves to determine whether the radio wave is detected by a detection error or detected appropriately. Also, an orientation of an item may be detected.

Further, an item has a desirable surface to be shown. For example, in a case of orange juice 600 shown in FIGS. 57(C), (D), it is desirable that a surface with a picture of delicious-looking oranges is oriented in a front direction. Accordingly, in this case, an attachable wireless tag 601 may be attached as shown in FIG. 57(C), or a three-dimensional wireless tag 602 may be applied as shown in FIG. 57(D). The attachable wireless tag 601 is configured in a same manner as the wireless tag shown in FIG. 57(A), including the radio wave blocking layer 531*c* and the tag portion 531*a* sequentially layered, while the three-dimensional wireless tag 602 is configured in a same manner as the wireless tag 530 shown in FIG. 56(C).

Figure 58:
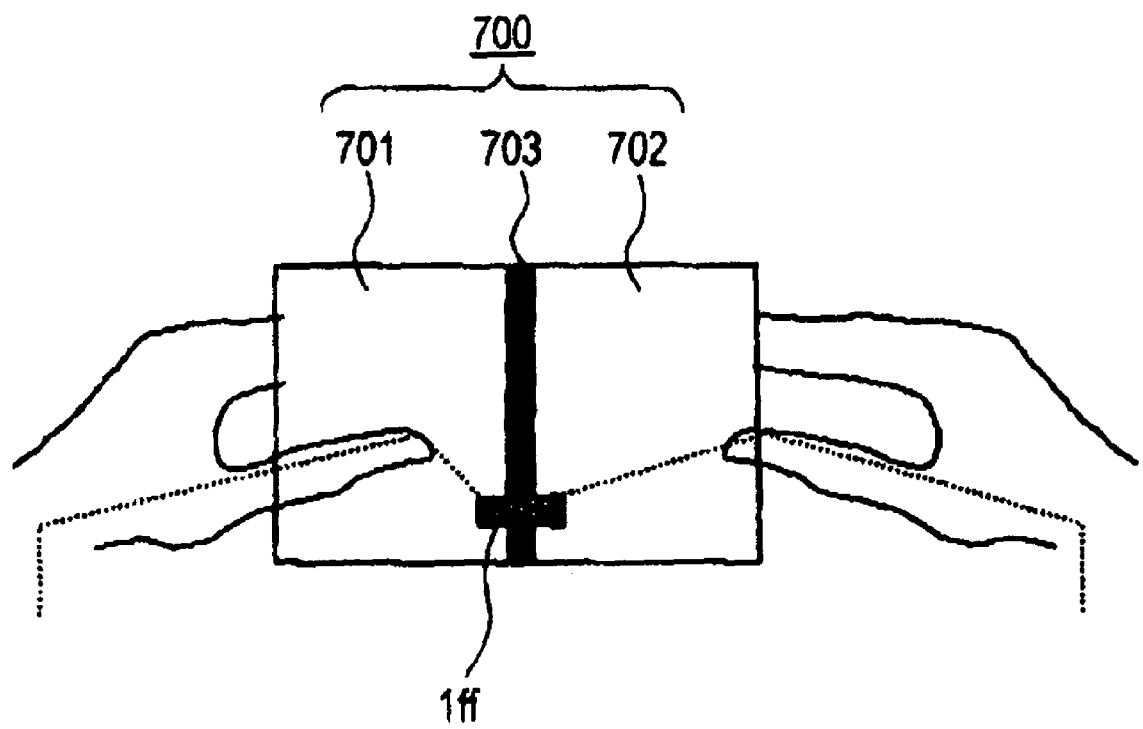
FIG. 58 is an explanatory view showing a configuration of a gift certificate in the application.

Furthermore, the present invention may also be applied to a gift certificate and the like. For example, as shown in FIG. 58, a gift certificate 700 may include one end portion 701 and the other end portion 702 made of a conductive material, an insulating portion 703 provided therebetween, and a contact tag 1*ff* extending over the insulating portion 703. In this case, when a shop clerk carrying a contact communication device 20 picks up both end portions 701, 702 of the gift certificate 700, a contact path passing through the contact tag 1*ff* is formed, and thus processing of the gift certificate 700 at a register may be executed automatically.

Also, the contact communication device 20 may include a device that provides voice notification of a face value and the like when the contact path is formed. This will help a blind person know the face value of the gift certificate 700. Such a configuration may be applied to various types of tickets, admission tickets, or even paper notes issued by a government, other than gift certificates. Further, when the contact communication device 20 having a voice generating function as above is configured into a ring-shape and a coin in a game arcade or a coin issued by a government is configured in a same manner as the above described rack board 341, it may be possible to cause the contact communication device 20 to generate a voice notification of the face value and the like by picking up the coin or the like with a finger (other than a thumb) carrying the contact communication device 20 and the thumb.

Next, application examples of the contact communication to automobiles are described.

Firstly, an example of bump detection against a pedestrian and the like is described with reference to FIGS. 59-60.

Today, an airbag for a driver's seat is operated upon detection of shock G when a bump takes place. However, since it is necessary to inhibit an improper operation, caused other than when a bump takes place, an airbag should not be operated simply by detection of shock G. Bumps are detected by using various sensors and complicated algorithms. Therefore, certain amount of time is required until a driver's seat airbag is operated since a bump takes place and shock is detected. For example, since various shock waves are generated depending not only on speed, but also on the hardness of an object bumped against, analysis time is required in order to detect these waves and analyze the waves. As described above, operation of airbags needs to be performing according to various conditions of a bump, such as speed (high-speed, mid-speed, low-speed), the hardness of an object bumped against, a bumped portion (a front surface, a lateral surface, a rear portion, offset bump), and so on. However, even if various sensors are installed for this purpose, time is required for processing bump estimating algorithms, and an airbag might not be operated in time. Moreover, there are problems such that a G sensor does not receive shock waves while shock is absorbed by a soft bumper, or that a G sensor receives different shock waves depending on a portion or a member of a car where the G sensor is installed.

In a case wherein a contact tag is used as a bump detection sensor, time required for shock wave transmission is not necessary, and restriction for an installation position of the sensor is limited. Moreover, in FIG. 59, an example is shown wherein contact is detected in the left portion of the front bumper. Contact tags may be also installed in every spot for detecting bump so that a bumped portion of a car can be easily specified. For example, a contact tag may be installed in the right portion of the front bumper so as to detect a bump in the right portion of the front bumper. If another party in a bump is equipped with a contact tag, whether the party is an object or a person, and whether the person is a child or an adult can be detected. Thus, a most appropriate solution to the bump can be handled.

For example, airbags for pedestrians are recently available which opens outside of a windshield in order to inhibit a bumped pedestrian from being injured. In this operation, speed is required more than in the operation of a conventional driver's seat airbag. More detailed detection of bump conditions is also required. These kinds of operation become possible by using the above-described contact tags.

In a case wherein wireless tags are used for such bump detection, accurate detection of a bump is difficult only by the wireless tags. This is because wireless tags conduct wireless communication when tags are located near to each other. Moreover, wireless tags cannot distinguish an object which will not to be in contact, and an object which will be in contact. Therefore, in a case wherein wireless tags are used, the wireless tags should be preferably used for the purpose of preparation before a bump takes place, in addition to bump detection by using contact communication as described in the present embodiment. For example, in case detection is attempted in a bump against a pedestrian having a wireless tag by using a wireless tag receiver installed in a car, communication is made irrespective to whether the pedestrian and the car are in a non-contact state or in a contact state. Thus, whether the pedestrian and the car are actually bumped cannot be detected. In a case wherein there is a plurality of pedestrians having wireless tags, a party who has been bumped cannot be specified. However, a wireless tag can be used in combination with a contact communication device, in order to predict a party who can be possibly bumped based on information from the wireless tag, so that an airbag for pedestrians becomes ready, and the airbag for pedestrians is operated when a bump is detected by the contact communication device. As for a non-contact detection technique other than by using wireless tags, there is a technique wherein a car bump is predicted by detecting a distance by a radar. However, this alone cannot accurately detect a contact. This is because radar cannot detect a minute distance whether or not a car is in contact. Moreover, a radar can only detect the distance from a radar antenna, but cannot detect the distance from the surface of a car. On the other hand, in contact communication, the distance, not from a contact communication device, but from the surface of a car can be accurately detected. In addition, such detection becomes possible by only one contact communication device, as long as a contact path is provided.

Figure 59:
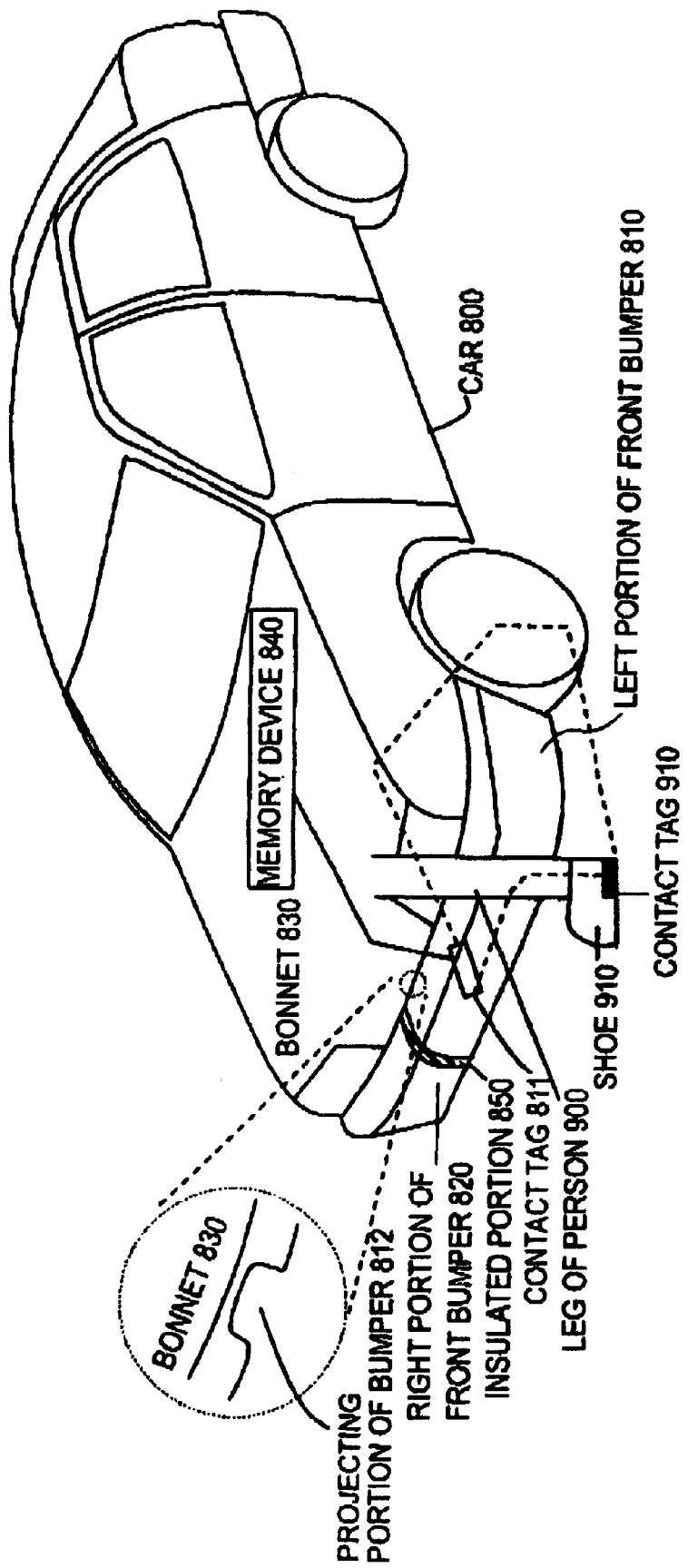
FIG. 59 is an explanatory view of a car in a case of detecting a car bump by contact communication.

FIG. 59 shows a car 800 provided, to a bumper, with a contact tag which detects such bumps. The bumper is made of an insulating material. The top surface and the front surface of the bumper are coated with a conductive material. Only a surface 850 of a mid portion of the bumper is coated with an insulating material. Due to the coating, the left portion and the right portion of the bumper are insulated. The bumper and the car body are also insulated. In a connecting portion between a left portion 810 of the bumper and the car body, a contact tag 811 is disposed. One of the electrodes of the contact tag 811 is connected to the car body. The other electrode is connected to the surface of the left portion of the bumper (the conductive portion). In this state, if, for example, a leg 900 of a person touches the left portion 810 of the bumper, a contact path is formed as follows: the leg 900 of the person→the left portion 810 of the bumper→the contact tag 811→the car body→a wheel→the ground→a contact tag 911 on a shoe which the foot of the person wears→the leg 900 of the person. Thus, the person who the car bumped against can be detected.

A bump may be alternatively detected by a contact path formed by the bumper and the car body coming into contact when a bump takes place. For example, a projection 812 is provided to the left portion of the bumper. When a bump takes place, the bumper is pushed and the projection 812 of the left portion of the bumper contacts with the car body. Therefore, a contact path is formed as follows: the projection 812 of the left portion of the bumper→car body→contact tag 811→projection 812 of the left portion of the bumper. Consequently, the bump can be detected. In this case, the contact tag 811 conducts sending and receiving at the same time. The contact tag 811 detects that a contact is made by the projection 812 of the left portion of the bumper, by receiving a signal sent by the contact tag 811 itself. If simultaneous sending and receiving by one contact tag is difficult, the contact tag 811 may be constituted with two contact tags: one contact tag only for sending, and another contact tag only for receiving.

Figure 60:
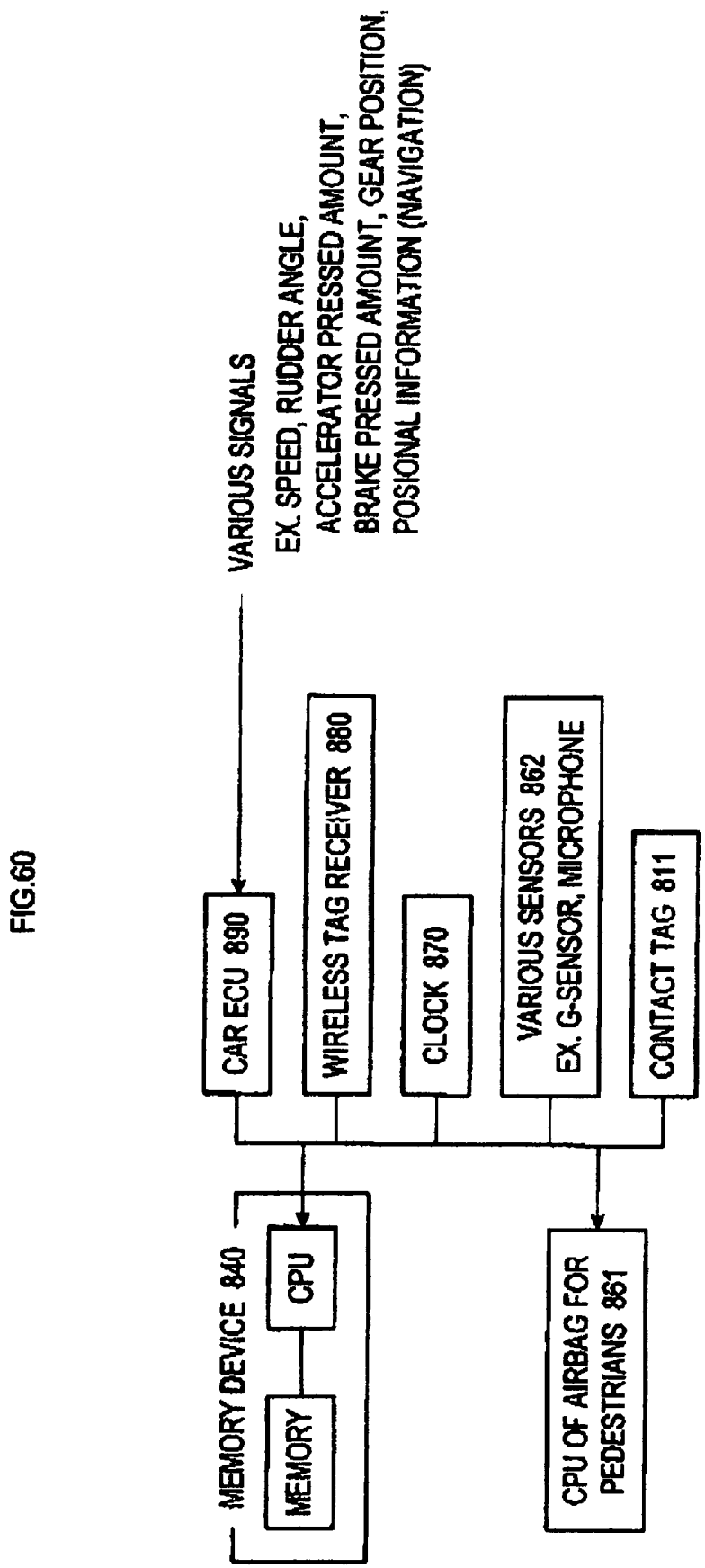
FIG. 60 is a configuration view of the car in the case of detecting a car bump by contact communication.

FIG. 60 is a block diagram showing bump detection performed by using this contact communication. Information is sent to a CPU 861 of an airbag for pedestrians and to a memory device. For example, car state quantity, such as speed, is sent from an ECU 890 of the car. Communication information with wireless tags (not shown), provided to people existing in the vicinity of the car, is sent from the wireless tag receiver 880. Information regarding time is sent from a clock 870. Data of shock G and sound, such as bump sound, are sent from various sensors 862. Contact communication data from a plurality of contact tags, including the above-described contact tag 811, which detect contact at respective portions of the car, is sent from the contact tags. Based on such information, determination for operating an airbag (not shown) for pedestrians is made.

In FIG. 61, algorithms for recording such minor collision accidents are shown. A memory of a memory device 840 in FIG. 60 includes a plurality of two-hour endless memory areas which consistently keeps storing the latest information by writing over memory data, stored two hours ago, just as a two hour endless tape does. Every time an accident and the like are suspected, the plurality of endless memory areas is constituted so as to store information for two hours in total before and after the accident.

FIGS. 61(A) and (B) show algorithms for a case wherein such storing is conducted in the memory device 840 in FIG. 60, which is consistently operated parallel to the operation of the car after the car is manufactured. For example, in FIG. 61(A), when contact is detected in S81 between the leg 900 of a person and the car, as shown in FIG. 59, and the car is determined to be moving according to the speed data in the ECU 890 of the car, a timer is started in S83. In FIG. 61(B), in one of the endless memory areas of the memory of the memory device 840, latest data in two hours, among data inputted into the CPU of the memory device 840, is consistently stored. In a case wherein the timer is a one-hour timer, recording into the endless memory area, in which recording is currently being performed, is stopped when the one-hour timer, started in S83 in FIG. 61(A), is determined to be terminated in S86 in FIG. 61(B). Then, in S87, recording into another endless memory area is started. In this manner, data for two hours in total before and after the crucial time, such as an accident and the like, can be stored. If S82 is omitted, memory in the endless memory areas can be preserved even the car is in a stop state. In case a car burglary takes place, data for two hours in total before and after the burglary can be preserved.

Next, an application example into a gas station is described with reference to FIG. 62.

In front of a fuel supplier 1100 of a gas station, a conductive are 1202 is disposed such that only a wheel disposed nearest to a fuel supply opening can enter therein. The fuel supplier 1100 is provided with a contact tag 1102. An electrode disposed in the lower portion of the tag is constituted so as to be conductively connected to the conductive area 1200, while the electrode is insulated from the fuel supplier 1100. An electrode disposed in the upper portion of the tag is constituted so as to be conductively connected with the fuel supplier 1100. This can be acquired in the same manner as in the contact tag 1*u* in FIG. 46(A).

The fuel supply opening 1010 of a car 1000 is provided with a contact tag 1014. When a fuel supply gun 1101 is inserted into the fuel supply opening 1010 for fueling, the leading end of the fuel supply gun 1101 contacts with an upper conductive portion 1011 of the fuel supply opening 1010. Consequently, a contact path is formed as follows: the contact tag 1102 of the fuel supplier 1100→the fuel supplier 1100→the fuel supply gun 1101→the upper conductive portion 1011 of the fuel supply opening→the contact tag 1014 of the fuel supply opening→the lower conductive portion 1013 of the fuel supply opening→the car body→the wheel→the conductive area 1200→the contact tag 1102 of the fuel supplier 1100. Due to this contact path, the contact tag 1102 of the fuel supplier 1100 communicates with the contact tag 1014 of the fuel supply opening so that fueling determination is made and fueling can be initiated.

If a wireless tag is disposed in the vicinity of a fuel supply opening of a car, and fueling is to be determined by communication between the wireless tag and the fuel supplier, problems are caused with the wireless tag such that communication cannot be performed if the direction of the antenna does not match, such that radio wave is reflected and unexpected communication is established, and so on. Because of these problems, if the radio wave is strengthened so as to reduce the communication inability, or a frequency is selected so that the radio wave is transmitted to a wide area, or the communicable area is enlarged by making the antenna larger and the like, there is some tradeoff: information theft can be more easily caused. Moreover, in order not to cause communication inability in any type of car, the installation position and the direction of an antenna need to be precisely set, and the setting has to be standardized for every type of car. In this way, communication inability can be reduced by precise setting of an antenna of a wireless tag or by standardizing the setting. However, good communication ability and zero radio wave leakage are in a tradeoff relation. The more attempt is made so as to reduce communication inability, the more radio wave leaks. The more attempt is made so as to reduce radio wave leakage, the more communication inability is caused. Keeping both of good communication ability and zero radio wave leakage is difficult. Communication leakage is inevitably caused.

On the other hand, in a case wherein contact communication is used, information does not leak, even if someone touches a car body, because a contact path is not formed. Moreover, even if someone attempts to obtain contact communication electric current spread over a car body, the contact communication electric current cannot be detected, because minute electric current equal to or smaller than 500 µA is originally spread all over the car body. Furthermore, in the present embodiment, the conductive are 1202, which becomes a part of a contact path, is determined to be a narrow area in vicinity of the fuel supplier 1100 such that only one wheel can fit therein. Therefore, a contact path exists only in vicinity of a person who supplies fuel, and information theft from this contact path can be easily inhibited.

As described above, communication maintaining both reliability and safety of communication, wherein communication disability is not caused and information leakage to a third person does not take place, becomes possible.

Addition of Embodiments

Various applications of the present invention, other than the ones described above, can be conceived. That is, the present invention is not limited to the above-described embodiments. Variations may be possible without departing from the scope of the invention. The contact path in the present invention is not limited to a path wherein electric current constantly flows. The contact path may be, for example, an electrostatically coupled path wherein a floor or ground is used as a common grounded electrode.

The conductive material in the present invention means a material capable of contact communication. Insulation in the present invention is to block contact communication. Both are slightly different from the general meanings of insulation and conductivity.

The contact communication is a technique wherein communication is established basically when contact is made. In a precise sense, communication is possible in a separate state wherein there is a minute distance created immediately before contact is made, due to electrostatic coupling. The communication distance in a non-contact state can be adjusted by adjusting applied voltage and the like of contact communication. Therefore, in the present invention, detection can be performed not only when contact is made, but also immediately before and after the contact.

The contact path, in which contact communication is performed, is not limited to the closed circuit in the embodiments. So-called waveguide type human body communication, for example, may be applied thereto. In contact communication of so-called waveguide type, communication can be established without a closed circuit being formed, if two contact tags are coupled by a conductive material. For example, this type of communication can be used for contact made with volley ball players. In this case, players wear waveguide type contact tags, and a ball is made of a conductive material and having a waveguide type contact tag installed therein. If shoes of the players or the floor of a court is made of an insulating material, and when the ball contact with a player, the contact tag of the player and the contact tag of the ball conduct contact communication. Thus, whether the ball has contacted with the player can be detected.

Furthermore, the clocks in the present embodiments are all wave clocks. The time in the present embodiments means the time that the wave clocks indicate. However, the clocks are not limited to wave clocks. The clocks may be any clock as long as the relation between before and after contact is made can be known thereby. For example, instead of a wave clock, time may be recorded through a LAN and the like, such that the time indicated by one clock is adopted as a reference time, and that time according to the reference time is recorded. Alternatively, instead of a clock, one counter or the like, from which the relation between before and after contact is made can be known, may be used. By using the counter number of a counter, the relation between before and after contact communication can be known.

In case contact communication is used, opening various items, such as opening a medicine bottle, can be detected. Detection of opening a software CD, for example, may be possible. When opening a software CD is detected, a software company may be informed by some kind of communication method, such as communication with a personal computer.

S1, S11, S31, S41, S42, S65, S66, and S71 in the processes in the respective embodiments described above correspond to the detection device. S7 and S17 correspond to the first warning device and the second warning device respectively. The wireless station 61 corresponds to the position detection device.

The contact path, in which contact communication is performed, is not limited to the closed circuit in the embodiments. So-called waveguide type human body communication, for example, may be applied thereto. In contact communication of so-called waveguide type, communication can be established without a closed circuit being formed, if two contact tags are coupled by a conductive material. For example, this type of communication can be used for contact made with volley ball players. In this case, players wear waveguide type contact tags, and a ball is made of a conductive material and having a waveguide type contact tag installed therein. If shoes of the players or the floor of a court is made of an insulating material, and when the ball contact with a player, the contact tag of the player and the contact tag of the ball conduct contact communication. Thus, whether the ball has contacted with the player can be detected.

Lastly, the effect of the present invention is described.

Contact communication is special communication wherein communication is conducted only when contact communication is made. In addition, communication is not conducted unless contact is actually made. Consequently, by keeping communication record of contact communication, a contacted target can be specified from the communication record of the contact communication. Furthermore, the moment of contact can be accurately found out. As a result, the order of contacted objects, in what order objects are contacted, can be found out.

Since even the moment of contact can be precisely found out, data acquired when contact is actually and undeniably made (to be refereed to as real data) can be obtained in combination with accurate time according to a wave clock.

For example, if supposedly, a person performs an operation while watching time, and the person can perfectly memorize the time when he/she performed the operation, the content of the operation and the time may be inputted by a computer or the like. However, a human being cannot look at the time in the moment of an operation that person is performing. Therefore, data of every moment when operation is actually performed cannot be acquired. Naturally, inputting data of the content of operation and the time when the operation was actually performed without any omission takes an immense amount of effort, and is impossible. If collection of detailed data is attempted, time required for inputting such data becomes as long as the time that was required when the operation was performed. This is also impossible. As described above, real data cannot be obtained except by contact communication.

A case, wherein a wireless tag is used, is considered below.

Wireless communication, in the essential characteristics thereof, is a type of communication in which a communicable area cannot be clearly defined. The communicable area changes depending on time and situation. Therefore, a communicable area cannot be strictly specified. For example, a following case is conceived. In this case there are a wireless tag receiver, having a communication area in an entire nurse station, and nurses, provided with wireless tags which can communicate with the receiver, in a nurse station. Through wireless communication, exactly where the nurses are in the nurse station cannot be found out. Since the wireless communication area changes depending on time and situation, the detection area is unstable such that a nurse is detected although the nurse is in a corridor near the nurse station, or on the other hand, a nurse B cannot be detected due to radio disturbance or the like, although the nurse B is in the nurse station. Obviously, whether or not a nurse has touched an important medicine bottle cannot be detected. For example, in a case wherein an important medicine bottle and all nurses are respectively provided with wireless tags which can conduct wireless communication, the wireless tag of the important medicine bottle can detect nurses existing nearby. However, if a plurality of nurses exists near the medicine bottle, the wireless tag detects the plurality of nurses, but cannot detect so as to specify the nurse who has touched the bottle. As described above, detection so as to exactly specify a position is not possible by using wireless tags. Consequently, specifying time, from when to when the person was in that place, cannot be specified even if a wave clock is used.

On the other hand, use of contact communication enables to exactly specify a position, and even to detect a movement of a nurse, whether or not the nurse has touched the medicine bottle. By using the time according to a wave clock, actual data of such information (position and movement) can be detected. Because such real data can be obtained, and the order or the place of a performed operation can be exactly specified, determination of an error becomes possible. Moreover, because data is real data, an error can be inhibited before an error is made. As described above, when, where, who has done what and how can be precisely detected as real data. From the timing of contact, the condition and the movement, such as what is used in what combination, or who is going to deal with what and how, can be detected. Such various determinations become possible because real data can be obtained.

In the embodiment of a hospital, the latest state of current operations of other staffs can be also checked. Therefore, instructions can be given depending on a current situation (for example, there is an emergency operation, etc.).

If manual input of data is required regarding operation time and the like, such input becomes troublesome and waste of time. Medical treatment urgently required cannot be performed. Moreover, mismatch between manually inputted data and real data may be caused, or non-input of some data may occur. Since the data is not reliable, an error check based on the data cannot be conducted.

On the other hand, by contact communication, every moment of each of medical treatment, including before and after the treatment, can be precisely detected. Contact communication renders manual input unnecessary, and also enables to precisely detect the order (procedure) of medical treatment which has been actually performed. If a nurse follows a correct medical procedure, actual action history is automatically inputted in a precise manner without manual input into a computer. Whether a correct medical procedure is performed can be also checked.

Furthermore, the portion where contact has been made can be accurately detected, as in the embodiment of car bump detection. In the example of a hospital, if contact tags are disposed in a detailed manner, a detailed operation procedure can be detected. For example, in a blood drawing method wherein a vacuum bottle is used, there is a problem such that while an injector is inserted into an arm, and if the timing to remove a rubber band is inappropriate, blood in the vacuum bottle reversely flows and bacteria in the vacuum bottle enters a body. By providing contact tags on an injector, rubber band, and so on, such procedure can be recorded and checked.

Moreover, if impedance of a human body and the like when contact is made is detected and recorded, previous procedure (way of contact, contacted part) can be estimated, and the data can be used for verification, in case medical malpractice takes place. Additionally, in a case wherein hospital infection is caused, the cause can be investigated from the people's or objects' contact record stored by the contact communication device.

With regard to the production embodiment at a factory, the present invention may be applied not only to the belt conveyer production system, but also to the booth production (cell production) system. Specially, if wireless tags are disposed so as to detect fetching of parts in a small place, such as a factory line or a pharmacy, fetched parts cannot be accurately detected due to error detection performed by a wireless tag disposed nearby. If detection of fetched parts is attempted by using some other device, disposition of such detection device in every compartment of a shelf is difficult in terms of space. This device is also subjected to cause malfunction when neighboring parts are fetched.

On the other hand, contact communication requires only the formation of a contact path. In order to detect parts, sensors are not needed to be disposed where parts are stored. That is, a contact tag itself can be disposed anywhere in a contact path. Therefore, only a conductive material needs to be disposed in every compartment of a parts shelf so as to form a contact path. In addition, since contact tags are not operated even if operation is performed in vicinity, unless contact is actually made with parts, extremely accurate detection without malfunction becomes possible.

Switches, such as ordinary buttons, or detection sensors for detecting fetched parts can perform detection of limited areas. However, in contact communication, detection can be performed anywhere in a contact path. Therefore, flexibility in a limited space, such as in a factory, can be increased.

Moreover, rate-limiting control can be conducted so as to find out which operation in a factory line has been slow. Education for production procedure becomes unnecessary. Even if refrigerators in various types and specifications are conveyed in a line, according to the instruction of an instruction computer, parts can be attached without an error. Even if production of refrigerators is changed in a flexible manner, operators can perform operations without errors, because an instruction computer gives instructions based on the production changes.

Furthermore, by using the capability in detecting and recording operation procedure in real time, operation timings of a skilled operator and a beginner can be recorded and compared so as to be used for acquiring operation proficiency.

In the embodiment of a pharmacy, since the state of pharmacists and the state of medicine can be detected in real time, a scale can be automatically adjusted to a current situation. Switching on the scale and setting the scale are not necessary, as usually required with an ordinary scale. Therefore, human error which tends to be caused in such input can be inhibited.

The example of prescription at a pharmacy shown in FIG. 36, and the example of production method at a factory shown in FIG. 46 may be applied in a shop. For example, current convenience stores are run by inexperienced part-time workers, although complicated various operations are carried out therein. Consequently, store staffs come across with operations they don't know well. In such case, for example, if a customer approaches a casher and says "a post card, please", the word postcard is detected through a microphone installed at the casher, and a lamp in a post card shelf in a counter of the casher is turned on. When the store staff sees the lamp and touches the postcard shelf, contact communication devices respectively provided to the shelf and the staff perform contact communication, and detect that the staff has touched the postcard shelf so as to control the lamp to be turned off and to navigate the staff.

Automatic flushing for today's urinals can detect only whether or not a person is standing in front of the urinal. Thus, flushing is performed with excessive amount of water, or, to the contrary, odor of urine cannot be effectively reduced. If flushing is controlled by providing contact communication devices to a human body and a urinal respectively, time when a person urinates is measured while contact communication is made via urine, a most suitable flushing becomes possible. Furthermore, current automatic flushing system flushes water when a person is just standing in front of a urinal. Such unnecessary flushing can be inhibited.

Other than the above examples, if contact communication devices are provided to training machines at a training gym and users respectively, and when a user makes contact every time the user uses the training machine, automatic setting of the training machine for every user may be possible. In this case, interference, which may be caused in wireless communication, between other training machines disposed nearby, or between other people may be inhibited.

If contact communication devices are provided to hand-carried baggage and owners respectively, detection may be made when the hand-carried baggage is released, and baggage is inhibited from being left behind.

Furthermore, if contact communication devices are provided to a floor of a corridor or to a hand rail and senior adults, wandering of senior adults may be detected.

The invention claimed is:
1. A communication apparatus comprising:
  communication devices respectively attached to a first object and a second object, the communication devices mutually performing communication via a communication path through the first object, the second object, a living body and a conductive path of a conductive floor when the first object and the second object contact directly or indirectly via an intervening medium; and
  a data comparison device that compares data received from one of the first object and the second object during communication performed between the first object and the second object by the communication devices and data stored in a predetermined storage area, wherein the data stored in the storage area includes confusing data which is difficult to be distinguished from a plurality of data; and the data comparison device compares whether or not the data received from the one of the first object and the second object coincides with the confusing data, and makes one of a determination that the received data is confusing when the received data coincides with the confusing data and a determination that the received data is not confusing when the received data does not coincide with the confusing data.

2. The communication apparatus as set forth in claim 1, wherein the communication path further includes a conductive path provided in a medical apparatus.

3. The communication apparatus as set forth in claim 1, wherein the confusing data comprises an article name or a person's name.

4. A communication apparatus comprising:

communication devices respectively attached to a first object and a second object, the communication devices mutually performing communication via a communication path through the first object, the second object, a living body and a conductive path of a conductive floor when the first object and the second object contact directly or indirectly via an intervening medium; and a data comparison device that compares data received from one of the first object and the second object during communication performed between the first object and the second object by the communication devices and data stored in a predetermined storage area, wherein the data stored in the storage area includes data of a correct corresponding object to be combined with the recipient object; and the data comparison device compares whether or not the data received from the one of the first object and the second object coincides with the data of the correct corresponding object to be combined, and makes one of a determination that the received data is correct when the received data coincides with the correct corresponding data and a determination that the received data is incorrect when the received data does not coincide with the correct corresponding data.

5. The communication apparatus as set forth in claim 4, wherein the communication path further includes a conductive path provided in a medical apparatus.

6. The communication apparatus as set forth in claim 4, wherein the received data and the data stored in the storage area comprise an article name or a person's name.

7. A communication apparatus comprising:

communication devices respectively attached to a first object and a second object, the communication devices mutually performing communication via a communication path through the first object, the second object, a living body and a conductive path of a conductive floor when the first object and the second object contact directly or indirectly via an intervening medium; and a data comparison device that compares data received from one of the first object and the second object during communication performed between the first object and the second object by the communication devices and data stored in a predetermined storage area, wherein the data stored in the storage area includes data of an incorrect corresponding object to be combined with the recipient object; and the data comparison device compares whether or not the data received from the one of the first object and the second object coincides with the data of the incorrect corresponding object to be combined, and makes one of a determination that the received data is incorrect when the received data coincides with the incorrect corresponding data and a determination that the received data is correct when the received data does not coincide with the incorrect corresponding data.

8. The communication apparatus as set forth in claim 7, wherein the communication path further includes a conductive path provided in a medical apparatus.

9. The communication apparatus as set forth in claim 7, wherein the data received from one of the first object and the second object and the data stored in the predetermined storage area comprise an article name or a person's name.

10. A communication apparatus comprising:

communication devices respectively attached to a plurality of objects, the communication devices mutually performing communication via a communication path through the plurality of objects, a living body and a conductive path of a conductive floor when the plurality of objects contact directly or indirectly via an intervening medium; and a data comparison device that compares a combination of data transmitted from one of the plurality of objects during communication performed between the plurality of objects by the communication devices and data set in the recipient object with a combination of data stored in a predetermined storage area, wherein the combination of data stored in the storage area is a correct combination of data; and the data comparison device compares whether or not the combination of data transmitted from the one of the plurality of objects and data set in the recipient object coincides with the correct combination of data, and makes one of a determination that the combination of the transmitted data and the set data is correct when the combination of the transmitted data and the set data coincides with the correct data and a determination that the combination of the transmitted data and the set data is incorrect when the combination of the transmitted data and the set data does not coincide with the correct data.

11. The communication apparatus as set forth in claim 10, wherein the communication path further includes a conductive path provided in a medical apparatus.

12. The communication apparatus as set forth in claim 10, wherein the combination of data transmitted from one of the plurality of objects, the data set in the recipient object and the combination of data stored in the predetermined storage area comprise an article name or a person's name.

13. A communication apparatus comprising:

communication devices respectively attached to a plurality of objects, the communication devices mutually performing communication via a communication path through the plurality of objects, a living body and a conductive path of a conductive floor when the plurality of objects contact directly or indirectly via an intervening medium;

a data combination creation device that creates a combination of associated data from the data transmitted from the one of the plurality of objects and the data set in the recipient object during communication between the plurality of objects by the communication device; and a data comparison device that compares the combination of data created by the data combination creation device with the combination of data stored in the predetermined storage area, wherein
the combination of data stored in the storage area is a correct combination of data; and
the data comparison device compares whether or not the combination of data created by the data combination creation device coincides with the correct combination of data, and makes one of a determination that the created combination of data is correct when the created combination of data coincides with the correct data and a determination that the created combination of data is incorrect when the created combination of data does not coincide with the correct data.

14. The communication apparatus as set forth in claim 13, wherein the communication path further includes a conductive path provided in a medical apparatus.

15. The communication apparatus as set forth in claim 13, wherein the combination of data created by the data combination device and the combination of data stored in the predetermined storage area comprise an article name or a person's name.

16. A communication apparatus comprising:
data communication devices respectively attached to an operator, and a person or an object as an operation target, the data communication devices mutually performing data communication when the operator contacts the person or the object and thereby a path is formed through the operator, the person or the object and a conductive path of a conductive floor;
a data comparison device that compares a combination of the operator, and the person or the object corresponding to data communication performed by the data communication device with a combination stored in a predetermined storage area as a correct combination; and
a warning device that gives a warning when, as a result of comparison by the data comparison device, the combination of the operator, and the person or the object corresponding to data communication does not coincide with the combination stored in the predetermined storage area as the correct combination.

17. The communication apparatus as set forth in claim 16 further comprising:
a detection device that detects the data communication performed between the data communication devices; and
a storage device that stores information indicating the operator, the person or the object corresponding to the data communication detected by the detection device.

18. The communication apparatus as set forth in claim 17 further comprising:
a clock device that clocks time; and
a detection device that detects the data communication performed between the data communication devices together with the time of the data communication.

19. The communication apparatus as set forth in claim 18 further comprising:
a position detection device that detects a position of the operator, the person or the object via wireless communication; and
a detection device that detects the data communication performed between the data communication devices together with the position detected by the position detection device as the position of the operator, the person or the object in which the data communication is performed.

20. The communication apparatus as set forth in claim 16, wherein the path formed through the operator, the person or the object and the conductive path of the conductive floor further includes a conductive path provided in a medical apparatus.

21. The communication apparatus as set forth in claim 16, wherein the combination of the operator and the combination stored in the predetermined storage area comprise an article name or a person's name.

22. A communication apparatus comprising:
data communication devices respectively attached to an operator, and a person or an object as an operation target, the data communication devices mutually performing data communication when the operator contacts the person or the object and thereby a path is formed through the operator, the person or the object and a conductive path of a conductive floor;
a data comparison device that compares the person or the object corresponding to data communication performed by the data communication device with a person or an object stored in a predetermined storage area as a confusing, mistakable person or object; and
a warning device that gives a warning when, as a result of comparison by the data comparison device, the person or the object corresponding to the data communication detected by the detection device includes the person or the object stored in a predetermined storage area as a confusing, mistakable person or object.

23. The communication apparatus as set forth in claim 22 further comprising:
a detection device that detects the data communication performed between the data communication devices; and
a storage device that stores information indicating the operator, the person or the object corresponding to the data communication detected by the detection device.

24. The communication apparatus as set forth in claim 23 further comprising:
a clock device that clocks time; and
a detection device that detects the data communication performed between the data communication devices together with the time of the data communication.

25. The communication apparatus as set forth in claim 24 further comprising:
a position detection device that detects a position of the operator, the person or the object via wireless communication; and
a detection device that detects the data communication performed between the data communication devices together with the position detected by the position detection device as the position of the operator, the person or the object in which the data communication is performed.

26. The communication apparatus as set forth in claim 22, wherein the path formed through the operator, the person or the object and the conductive path of the conductive floor further includes a conductive path provided in a medical apparatus.

27. The communication apparatus as set forth in claim 22, wherein the data communication performed by the data communication devices includes data representing an article name or a person's name, and the data comparison device compares the communicated article name or person's name with a list of confusing, mistakable article names or people's names to determine whether the communicated article name or person's name is a confusing, mistakable article name or person's name.

* * * * *

UNITED STATES PATENT AND TRADEMARK OFFICE
CERTIFICATE OF CORRECTION

| | |
|---|---|
| PATENT NO. | : 7,911,342 B2 |
| APPLICATION NO. | : 11/664629 |
| DATED | : March 22, 2011 |
| INVENTOR(S) | : Takaharu Sekine |

It is certified that error appears in the above-identified patent and that said Letters Patent is hereby corrected as shown below:

Col. 2, Line 66
 Delete "2690614"
 Insert --2690514--

Col. 5, Line 65
 Delete "465"
 Insert --455--

Col. 10, Line 52
 Delete "NO"
 Insert --NG--

Col. 11, Line 38
 Insert --;-- after "characters"

Col. 13, Line 20
 Delete "60"
 Insert --50--

Col. 13, Line 22
 Delete "65c"
 Insert --55c--

Col. 13, Line 22
 Delete "56a"
 Insert --55a--

Signed and Sealed this
Fourteenth Day of February, 2012

David J. Kappos
*Director of the United States Patent and Trademark Office*

Col. 13, Line 26
  Delete "66"
  Insert --56--

Col. 13, Line 27
  Delete "56"
  Insert --55--

Col. 13, Line 38
  Delete "67a"
  Insert --57a--

Col. 17, Line 18
  Delete "A"
  Insert --a--

Col. 19, Line 58
  Delete "36"
  Insert --35--

Col. 25, Line 5
  Delete "ease"
  Insert --case--

Col. 26, Line 61
  Delete "bottle 260"
  Insert --bottle 250--

Col. 26, Line 63
  Delete "262a"
  Insert --252a--

Col. 27, Line 55
  Delete "260"
  Insert --250--

Col. 28, Line 12
  Delete "280"
  Insert --230--

Col. 28, Line 57
  Delete "260"
  Insert --250--

CERTIFICATE OF CORRECTION (continued)
U.S. Pat. No. 7,911,342 B2

Col. 28, Line 63
 Delete "260"
 Insert --250--

Col. 29, Line 57
 Delete "tag is"
 Insert --tag 1s--

Col. 29, Line 58
 Delete "tag is"
 Insert --tag 1s--

Col. 29, Line 64
 Delete "tag is"
 Insert --tag 1s--

Col. 29, Line 65
 Delete ";"
 Insert --:--

Col. 29, Line 67
 Delete "tag is"
 Insert --tag 1s--

Col. 30, Line 47
 Delete "80"
 Insert --50--

Col. 31, Line 62
 Delete "360"
 Insert --350--

Col. 33, Line 7
 Delete "360"
 Insert --350--

Col. 35, Line 19
 Delete "462"
 Insert --452--

Col. 35, Line 24
 Delete "463b"
 Insert --453b--

Col. 35, Line 29
 Delete "462"
 Insert --452--

Col. 36, Line 36
 Delete "610"
 Insert --510--

Col. 36, Line 43
 Delete "612"
 Insert --512--

Col. 36, Line 55
 Delete "630"
 Insert --530--

Col. 37, Line 16
 Delete "600"
 Insert --500--

Col. 37, Line 45
 Delete "633"
 Insert --533--

Col. 37, Line 46
 Delete "633"
 Insert --533--

Col. 37, Line 46
 Delete "631a"
 Insert --531a--

Col. 37, Line 67
 Delete "631"
 Insert --531--